US010487163B2

(12) United States Patent
Shin et al.

(10) Patent No.: US 10,487,163 B2
(45) Date of Patent: Nov. 26, 2019

(54) CYCLOPENTA[B]FLUORENYL TRANSITION METAL COMPOUND, CATALYST COMPOSITION CONTAINING THE SAME, AND METHOD OF PREPARING ETHYLENE HOMOPOLYMER OR COPOLYMER OF ETHYLENE AND ALPHA-OLEFIN USING THE SAME

(71) Applicant: Sabic SK Nexlene Company Pte. Ltd., Singapore (SG)

(72) Inventors: Dong Cheol Shin, Daejeon (KR); Jong Sok Hahn, Daejeon (KR); Chan Woong Jeon, Daejeon (KR); Jeong Hwan Kim, Daejeon (KR); Seong Kyun Kim, Daejeon (KR); Sun Young Kim, Daejeon (KR); Ho Seong Lee, Daejeon (KR); Sang Ick Lee, Daejeon (KR)

(73) Assignee: Sabic SK Nexlene Company Pte. Ltd., Singapore (SG)

( * ) Notice: Subject to any disclaimer, the term of this patent is extended or adjusted under 35 U.S.C. 154(b) by 0 days.

(21) Appl. No.: 16/292,745

(22) Filed: Mar. 5, 2019

(65) Prior Publication Data

US 2019/0202949 A1    Jul. 4, 2019

Related U.S. Application Data

(62) Division of application No. 15/832,011, filed on Dec. 5, 2017, now Pat. No. 10,323,111, which is a division of application No. 14/789,512, filed on Jul. 1, 2015, now Pat. No. 9,926,394, which is a division of application No. 13/881,098, filed as application No. PCT/KR2012/004511 on Jun. 8, 2012, now Pat. No. 9,120,884.

(30) Foreign Application Priority Data

Jun. 9, 2011   (KR) .................. 10-2011-0055719
Jun. 1, 2012   (KR) .................. 10-2012-0059441

(51) Int. Cl.

| | | |
|---|---|---|
| C07C 13/66 | (2006.01) |
| C08F 210/16 | (2006.01) |
| C08F 4/76 | (2006.01) |
| C08F 4/6592 | (2006.01) |
| C08F 210/02 | (2006.01) |
| C07F 17/00 | (2006.01) |
| C08F 210/18 | (2006.01) |
| C08F 210/06 | (2006.01) |
| C07F 7/28 | (2006.01) |
| C07F 7/08 | (2006.01) |
| C08F 4/659 | (2006.01) |
| C08F 210/14 | (2006.01) |

(52) U.S. Cl.
CPC .............. C08F 210/16 (2013.01); C07F 7/28 (2013.01); C07F 17/00 (2013.01); C08F 4/6592 (2013.01); C08F 4/76 (2013.01); C08F 210/02 (2013.01); C08F 210/06 (2013.01); C08F 210/18 (2013.01); C07C 13/66 (2013.01); C07F 7/0816 (2013.01); C08F 4/65908 (2013.01); C08F 4/65912 (2013.01); C08F 210/14 (2013.01); C08F 2420/02 (2013.01); Y10S 526/943 (2013.01)

(58) Field of Classification Search
CPC ...................................................... C07C 13/66
See application file for complete search history.

(56) References Cited

U.S. PATENT DOCUMENTS

| | | | |
|---|---|---|---|
| 4,752,597 | A | 6/1988 | Turner |
| 5,055,438 | A | 10/1991 | Canich |
| 5,103,030 | A | 4/1992 | Rohrmann et al. |
| 5,198,401 | A | 3/1993 | Turner et al. |
| 5,329,050 | A | 7/1994 | Weisse et al. |
| 5,703,187 | A | 12/1997 | Timmers |
| 6,329,478 | B1 | 12/2001 | Katayama et al. |
| 6,515,155 | B1 | 2/2003 | Klosin et al. |
| 6,806,326 | B2 | 10/2004 | Stevens et al. |
| 7,030,256 | B2 | 4/2006 | Boussie et al. |
| 7,098,356 | B2 | 8/2006 | Graf et al. |
| 7,557,171 | B2 | 7/2009 | Voskoboynikov et al. |
| 7,732,052 | B2 | 6/2010 | Chang et al. |

(Continued)

FOREIGN PATENT DOCUMENTS

| | | |
|---|---|---|
| CN | 101481392 A | 7/2009 |
| EP | 0320762 A2 | 6/1989 |
| EP | 0372632 A1 | 6/1990 |

(Continued)

OTHER PUBLICATIONS

No new references.*

(Continued)

*Primary Examiner* — Shawquia Jackson

(74) *Attorney, Agent, or Firm* — The Webb Law Firm

(57) ABSTRACT

The present invention relates to a new transition metal compound based on cyclopenta[b]fluorenyl group, a transition metal catalyst composition containing the same and having high catalytic activity for preparing an ethylene homopolymer or a copolymer of ethylene and one α-olefin, a method of preparing an ethylene homopolymer or a copolymer of ethylene and α-olefin using the same, and the prepared ethylene homopolymer or the copolymer of ethylene and α-olefin.

1 Claim, No Drawings

(56) References Cited

U.S. PATENT DOCUMENTS

| | | |
|---|---|---|
| 8,343,886 B2 | 1/2013 | Beigzadeh et al. |
| 2009/0176948 A1 | 7/2009 | Shin et al. |

FOREIGN PATENT DOCUMENTS

| | | |
|---|---|---|
| EP | 0416815 A1 | 3/1991 |
| EP | 0420436 A1 | 4/1991 |
| EP | 0568879 A1 | 11/1993 |
| EP | 0842939 A1 | 5/1998 |
| EP | 1866322 B1 | 2/2010 |
| JP | 63092621 A | 4/1988 |
| JP | 02084405 A | 3/1990 |
| JP | 03002347 A | 1/1991 |
| JP | 3163088 A | 7/1991 |
| JP | 2003516420 A | 5/2003 |
| JP | 2005519969 A | 7/2005 |
| JP | 2007529617 A | 10/2007 |
| JP | 2008503603 A | 2/2008 |
| KR | 1020020063207 A | 8/2002 |
| KR | 1020050112135 A | 11/2005 |
| KR | 100976666 B1 | 8/2010 |
| WO | 2006065809 A2 | 6/2006 |

OTHER PUBLICATIONS

Dietrich et al.; "Control of Stereoerror Formation with High-Activity "Dual-Side" Zirconocene Catalysts: A Novel Strategy to Design the Properties of Thermoplastic Elastic Polypropenes"; J. Am. Chem. Soc.; 1999; pp. 4348-4355; vol. 121.

Rigby et al.; "Ferrocenes derived from cyclopenta[l]phenanthrene: dibenzindene-metal complexes that resist haptotropic shifts"; Journal of Organometallic Chemistry; 2001; pp. 372-381; vol. 637-639.

Weisse et al.; "Preparation of substituted indanones"; Document No. 120:244349, retrieved from CAPLUS, entered in STN on May 14, 1994.

* cited by examiner

CYCLOPENTA[B]FLUORENYL TRANSITION METAL COMPOUND, CATALYST COMPOSITION CONTAINING THE SAME, AND METHOD OF PREPARING ETHYLENE HOMOPOLYMER OR COPOLYMER OF ETHYLENE AND ALPHA-OLEFIN USING THE SAME

CROSS REFERENCE TO RELATED APPLICATIONS

This application is a divisional application of U.S. application Ser. No. 15/832,011, filed Dec. 5, 2017, which is a divisional application of U.S. application Ser. No. 14/789,512, filed Jul. 1, 2015, now U.S. Pat. No. 9,926,394, issued Mar. 27, 2018, which is a divisional application of U.S. application Ser. No. 13/881,098, filed Apr. 23, 2013, now U.S. Pat. No. 9,120,884, issued Sep. 1, 2015, which is a United States national phase application under 35 U.S.C. § 371 of International Application No. PCT/KR2012/004511 filed Jun. 8, 2012, and claims priority under 35 U.S.C. § 119(a)-(d) to Korean Patent Application Nos. 10-2012-0059441 filed on Jun. 1, 2012, and 10-2011-0055719, filed on Jun. 9, 2011 in the Korean Intellectual Property Office, the disclosures of which are incorporated herein by reference in their entirety.

BACKGROUND OF THE INVENTION

Field of the Invention

The present invention relates to a new transition metal compound based on cyclopenta[b]fluorenyl group, a transition metal catalyst composition containing the same and having high catalytic activity for preparing an ethylene homopolymer or a copolymer of ethylene and one α-olefin, a method of preparing an ethylene homopolymer or a copolymer of ethylene and α-olefin using the same, and the prepared ethylene homopolymer or the copolymer of ethylene and α-olefin. More particularly, the present invention relates to a transition metal compound that is advantageous in obtaining high-efficiency and high-molecular weight ethylene-based polymers by having a structure where a Group 4 transition metal in the Periodic Table of Elements as a core metal is linked with a cyclopenta[b]fluorenyl group that has a rigid plane structure even though it is not in a hetero ring; has abundant electrons widely non-localized; and allows a substituent contributing to improvement in solubility and performance to be easily inducible at position 9 thereof, via an amido group substituted with a silyl group, a transition metal catalyst composition containing the transition metal compound as a primary catalyst and an aluminum compound, a boron compound, or a mixture thereof as cocatalyst, for preparing an ethylene homopolymer or a copolymer of ethylene and at least one α-olefin, a method of preparing an ethylene homopolymer or a copolymer of ethylene and α-olefin using the same, and the prepared ethylene homopolymer or the copolymer of ethylene and α-olefin.

Description of Related Art

In the prior art, so-called Ziegler-Natta catalyst consisting of a titanium or vanadium compound as a primary catalyst component and an alkylaluminum compound as cocatalyst component have been generally used for preparing ethylene homopolymers or copolymers of ethylene and α-olefin. Although a Ziegler-Natta catalytic system exhibits high activity on ethylene polymerization, the catalytic system has disadvantages in that molecular weight distribution of the produced polymer is broad due to non-uniform catalyst activation point, and especially, composition distribution thereof is not uniform in the copolymers of ethylene and α-olefin.

Recently, so-called metallocene catalytic systems consisting of a metallocene compound of Group 4 transition metal in the Periodic Table of Elements, such as titanium, zirconium and hafnium, and methylaluminoxane as a cocatalyst have been developed. The metallocene catalytic system is a homogeneous catalyst having a mono-modal catalyst activation point, and thus, can provide prepare polyethylene having narrower molecular weight distribution and more homogenous composition distribution as compared with the existing Ziegler-Natta catalyst system. For example, European Patent Laid-Open Publication Nos. 320,762 and 372,632; Japanese Patent Laid-Open Publication Nos. Sho 63-092621, Hei 02-84405 and Hei 03-2347 reported that ethylene may be polymerized with high activity by activating metallocene compounds such as $Cp_2TiCl_2$, $Cp_2ZrCl_2$, $Cp_2ZrMeCl$, $Cp_2ZrMe_2$, ethylene$(IndH_4)_2ZrCl_2$ by using methylaluminoxane as a cocatalyst, to prepare polyethylene having a molecular weight distribution (Mw/Mn) in the range from 1.5 to 2.0. However, it is difficult to obtain high-molecular weight polymers by using the above catalytic system, and further, when solution polymerization executed at a high temperature of 100° C. or higher is employed, polymerizing activity abruptly decreases and β-dehydrogenation is predominant. Therefore, the system has been known to be not suitable for preparing high-molecular weight polymers having a weight average molecular weight (Mw) of 100,000 or more.

Meanwhile, there was reported so-called geo-restrictive non-metallocene based catalysts (also referred to as single activation point catalysts) where the transition metals are linked in a ring type, as catalysts for preparing high-molecular weight polymers with high catalytic activity in ethylene homopolymerization or copolymerization of ethylene and α-olefin in the solution polymerization conditions. European Patent Nos. 0416815 and 0420436 suggest an example where amide group is linked to one cyclopentadiene ligand in a ring type, and European Patent No. 0842939 shows an example of the catalyst where phenol-based ligand as an electron donor compound is linked to cyclopentadiene ligand in a ring type. This geo-restrictive catalyst may remarkably improve reactivity with higher α-olefins due to lowered sterical hindrance effect of the catalyst itself, but has many difficulties in the commercial use thereof. Therefore, it has been important to secure more competitive cataltytic systems in requiring commercialized catalysts based on economical feasibility, that is, excellent high-temperature activity, excellent reactivity with higher α-olefins, and capability to prepare high-molecular weight polymers.

SUMMARY OF THE INVENTION

In order to overcome the problems of the prior art, the present inventors conducted extensive studies, and found that a transition metal compound having a structure where a Group 4 transition metal in the Periodic Table of Elements as a core metal is linked with a cyclopenta[b]fluorenyl group that has a rigid plane structure even though it is not in a hetero ring; has abundant electrons widely non-localized; and allows a substituent contributing to improvement in solubility and performance to be easily inducible at position 9 thereof, via an amido group substituted with a silyl group was advantageous in obtaining high-efficiency and high-molecular weight polymers in polymerization of ethylene and olefins, and thus, completed the present invention.

An object of the present invention is to provide a transition metal compound useful as a catalyst for preparing ethylene homopolymers or copolymers of ethylene and α-olefin, and provide a catalyst composition containing the same.

Another object of the present invention is to provide a method of economically preparing ethylene homopolymers or copolymers of ethylene and α-olefin using the catalyst composition containing the transition metal compound in a view of commertialization.

Still another object of the present invention is to provide ethylene-based polymers selected from the ethylene homopolymers and the copolymers of ethylene and α-olefin prepared by the above method.

DESCRIPTION OF THE INVENTION

An aspect of the present invention for achieving the above objects provides a new transition metal compound based on a cyclopenta[b]fluorenyl group represented by Chemical Formula 1 below. More specifically, the present invention relates to a transition metal compound that is advantageous in obtaining high-efficiency and high-molecular weight ethylene-based polymers by having a structure where a Group 4 transition metal in the Periodic Table of Elements as a core metal is linked with a cyclopenta[b]fluorenyl group that has a rigid plane structure even though it is not in a hetero ring; has abundant electrons widely non-localized; and allows a substituent contributing to improvement in solubility and performance to be easily inducible at position 9 thereof, via an amido group substituted with a silyl group.

[Chemical Formula 1]

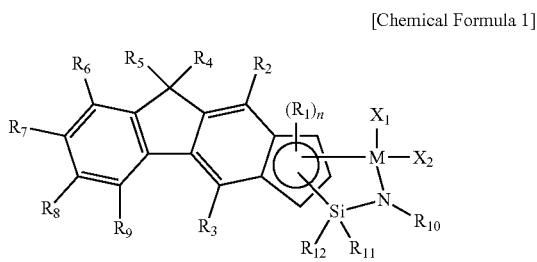

In Chemical Formula 1, M is a Group 4 transition metal in the Periodic Table of Elements;

n is an integer of 1 or 2, each $R_1$ may be the same or different when n is 2;

$R_1$ is hydrogen, (C1-C50)alkyl, halo(C1-C50)alkyl, (C3-C50)cycloalkyl, (C6-C30)aryl, (C6-C30)aryl(C1-C50)alkyl, ((C1-C50)alkyl(C6-C30)aryl)(C1-C50)alkyl, —$NR^aR^b$, —$SiR^cR^dR^e$, or 5- through 7-membered N-heterocycloalkyl containing at least one nitrogen atom;

$R_2$ and $R_3$ each are independently hydrogen, (C1-C50)alkyl, (C1-C50)alkoxy, halo(C1-C50)alkyl, (C3-C50)cycloalkyl, (C6-C30)aryl, (C6-C30)aryloxy, (C1-C50)alkyl(C6-C30)aryloxy, (C6-C30)aryl(C1-C50)alkyl, ((C1-C50)alkyl(C6-C30)aryl)C1-C50)alkyl, —$NR^aR^b$ or —$SiR^cR^dR^e$;

$R_4$, $R_5$, $R_{10}$, $R_{11}$ and $R_{12}$ each are independently (C1-C50)alkyl, halo(C1-C50)alkyl, (C3-C50)cycloalkyl, (C6-C30)aryl, (C6-C30)aryl(C1-C50)alkyl, ((C1-C50)alkyl(C6-C30)aryl)(C1-C50)alkyl, —$NR^aR^b$, or —$SiR^cR^dR^e$, and $R_{11}$ and $R_{12}$ may be linked via (C4-C7)alkylene to form a ring;

$R_6$, $R_7$, $R_8$ and $R_9$ each are independently hydrogen, (C1-C50)alkyl, halo(C1-C50)alkyl, (C3-C50)cycloalkyl, (C1-C50)alkoxy, (C6-C30)aryl, (C6-C30)aryl(C1-C50)alkyl, ((C1-C50)alkyl(C6-C30)aryl)(C1-C50)alkyl, (C6-C30)aryloxy, (C1-C50)alkyl(C6-C30)aryloxy, N-carbazolyl, —$NR^aR^b$, or —$SiR^cR^dR^e$, or may be linked to an adjacent substituent via (C1-C5)alkylene to form a ring, and at least one —$CH_2$— of the alkylene may be substituted by a hetero atom selected from —O—, —S—, and —NR'—, and the alkylene may be further substituted with (C1-C50)alkyl;

aryl of $R_1$ to $R_{12}$ may be further substituted with at least one substituent selected from the group consisting of (C1-C50)alkyl, halo(C1-C50)alkyl, (C1-C50)alkoxy, (C6-C30)aryloxy, (C6-C30)aryl, (C1-C50)alkyl(C6-C30)aryl, and (C6-C30)aryl(C1-C50)alkyl;

R' and $R^a$ to $R^e$ each are independently (C1-C50)alkyl or (C6-C30)aryl; and $X_1$ and $X_2$ each are independently halogen, (C1-C50)alkyl, (C2-C50)alkenyl, (C3-C50)cycloalkyl, (C6-C30)aryl, (C6-C30)aryl(C1-C50)alkyl, ((C1-C50)alkyl(C6-C30)aryl)(C1-C50)alkyl, (C1-C50)alkoxy, (C6-C30)aryloxy, (C1-C50)alkyl(C6-C30)aryloxy, (C1-C50)alkoxy(C6-C30)aryloxy, (C1-C50)alkylidene, or an anion or dianion ligand consisting of 60 or less atoms containing N, P, O, S, Si, and halogen, except hydrogen, provided that one of $X_1$ and $X_2$ is a dianion ligand, the other is ignored.

An example of the new transition metal compound based on the cyclopenta[b]fluorenyl group represented by Chemical Formula 1 above may include a transition metal compound represented by Chemical Formula 2 or 3 below:

[Chemical Formula 2]

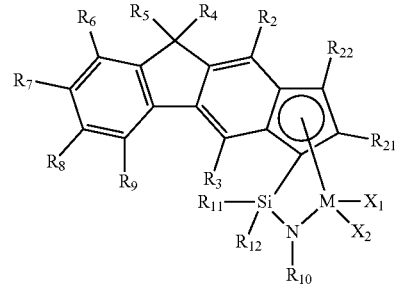

[Chemical Formula 3]

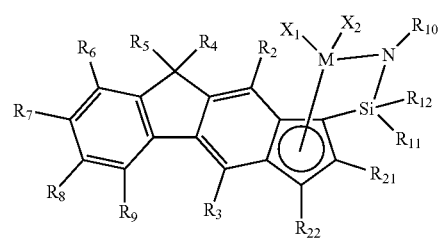

In Chemical Formulas 2 and 3, M, $R_2$ to $R_{12}$, $X_1$ and $X_2$ has the same definition in Chemical Formula 1; $R_{21}$ and $R_{22}$ each are independently hydrogen, (C1-C50)alkyl, halo(C1-C50)alkyl, (C3-C50)cycloalkyl, (C6-C30)aryl, (C6-C30)aryl(C1-C50)alkyl, ((C1-C50)alkyl(C6-C30)aryl)(C1-C50)alkyl, —$NR^aR^b$, —$SiR^cR^dR^e$, or 5- through 7-membered N-heterocycloalkyl containing at least one nitrogen atom; aryl of $R_1$ may be further substituted with at least one substituent selected from the group consisting of halogen, (C1-C50)alkyl, halo(C1-C50)alkyl, (C1-C50)alkoxy, (C6-

C30)aryloxy, (C6-C30)aryl, (C1-C50)alkyl(C6-C30)aryl, and (C6-C30)aryl(C1-C50)alkyl; and $R^a$ to $R^e$ each are independently (C1-C50)alkyl or (C6-C30)aryl.

Another aspect of the present invention for achieving the objects of the present invention provides a transition metal catalyst composition containing the transition metal compound, and a cocatalyst selected from an aluminum compound, a boron compound, or a mixture thereof.

Still another aspect of the present invention for achieving the objects of the present invention provides a method of preparing an ethylene-based polymer selected from an ethylene homopolymer and a copolymer of ethylene and α-olefin by using the transition metal compound or the transition metal catalyst composition, and the prepared ethylene homopolymer or copolymer of ethylene and α-olefin.

Hereinafter, the present invention will be described in more detail.

The Group 4 transition metal in the Periodic Table of Elements, M, is preferably titanium (Ti), zirconium (Zr), or hafnium (Hf).

The term "alkyl" described herein includes a straight chain type or a branched chain type.

The term "aryl" described herein is an organic radical derived from aromatic hydrocarbon by the removal of one hydrogen atom, and may include a single ring or a fused ring containing, properly 4 to 7 ring atoms, and preferably 5 or 6 ring atoms. Specific examples thereof include phenyl, naphthyl, biphenyl, anthryl, fluorenyl, phenanthryl, triphenyl, pyrenyl, perylenyl, chrysenyl, naphthacenyl, fluoranthenyl, or the like, but are not limited thereto.

For example, (C1-C50)alkyl may be methyl, ethyl, n-propyl, isopropyl, n-butyl, isobutyl, sec-butyl, tert-butyl, n-pentyl, neopentyl, amyl, n-hexyl, n-octyl, n-decyl, n-dodecyl, n-tetradecyl, n-hexadecyl, n-pentadecyl, n-octadecyl, n-icosyl, or n-docosyl; (C3-C50)cycloalkyl may be, for example, cyclopropyl, cyclobutyl, cyclopentyl, cyclohexyl, cycloheptyl, cyclooctyl, cyclodecyl, or cyclododecyl; (C6-C30)aryl or (C1-C50)alkyl(C6-C30)aryl may be, for example, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl, or anthracenyl; (C6-C30)aryl(C1-C50)alkyl or ((C1-C50)alkyl(C6-C30)aryl)(C1-C50)alkyl may be, for example, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl, or anthracenylmethyl;

and (C1-C50)alkoxy may be, for example, methoxy, ethoxy, n-propoxy, isopropoxy, n-butoxy, sec-butoxy, tert-butoxy, n-pentyloxy, neopentyloxy, n-hexyloxy, n-octyloxy, n-dodecyloxy, n-pentadecyloxy, or n-eicosyloxy.

Preferably, each $R_1$ is independently hydrogen, methyl, ethyl, n-propyl, isopropyl, n-butyl, phenyl, naphthyl, biphenyl, 2-isopropylphenyl, 3,5-xylyl, 2,4,6-trimethylphenyl, benzyl, dimethylamino, or pyrrolidino;

preferably, $R_2$ and $R_3$ are independently hydrogen, methyl, ethyl, n-propyl, isopropyl, n-butyl, phenyl, naphthyl, biphenyl, 2-isopropylphenyl, 3,5-xylyl, 2,4,6-trimethylphenyl, benzyl, methoxy, ethoxy, isopropoxy, phenoxy, 4-tert-butylphenoxy, or naphthoxy;

preferably, $R_4$ and $R_5$ each are independently methyl, ethyl, n-propyl, isopropyl, n-butyl, isobutyl, 2-methylbutyl, sec-butyl, tert-butyl, n-pentyl, neopentyl, amyl, n-hexyl, n-octyl, n-decyl, n-dodecyl, n-tetradecyl, n-hexadecyl, n-pentadecyl, n-octadecyl, n-icosyl, n-docosyl, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl, anthracenyl, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-prop ylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl, anthracenylmethyl, 4-methoxyphenyl, 3,4-dimethoxyphenyl, or 4-(hexyloxy)-3,5-dimethylphenyl;

preferably, $R_6$ to $R_9$ each are independently hydrogen, methyl, ethyl, n-propyl, isopropyl, n-butyl, isobutyl, 2-methylbutyl, sec-butyl, tert-butyl, n-pentyl, neopentyl, amyl, n-hexyl, n-octyl, n-decyl, n-dodecyl, n-pentadecyl, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, 2,7-di-tert-butyl-9-p-tolyl-9H-fluoren-9-yl, triphenyl, naphthyl, anthracenyl, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)

methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl, anthracenylmethyl, 4-methoxyphenyl, 3,4-dimethoxyphenyl, methoxy, ethoxy, isopropoxy, n-butoxy, n-hexyloxy, 2-methylbutyl, phenoxy, 4-tert-butylphenoxy, naphthoxy, trimethylsilyl, triphenylsilyl, dimethylamino, diphenylamino, or 9H-carbazol-9-yl, or may be linked to an adjacent substitutent via

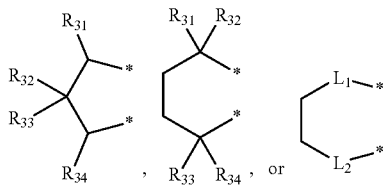

to form a ring, $L_1$ and $L_2$ each are independently —O—, —S—, or —NR'— [each R' is independently (C1-C50)alkyl or (C6-C30)aryl], $R_{31}$ to $R_{34}$ each, independently, have the same definition as $R_4$ and $R_5$, and more preferably, hydrogen, methyl or n-tetradecyl;

preferably, $R_{11}$ and $R_{12}$ each are independently methyl, ethyl, n-propyl, isopropyl, n-butyl, isobutyl, 2-methylbutyl, sec-butyl, tert-butyl, n-pentyl, neopentyl, amyl, n-hexyl, n-octyl, n-decyl, n-dodecyl, n-pentadecyl, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl, anthracenyl, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-tetradecylphenyl)methyl, naphthylmethyl, anthracenylmethyl, 4-methoxyphenyl, or 3,4-dimethoxyphenyl, or $R_{11}$ and $R_{12}$ may be linked to each other via butylene or pentylene to form a ring;

$R_{10}$ is methyl, ethyl, n-propyl, isopropyl, n-butyl, isobutyl, 2-methylbutyl, sec-butyl, tert-butyl, n-pentyl, neopentyl, amyl, n-hexyl, n-octyl, n-decyl, n-dodecyl, n-pentadecyl, cyclohexyl, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl, anthracenyl, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl, anthracenylmethyl, 2-methoxyphenyl, or 3,4-dimethoxyphenyl.

In the definitions of substituents $X_1$ and $X_2$, examples of halogen atom may include fluorine, chlorine, bromine, and iodine atom; examples of (C1-C50)alkyl may include methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl, and n-eicosyl; examples of (C3-C50)cycloalkyl may include cyclopropyl, cyclobutyl, cyclopentyl, cyclohexyl, cycloheptyl, and adamantyl; examples of (C6-C30)aryl may include phenyl and naphthyl; examples of (C6-C30)aryl(C1-C50)alkyl or ((C1-C50)alkyl(C6-C30)aryl)(C1-C50)alkyl may include benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl, and anthracenylmethyl; examples of (C1-C50)alkoxy may include methoxy, ethoxy, n-propoxy, isopropoxy, n-butoxy, sec-butoxy, tert-butoxy, n-pentyloxy, neopentyloxy, n-hexyloxy, n-octyloxy, n-dodecyloxy, n-pentadecyloxy, and n-eicosyloxy; examples of (C6-C30)aryloxy may include phenoxy, 4-tert-butylphenoxy, or 4-methoxyphenoxy, the anion or dianion ligand consisting of 60 or less atoms containing N, P, O, S, Si, and halogen, except for hydrogen may be —OSiR$^f$R$^g$R$^h$, —SR$^i$ [R$^f$ to R$^i$ each are independently (C1-C50)alkyl, (C6-C30)aryl, (C3-C50)cycloalkyl], —NR$^j$R$^k$, or —PR$^l$R$^m$ [R$^j$ to R$^m$ each are independently (C1-C50)alkyl, (C6-C30)aryl, (C6-C30)aryl(C1-C50)alkyl, (C3-C50)cycloalkyl, tri(C1-C50)

alkylsilyl, or tri(C6-C30)arylsilyl]. Examples of —OSiR^fR^gR^h may include trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyldimethylsiloxy, tri-n-pentylsiloxy, tri-n-hexylsiloxy, or tricyclohexylsiloxy; examples of —NR^jR^k may include dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bis(trimethylsilyl)amino, or bis(tert-butyldimethylsilyl)amino; examples of —PR^lR^m may include dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, dibenzylphosphine, methylethylphosphine, methylphenylphosphine, benzylhexylphosphine, bis(trimethylsilyl)phosphine, and bis-(tert-butyldimethylsilyl)phosphine; examples of —SR^i may include methylthio, ethylthio, propylthio, isopropylthio, butylthio, or isopentylthio.

$X_1$ and $X_2$ each are independently fluorine, chlorine, bromine, methyl, ethyl, isopropyl, amyl, benzyl, methoxy, ethoxy, isopropoxy, tert-butoxy, phenoxy, 4-tert-butylphenoxy, trimethylsiloxy, tert-butyldimethylsiloxy, dimethylamino, diphenylamino, dimethylphosphino, diethylphosphino, diphenylphosphino, ethylthio, or isopropylthio.

The transition metal compound of the present invention may be selected from compounds of the structures below, but is not limited thereto:

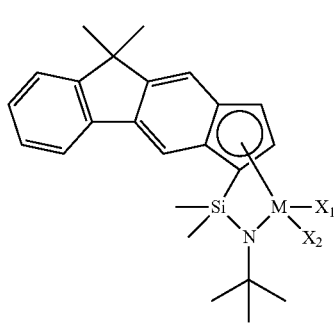

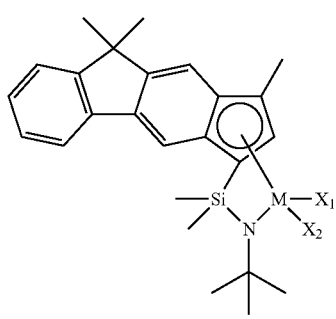

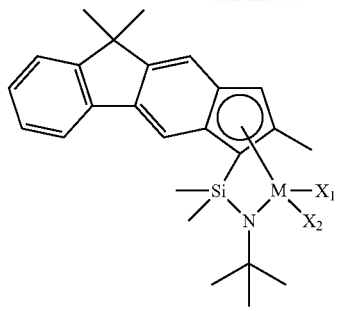

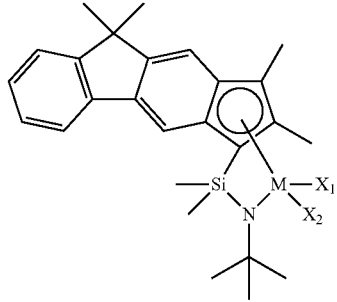

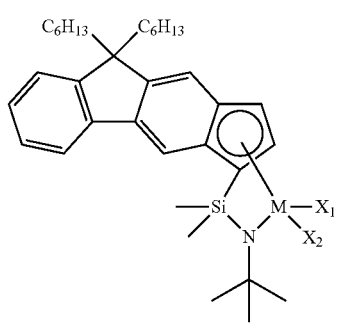

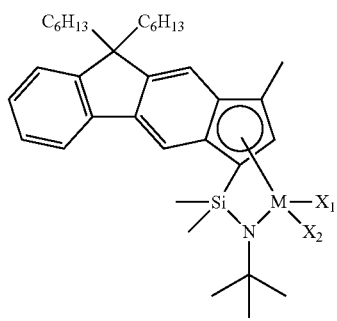

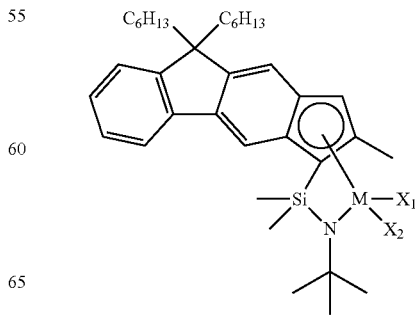

-continued
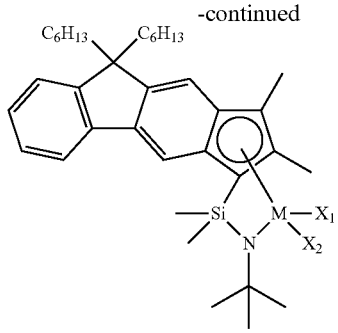
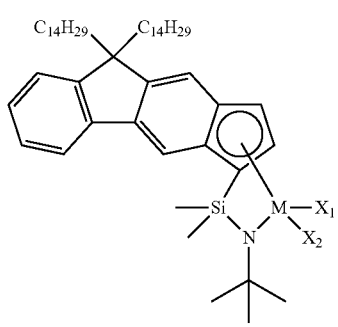
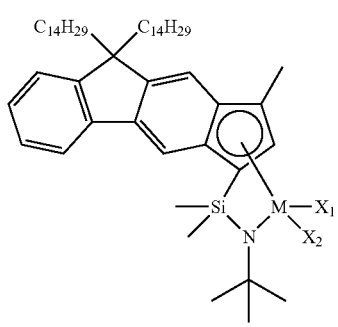
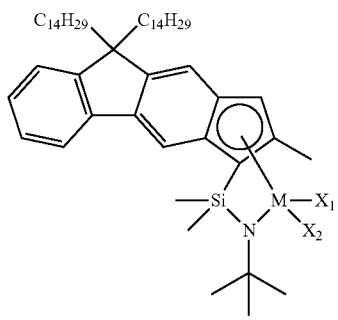
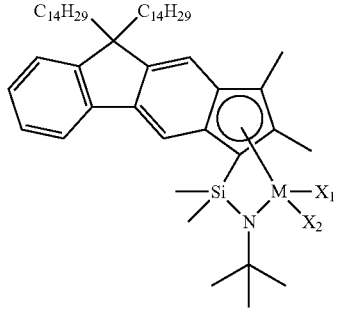
-continued
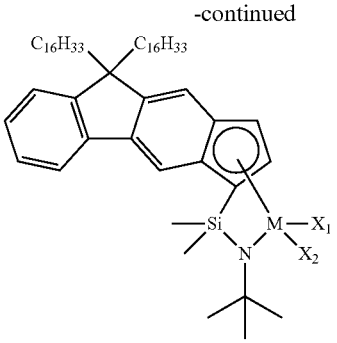
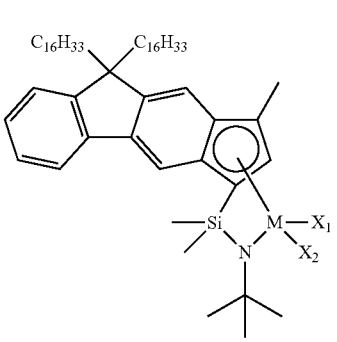
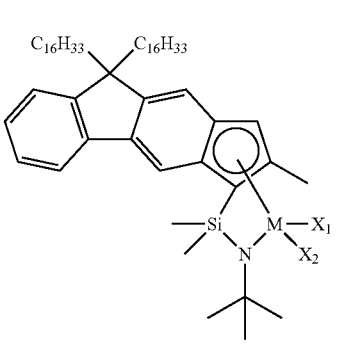
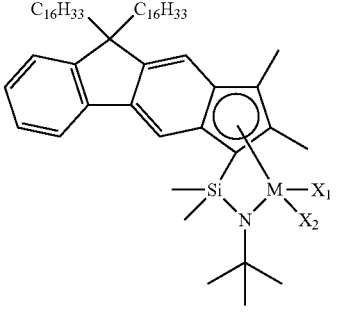
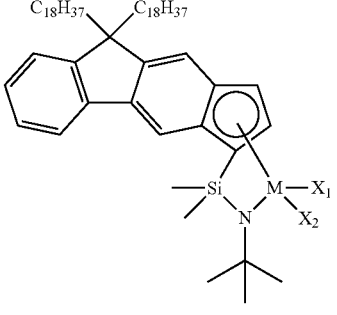

-continued
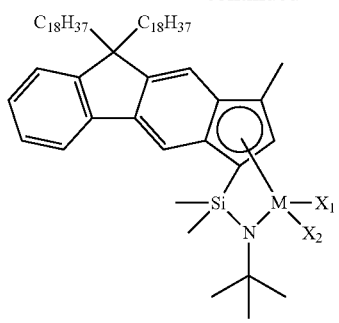
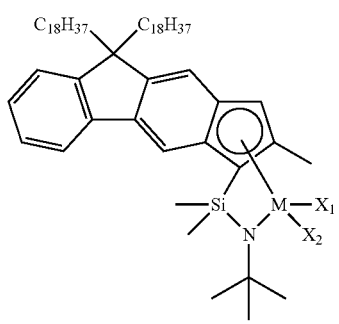
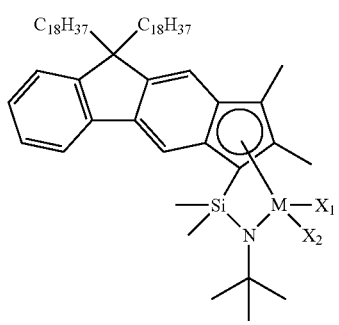
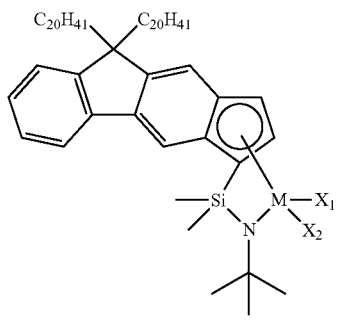
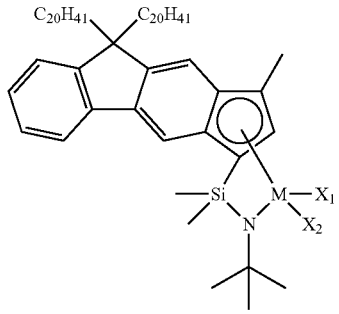
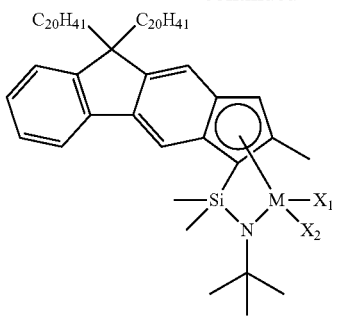
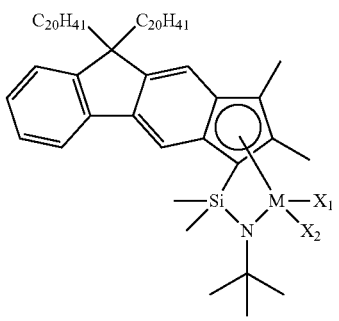
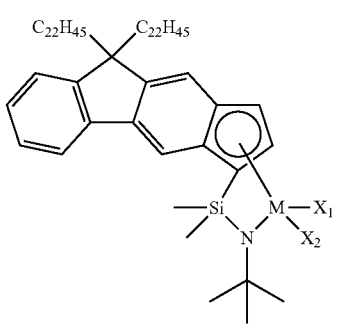
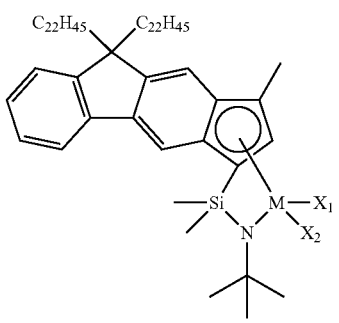
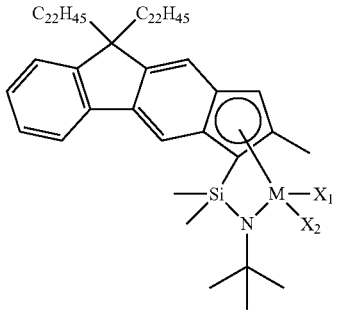

-continued
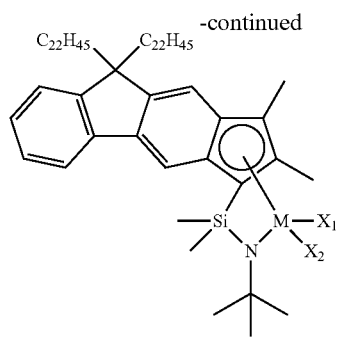
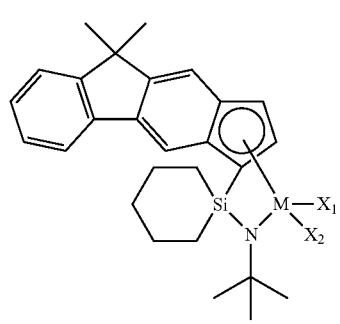
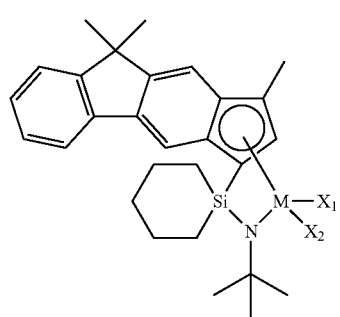
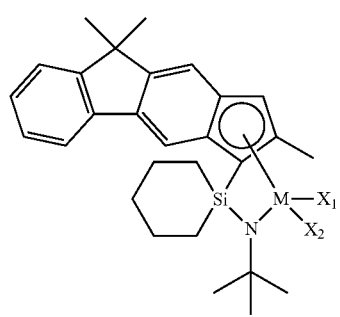
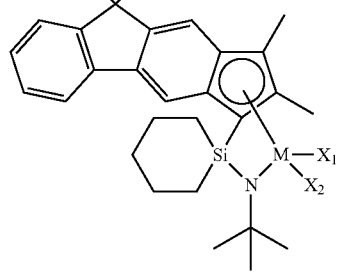
-continued
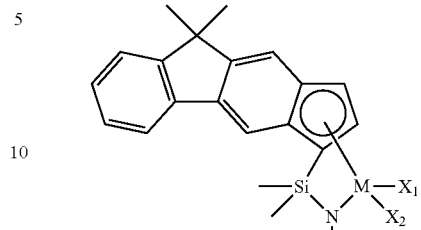
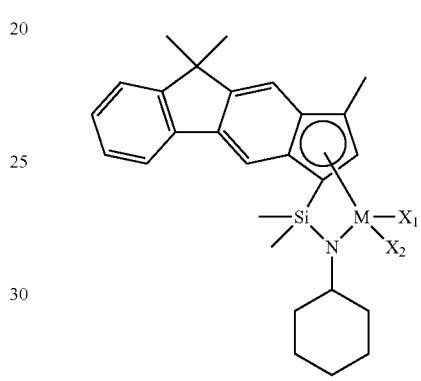
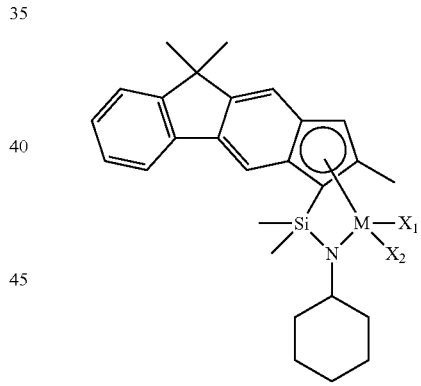
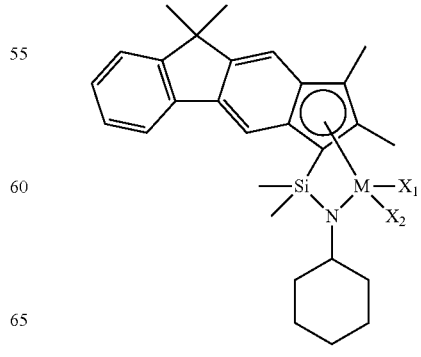
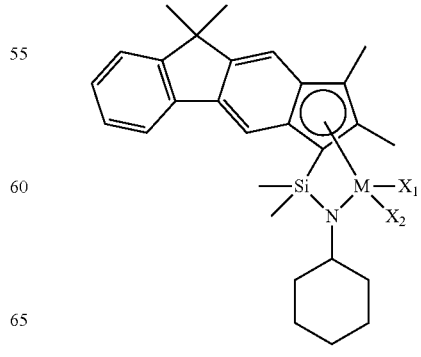

-continued
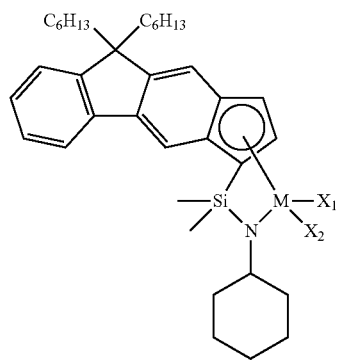
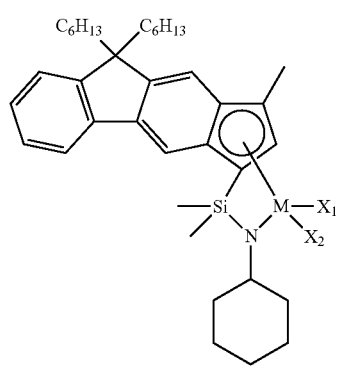
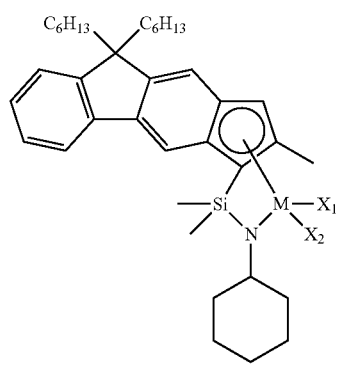
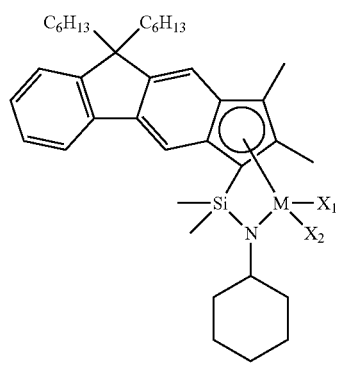
-continued
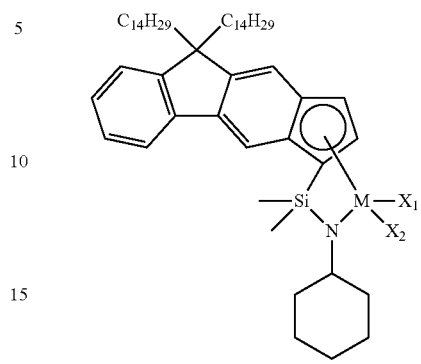
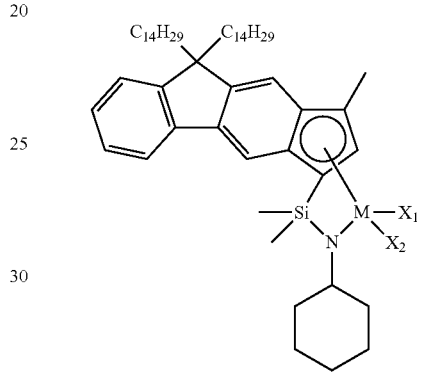
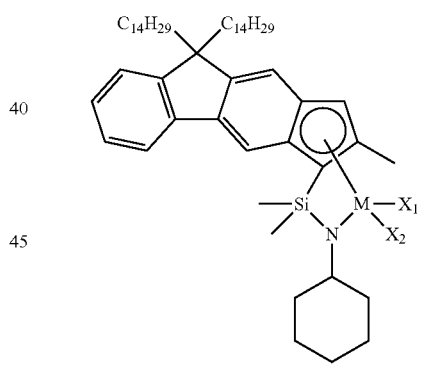
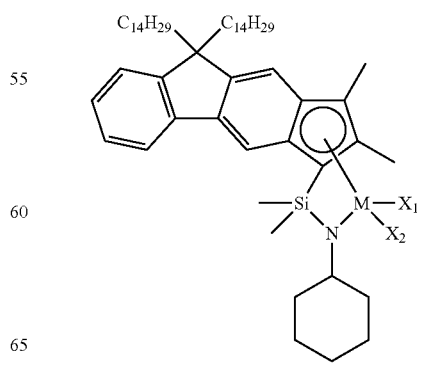

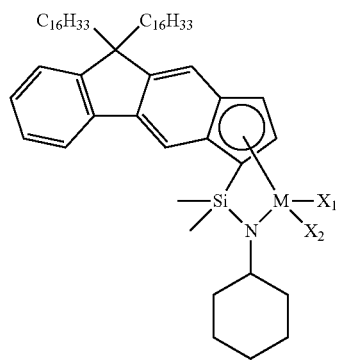
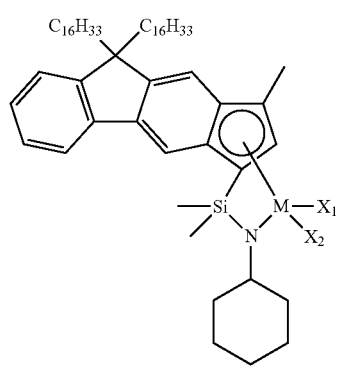
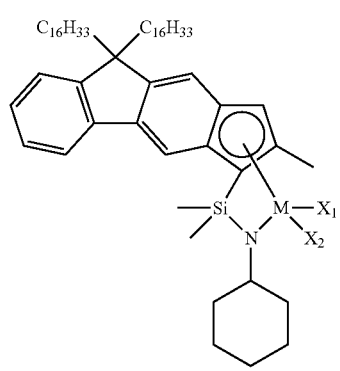
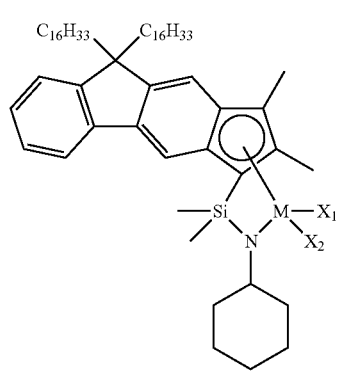
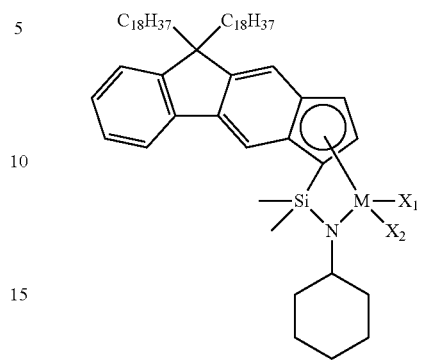
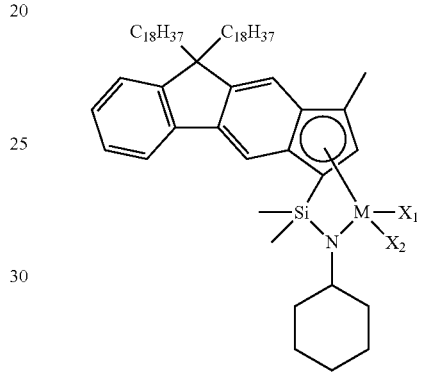
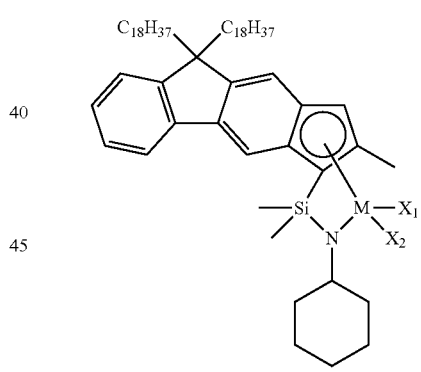
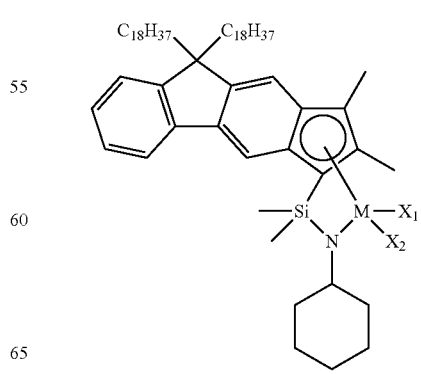

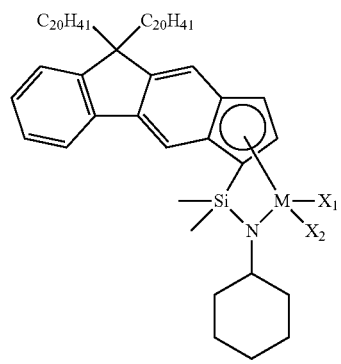
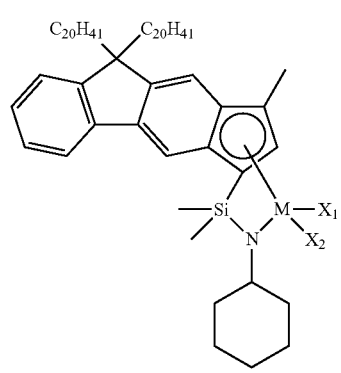
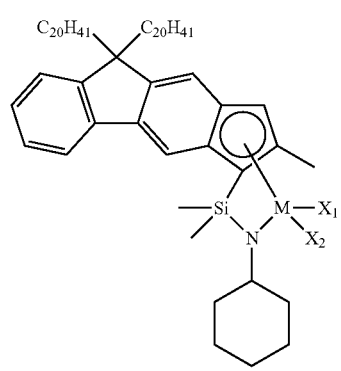
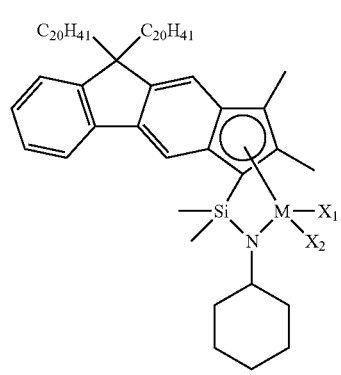
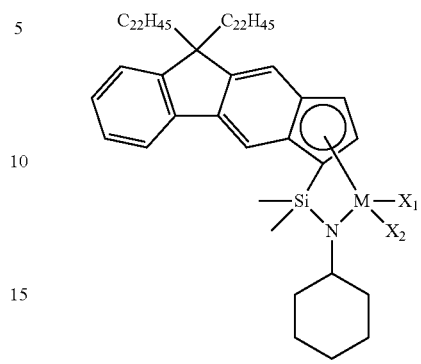
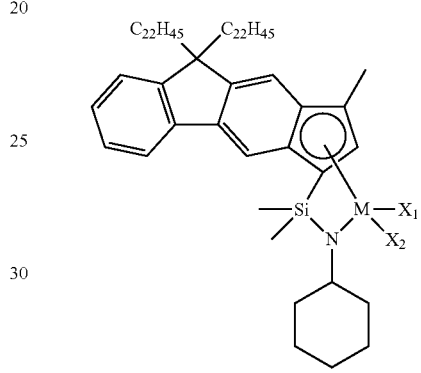
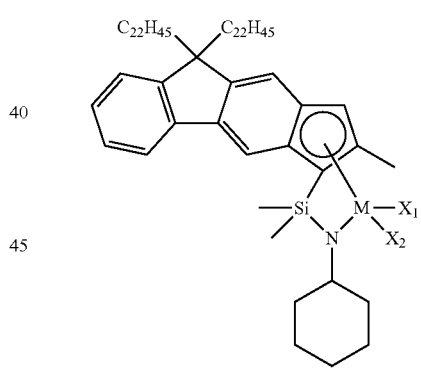
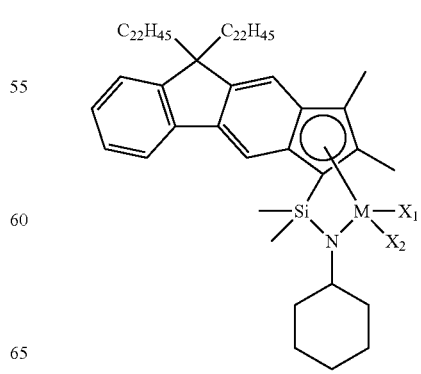

23
-continued
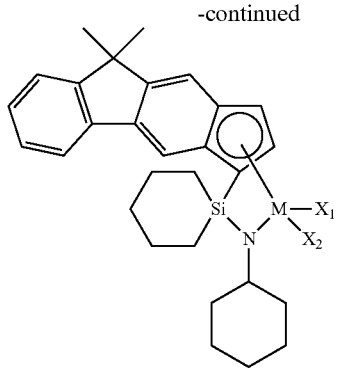
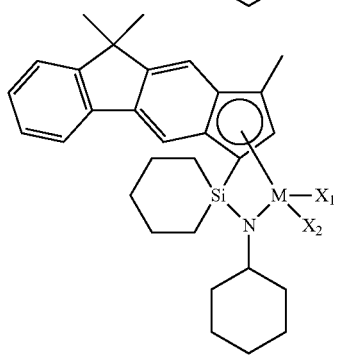
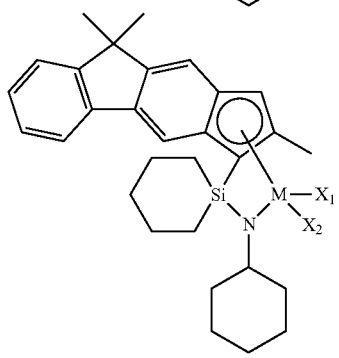
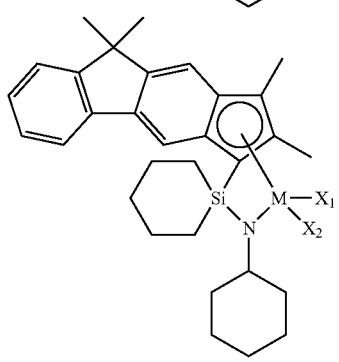
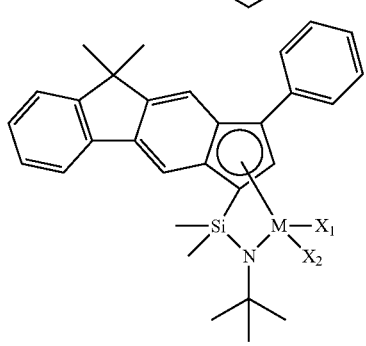
24
-continued
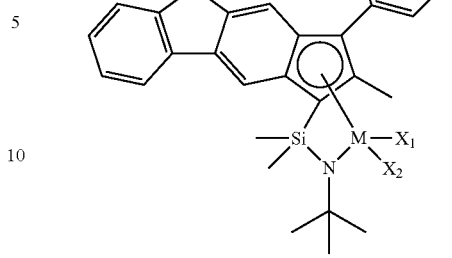
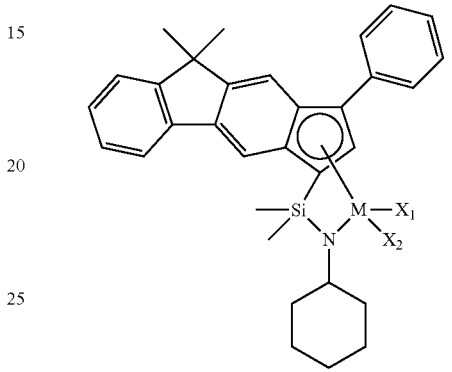
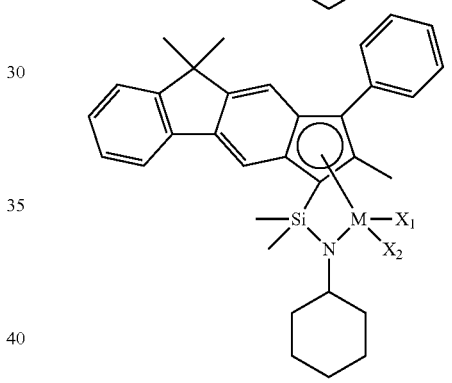
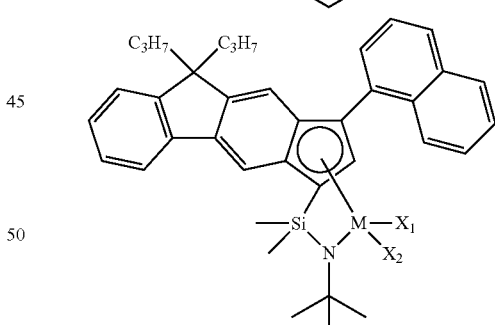
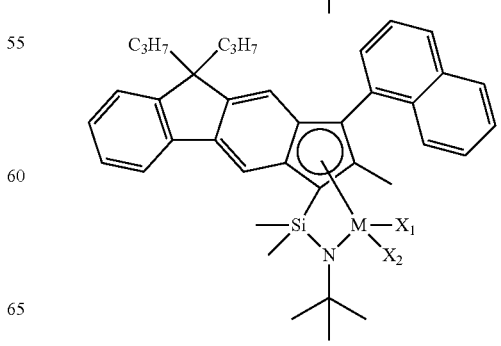

-continued
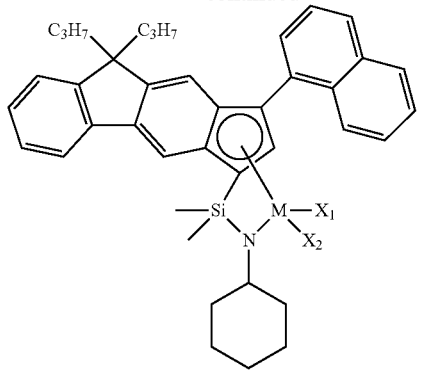
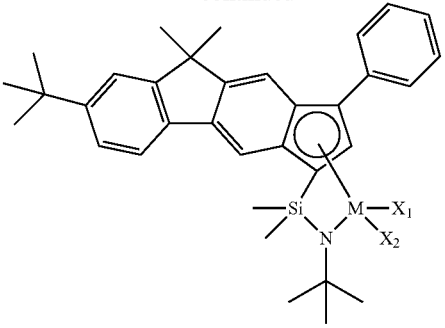
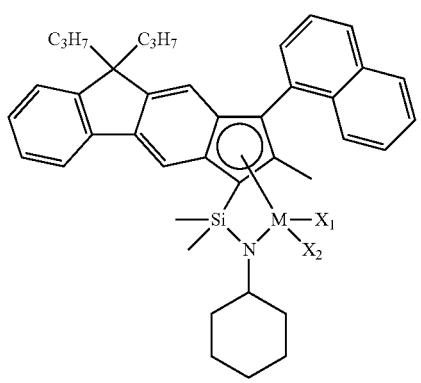
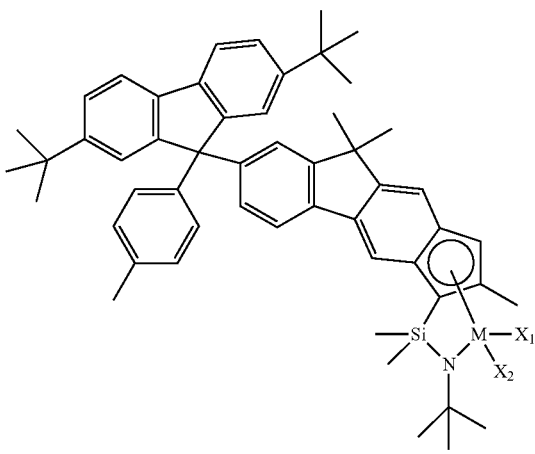
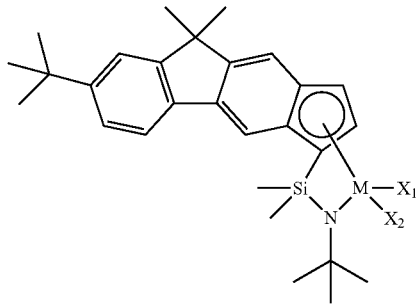
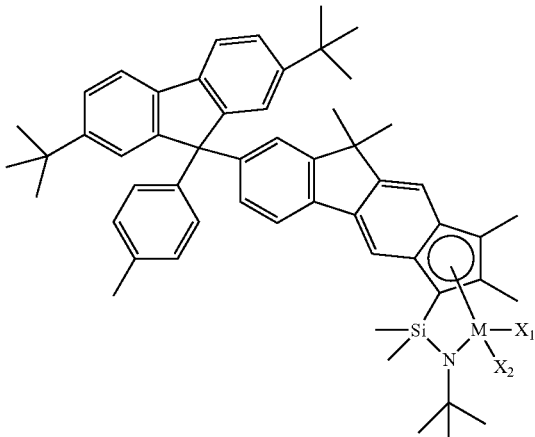
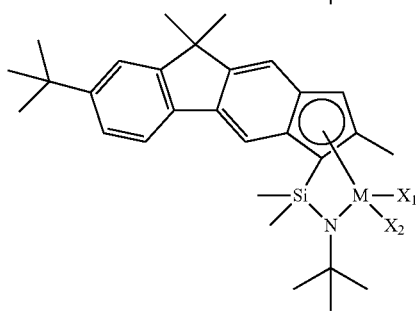
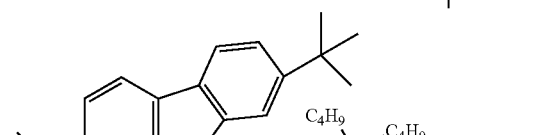
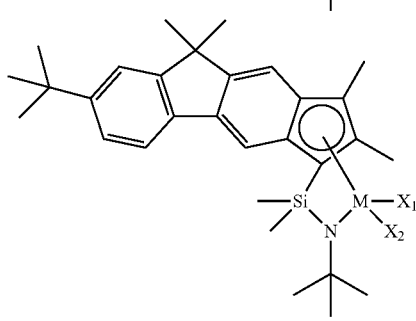
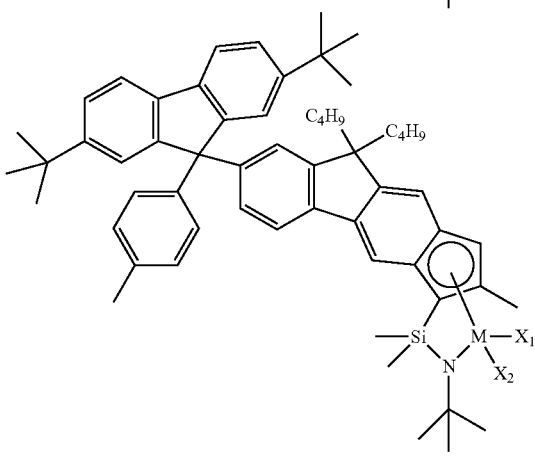

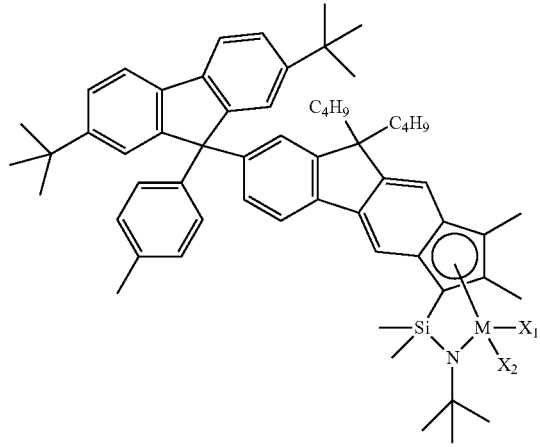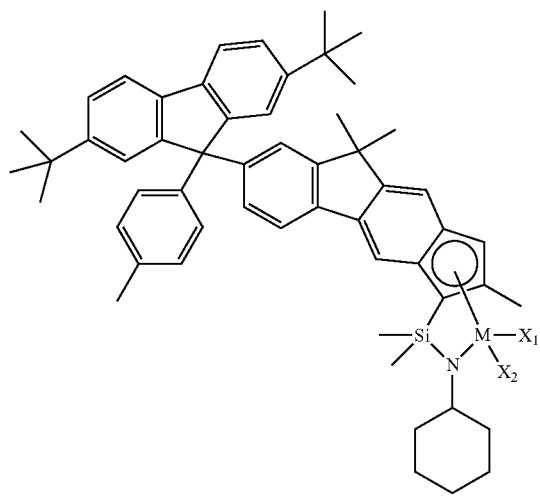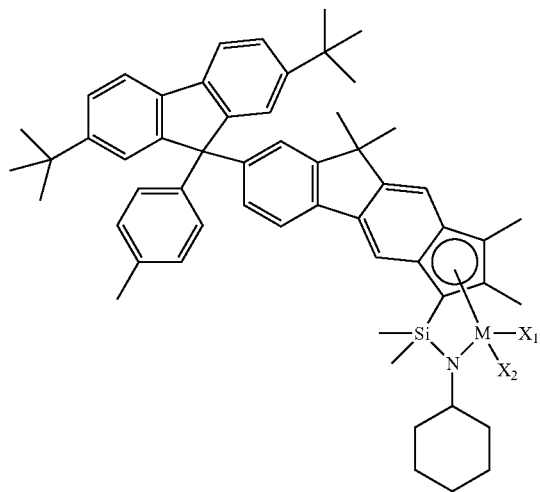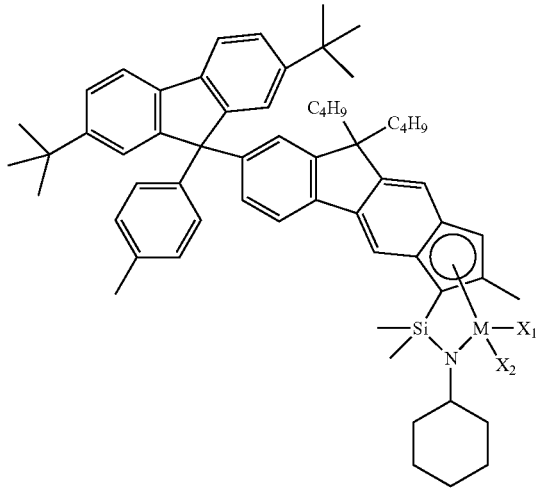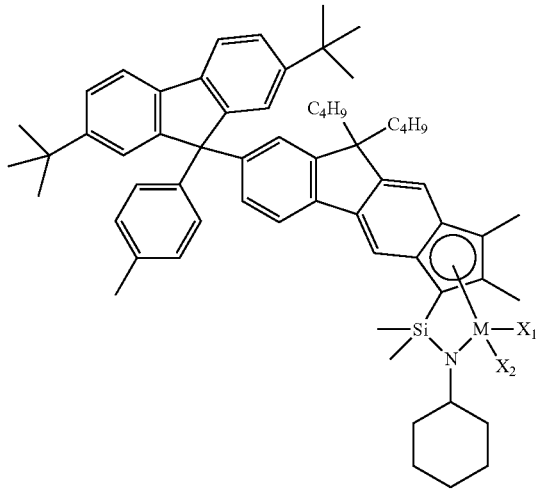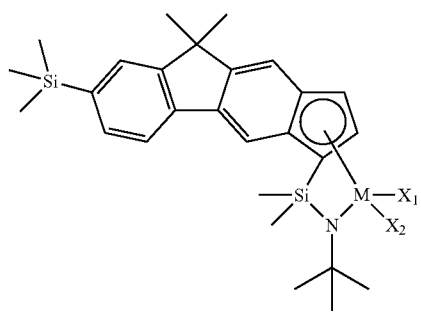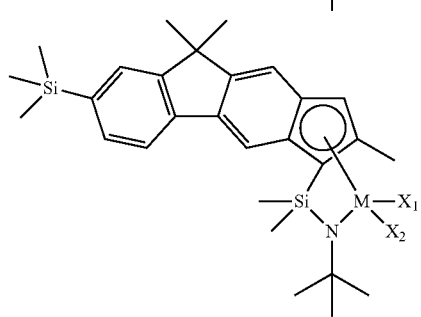

29
-continued
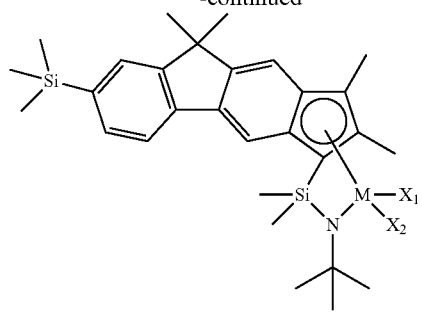
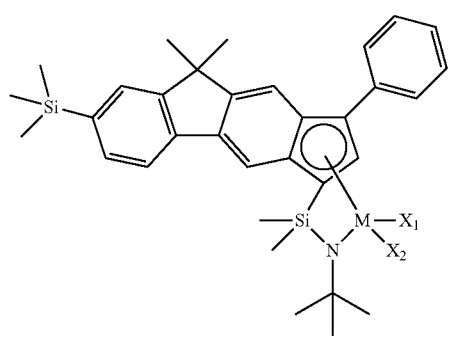
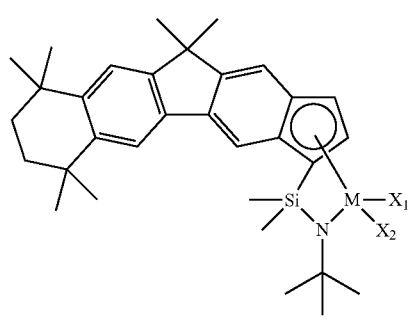
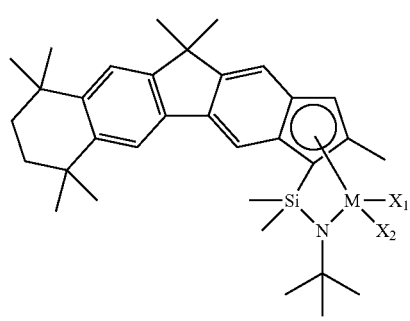
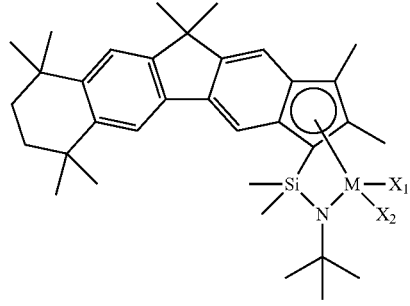
30
-continued
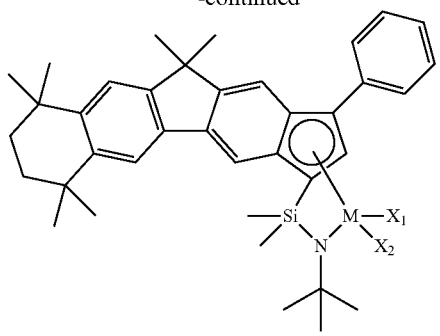
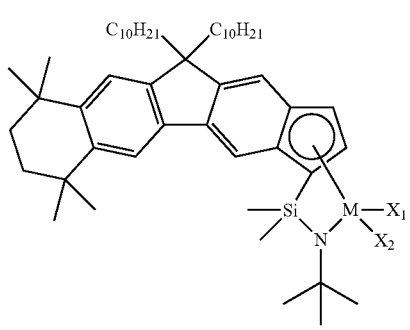
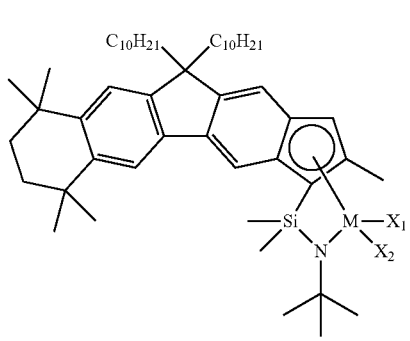
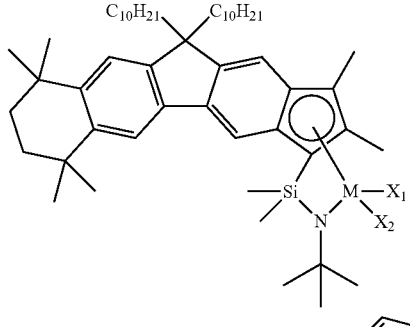
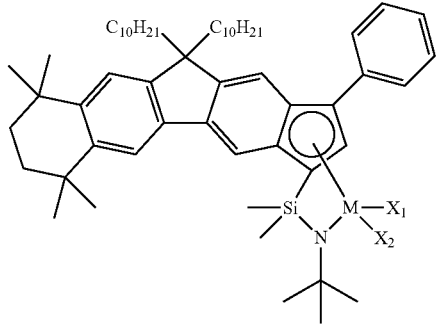

31
-continued
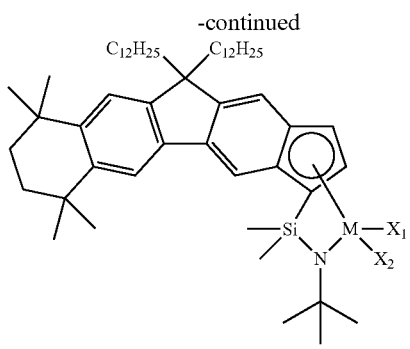
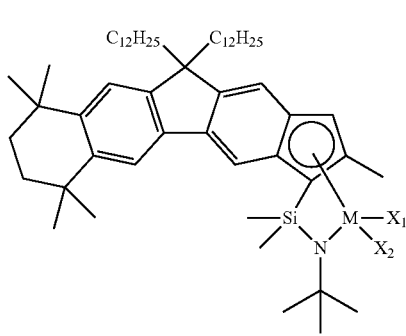
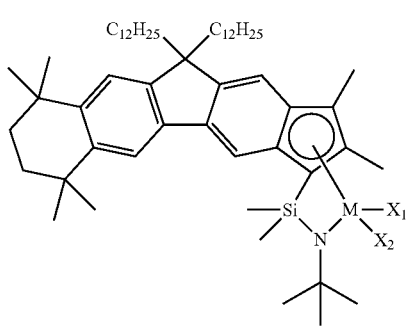
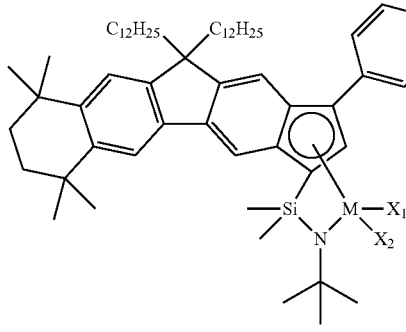
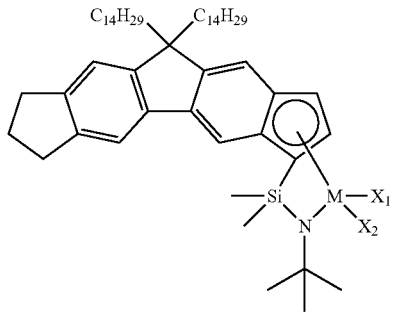
32
-continued
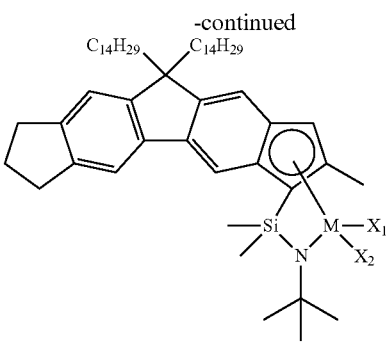
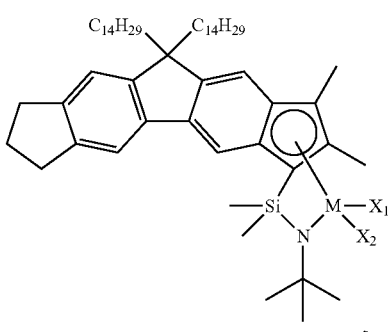
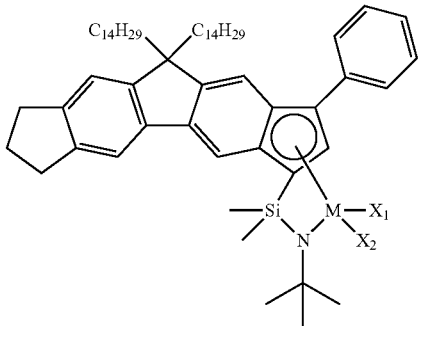
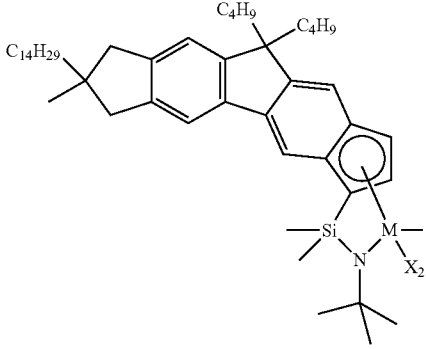
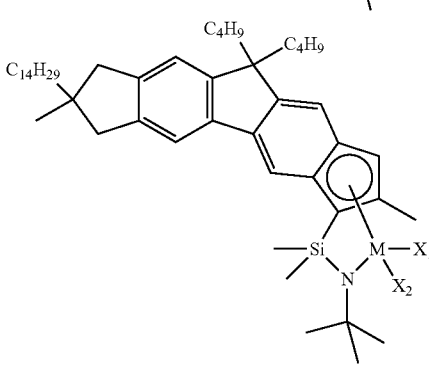

33
-continued
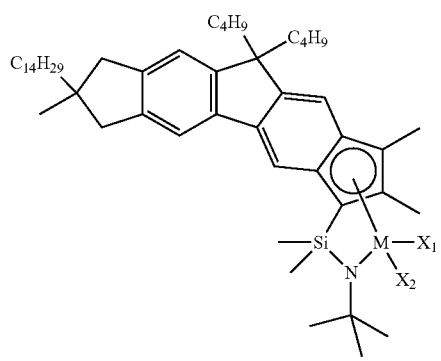
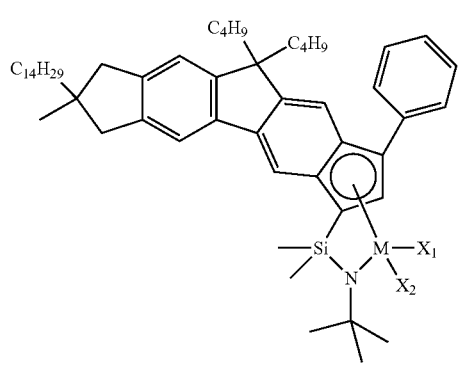
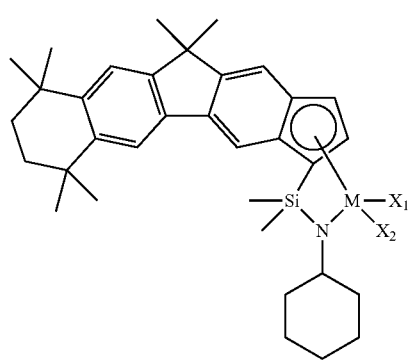
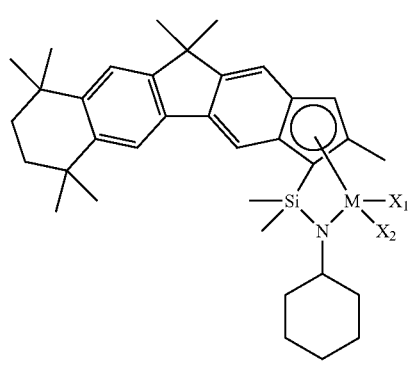
34
-continued
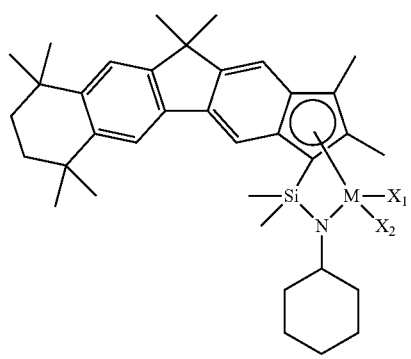
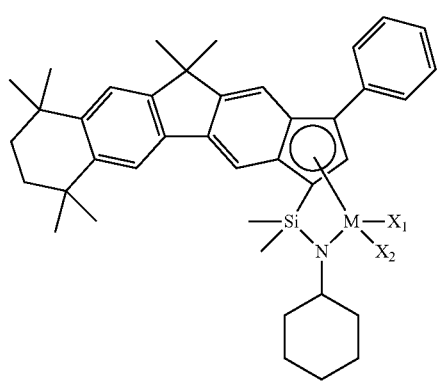
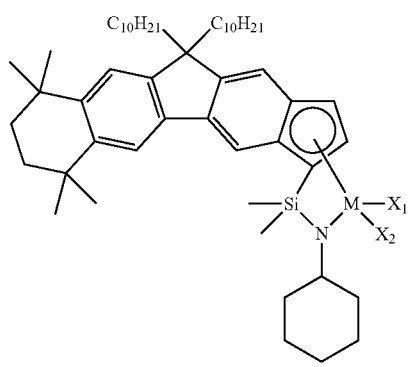
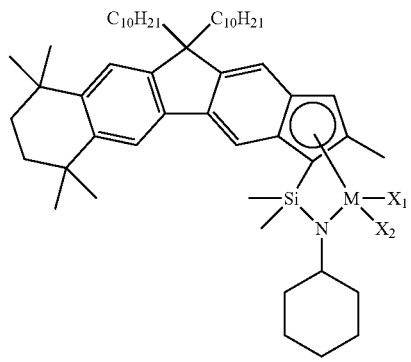

-continued
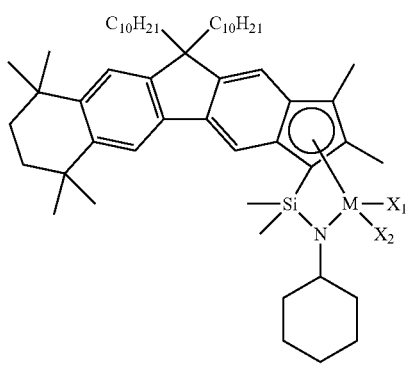
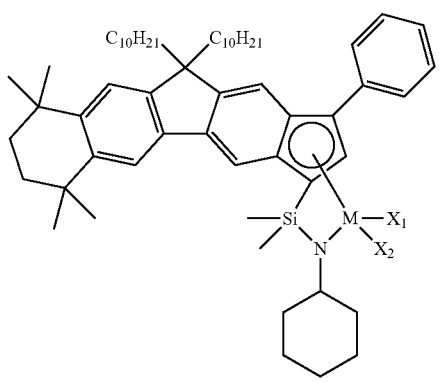
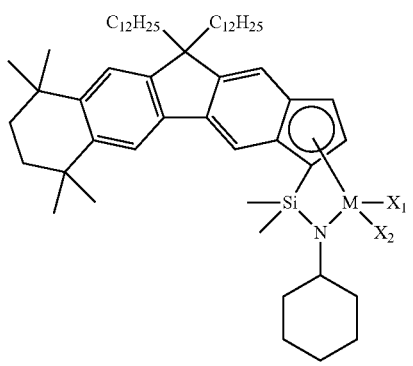
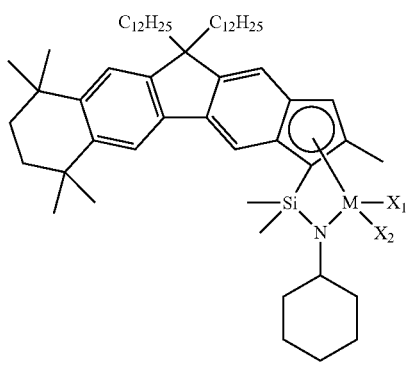
-continued
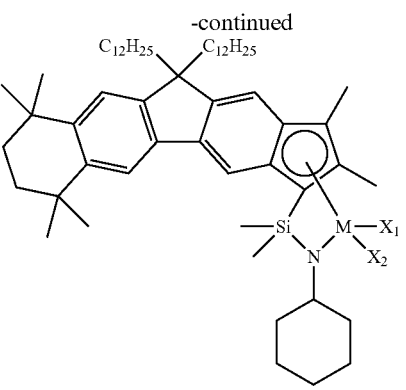
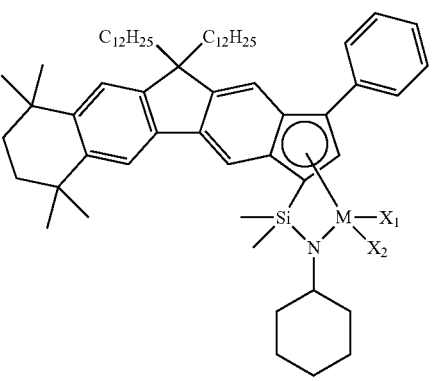
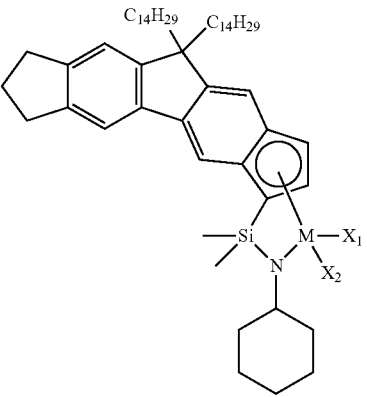
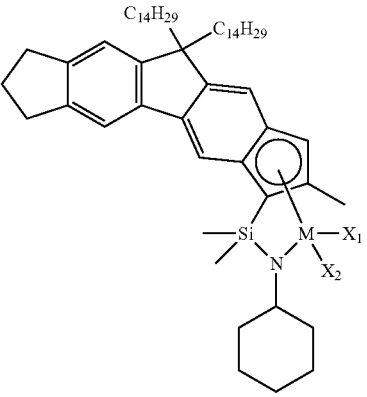

-continued
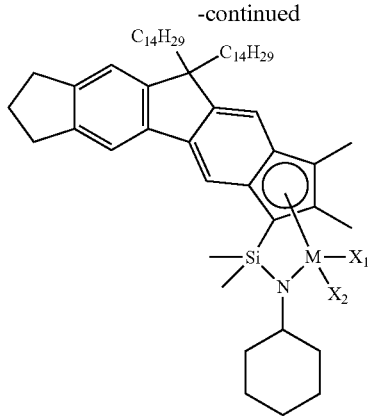
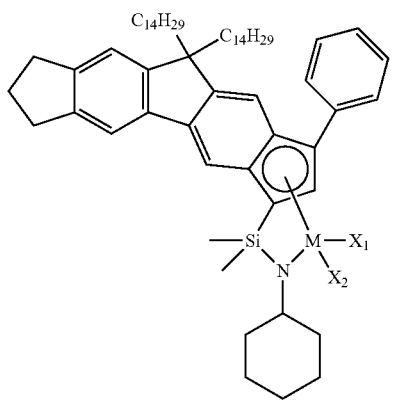
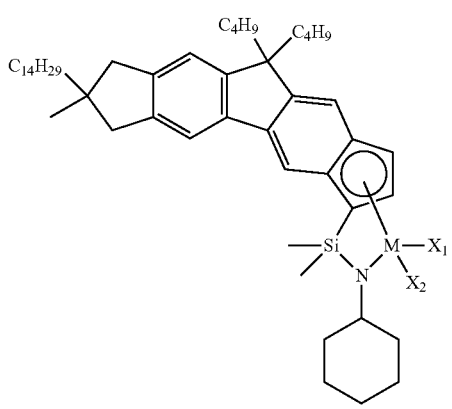
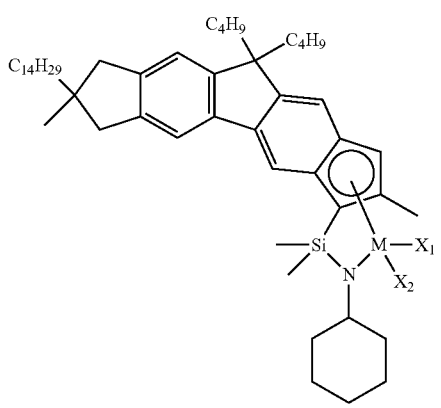
-continued
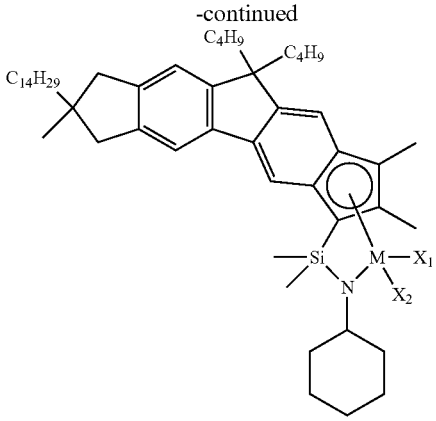
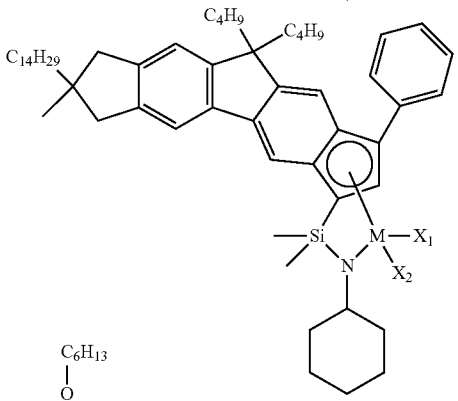
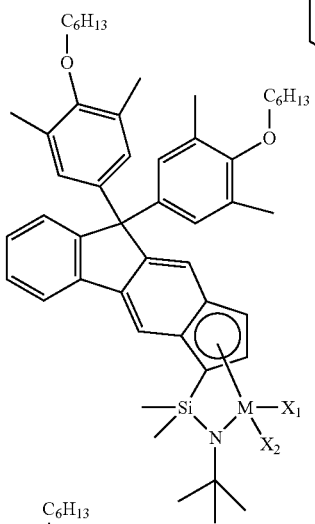
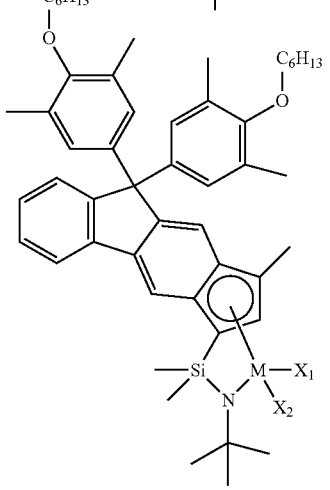

-continued
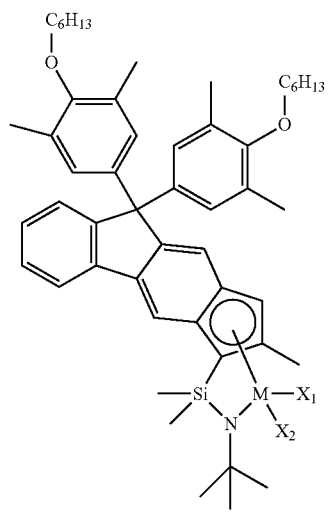
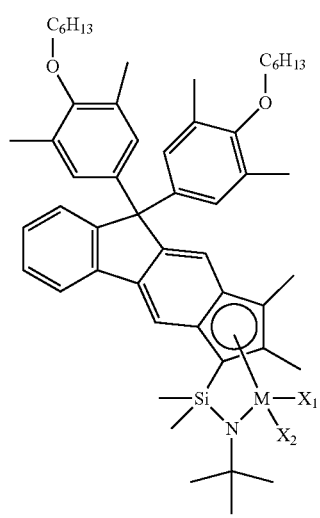
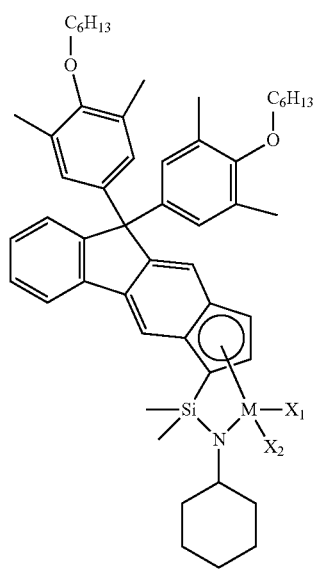
-continued
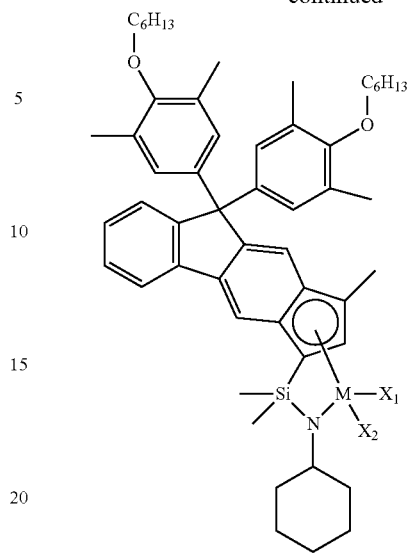
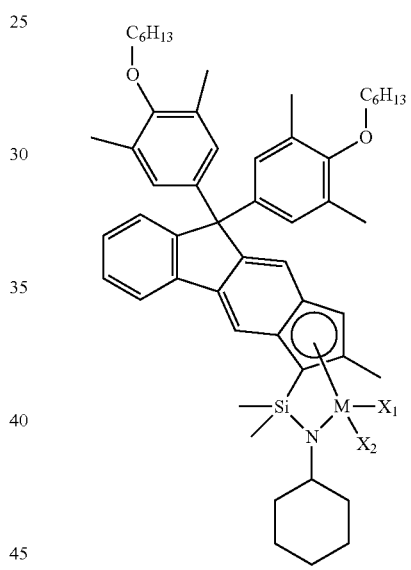
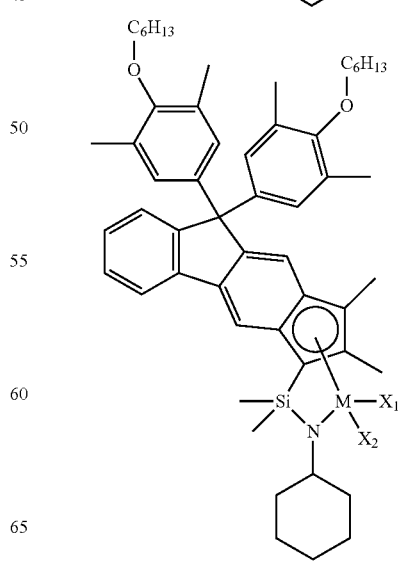

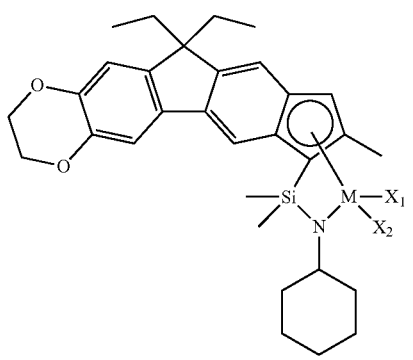
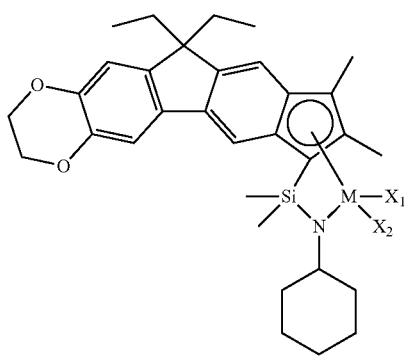
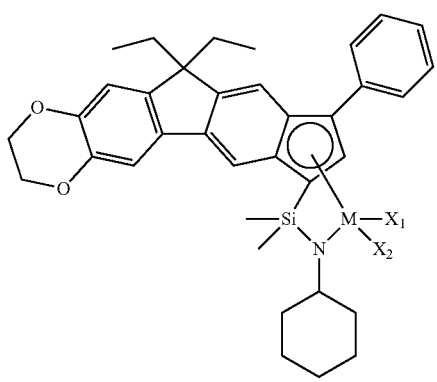
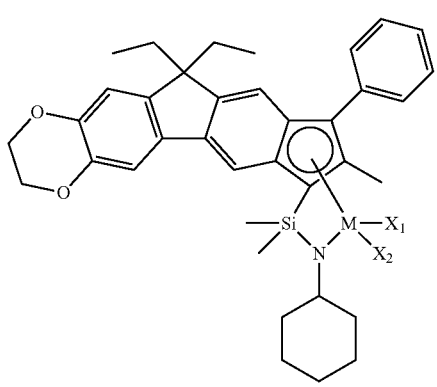
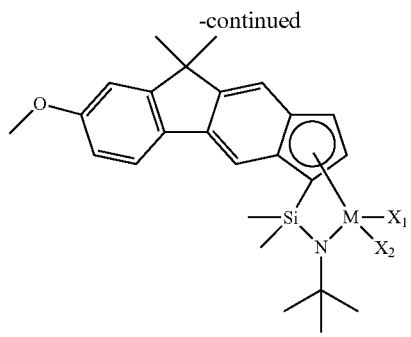
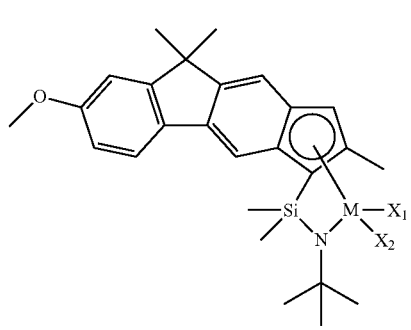
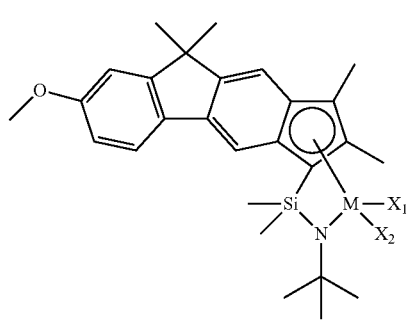
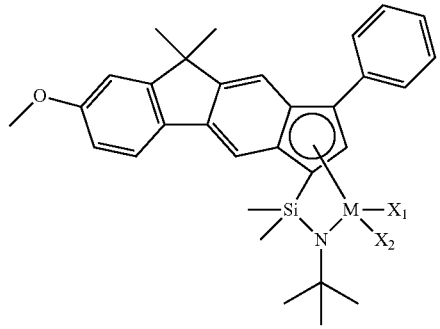
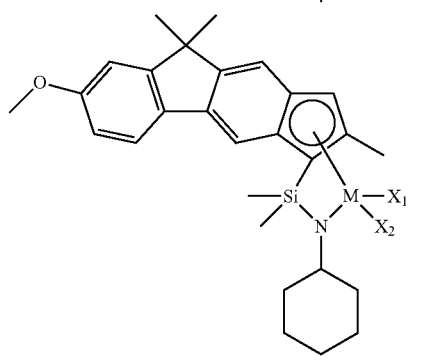

-continued
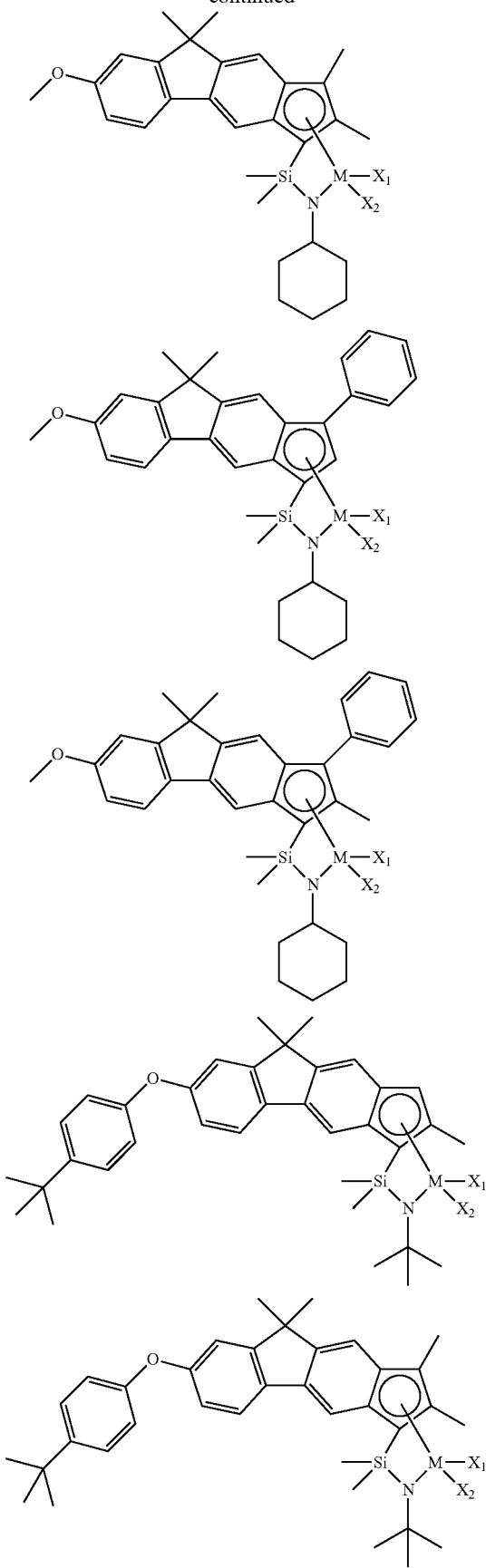
-continued
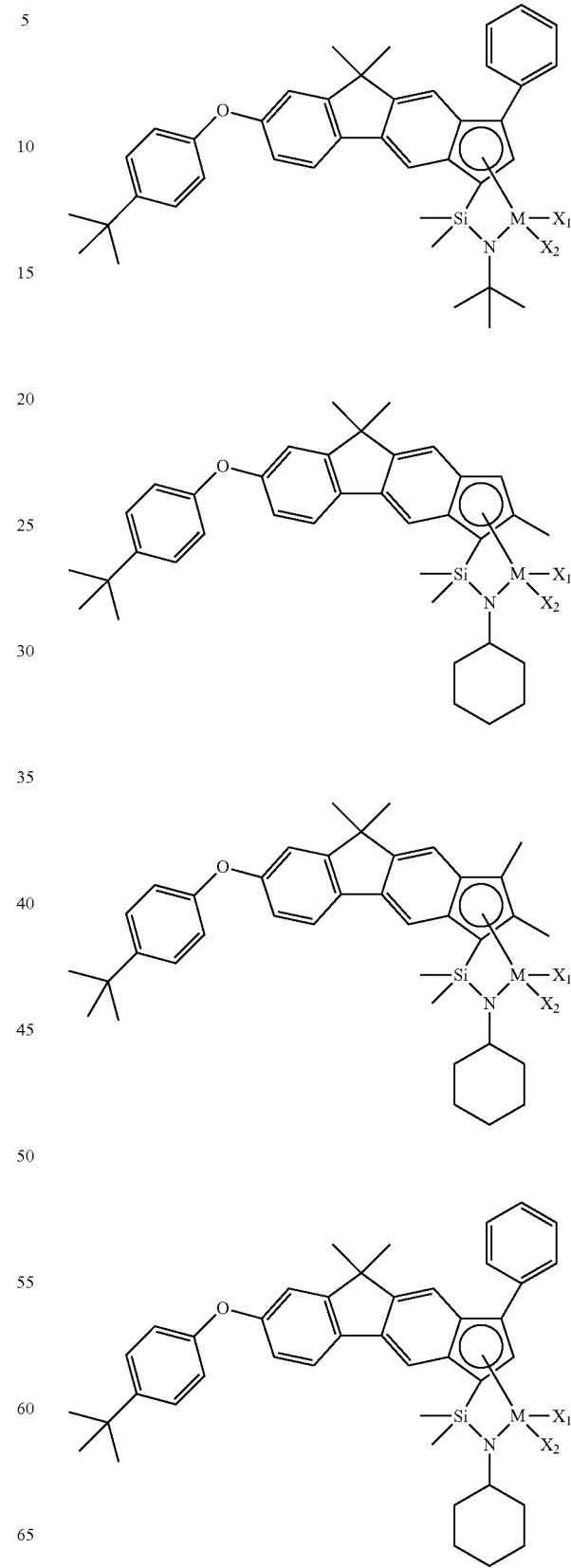

-continued
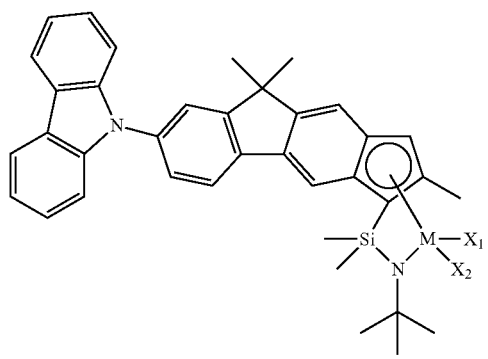
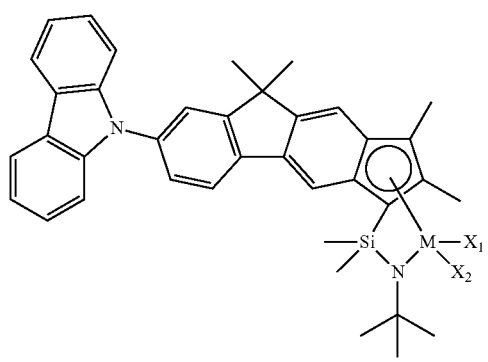
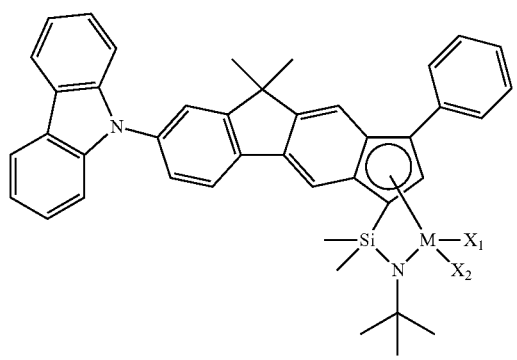
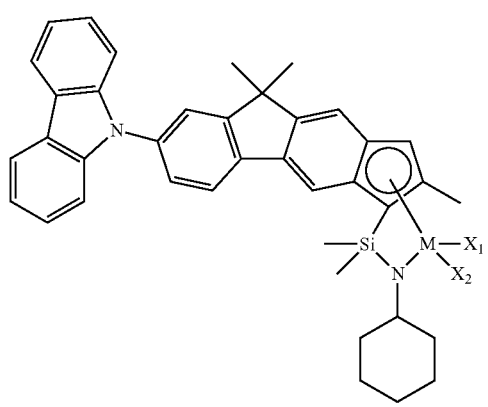
-continued
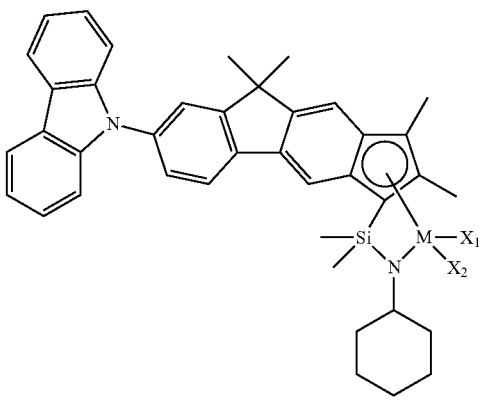
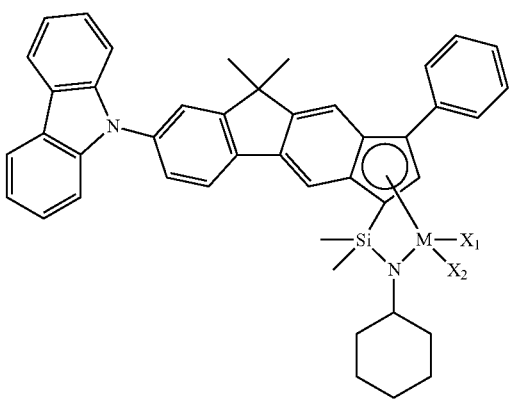
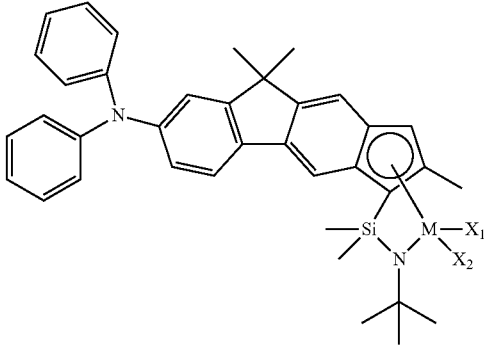
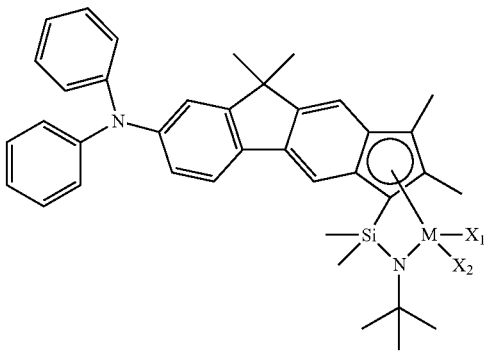

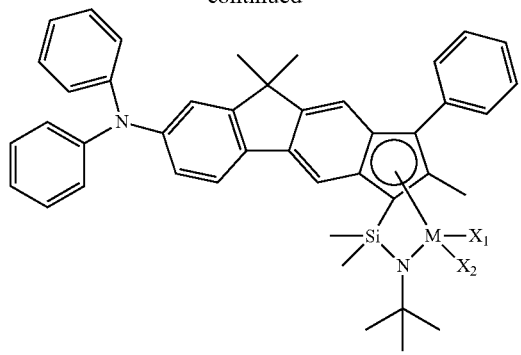
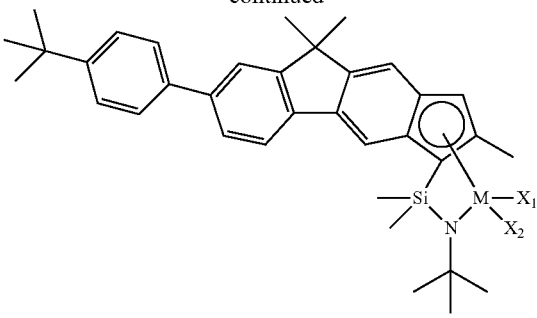
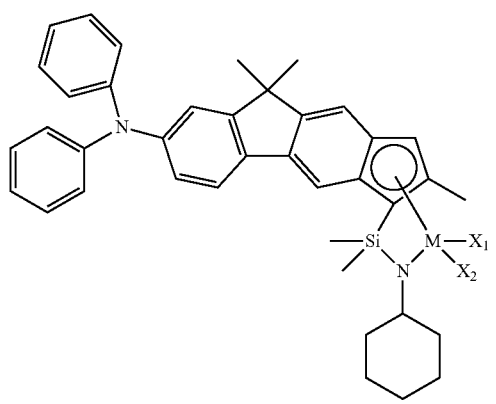
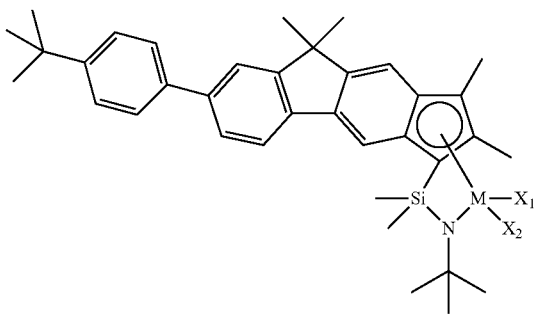
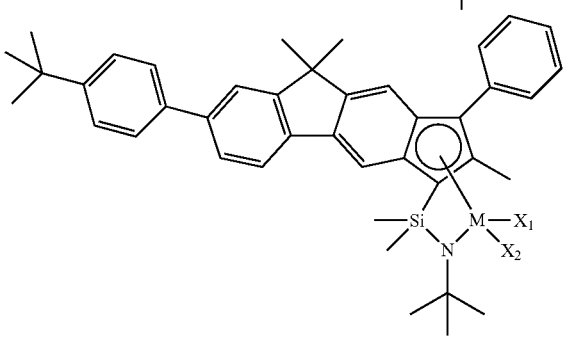
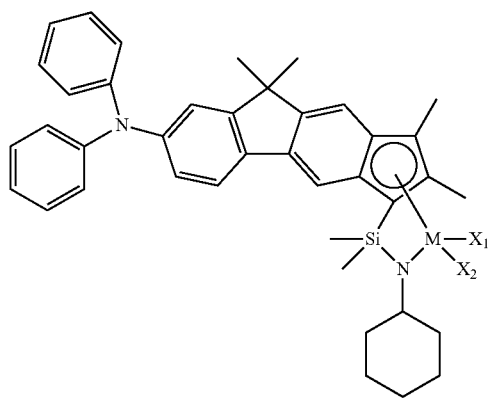
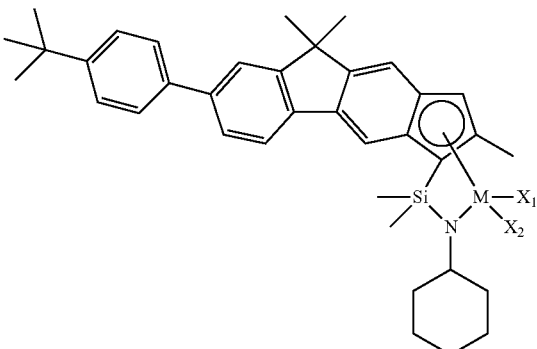
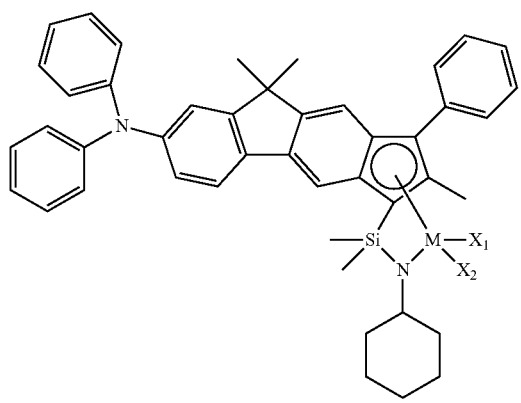
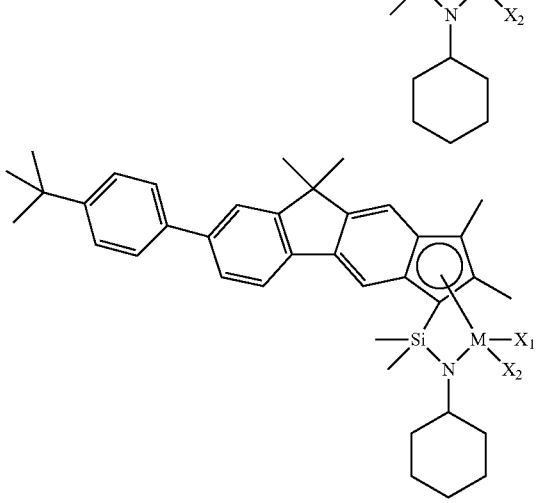

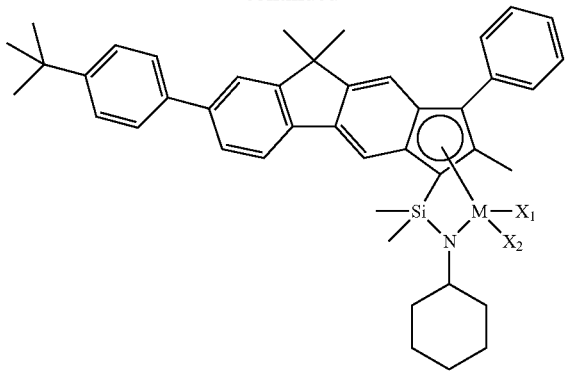
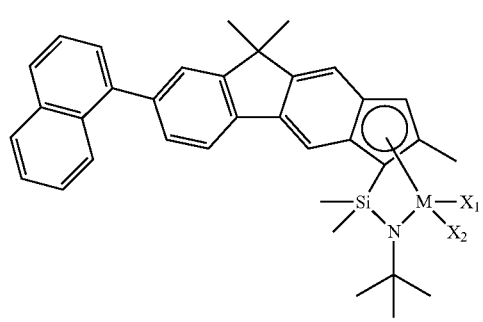
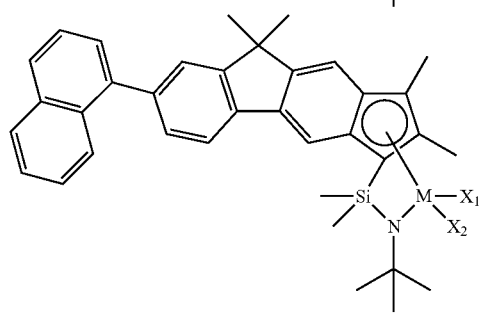
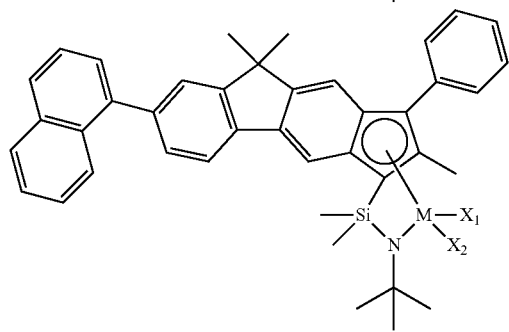
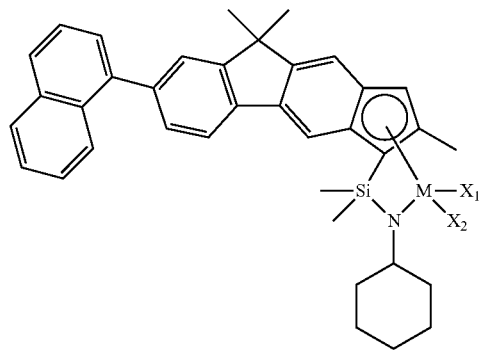

-continued
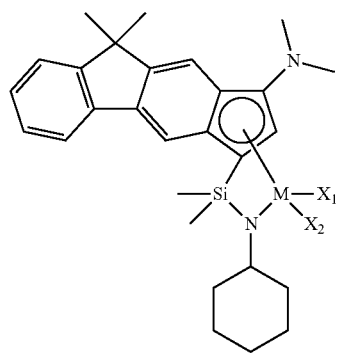
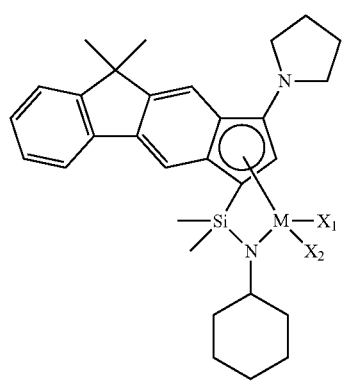
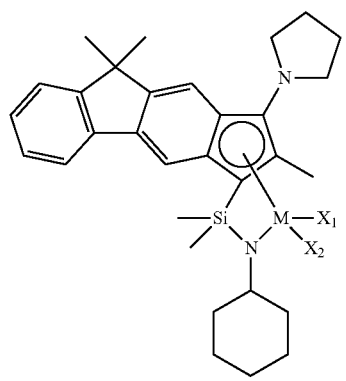
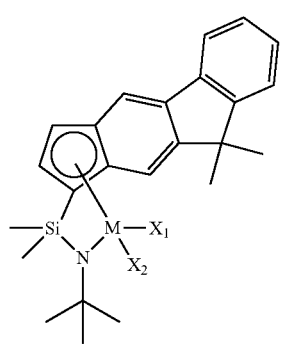
-continued
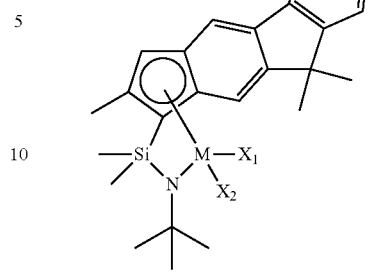
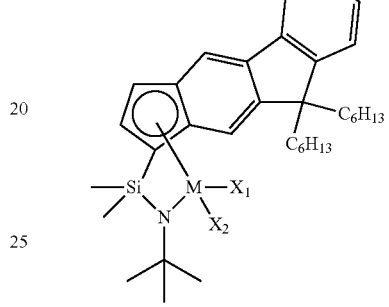
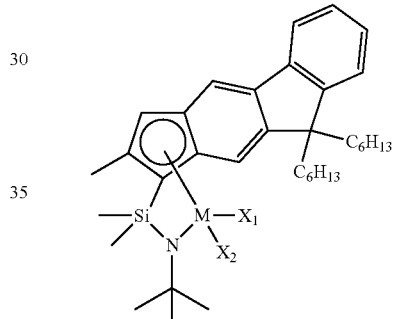
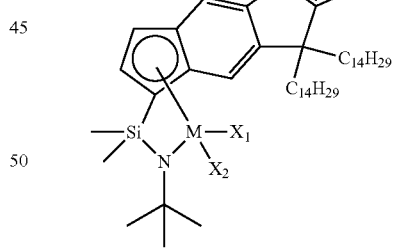
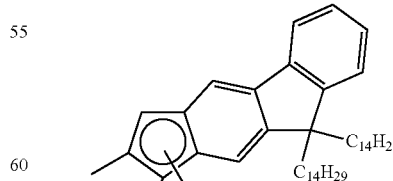

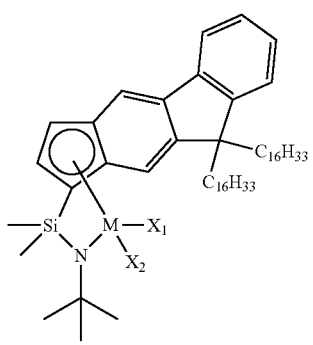
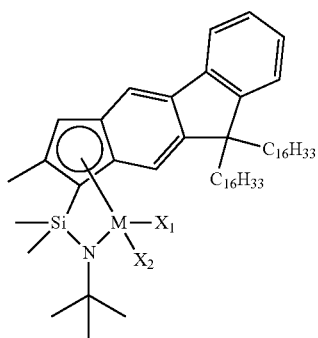
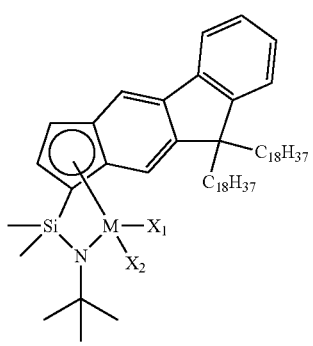
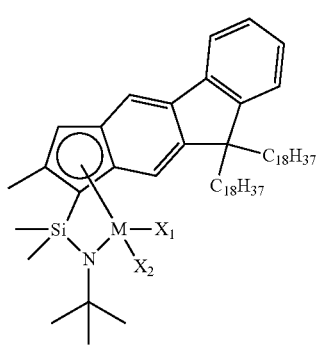
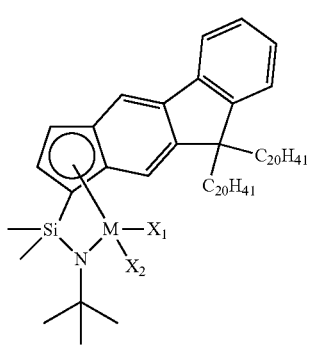
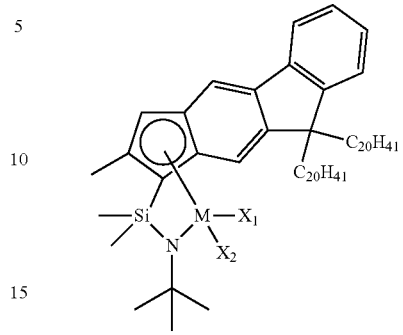
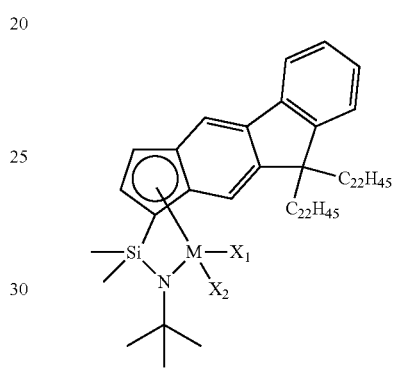
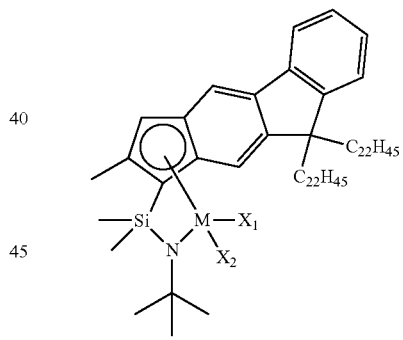
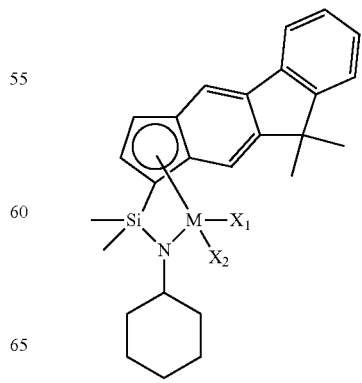

55
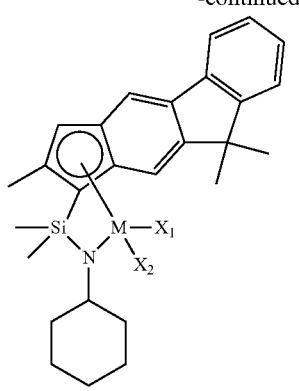
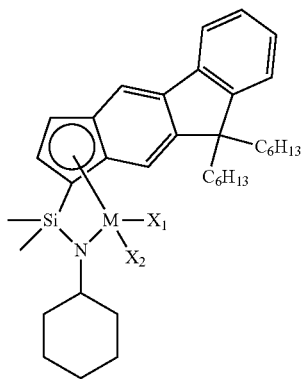
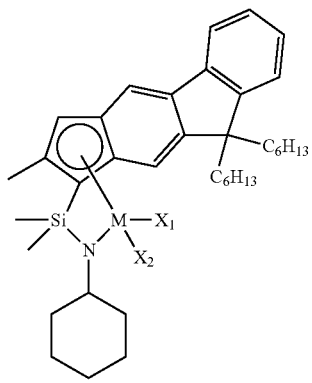
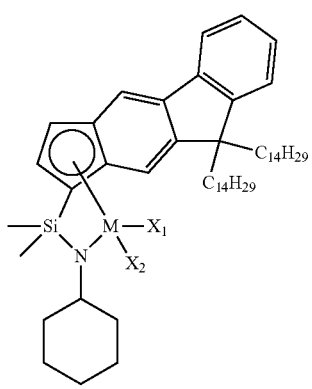
56
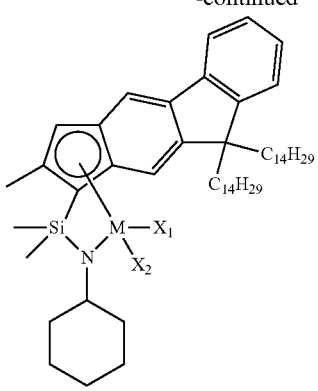
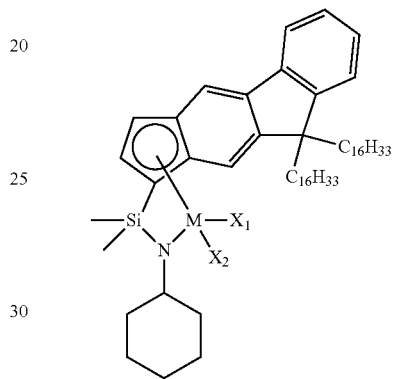
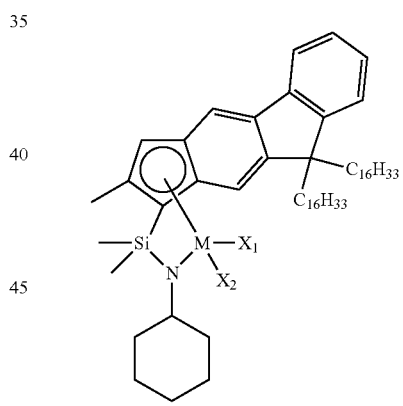
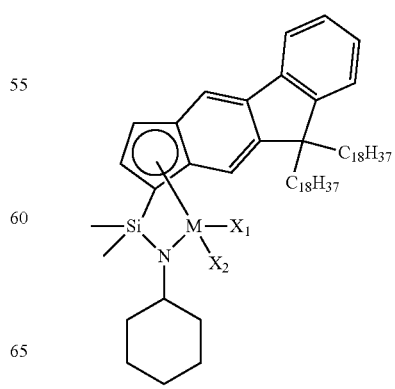

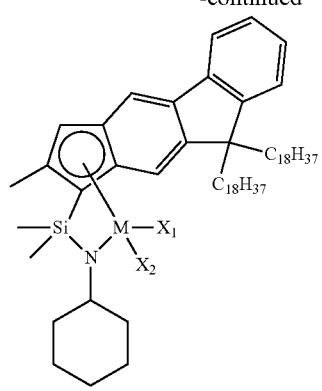
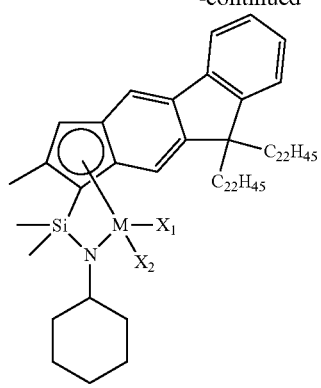
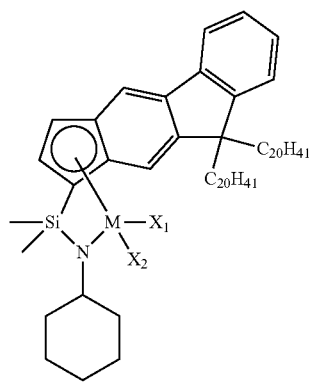
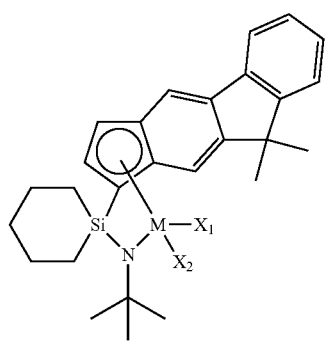
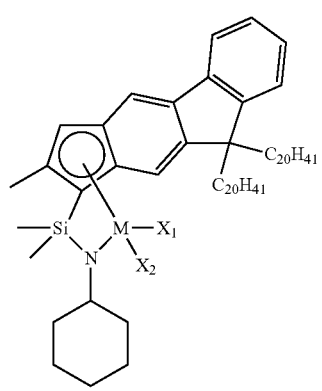
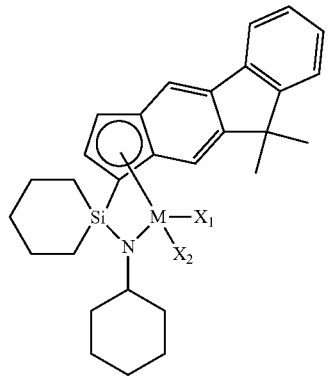

-continued
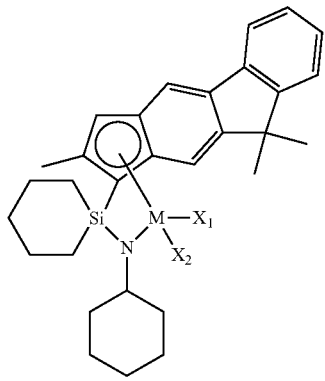
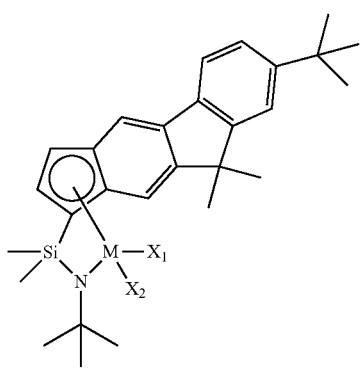
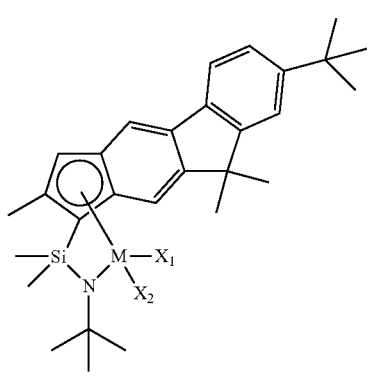
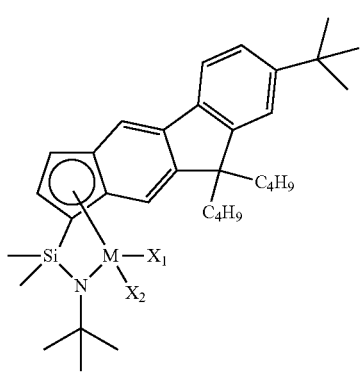
-continued
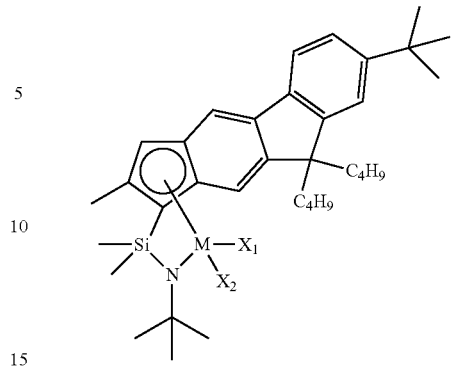
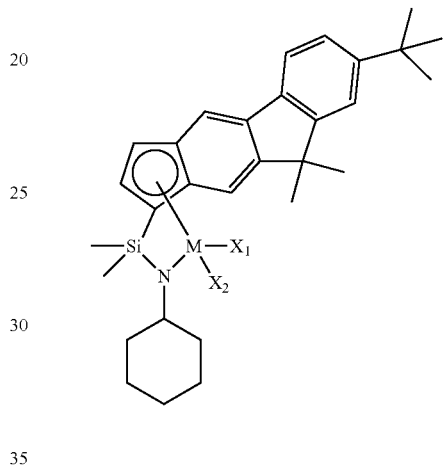
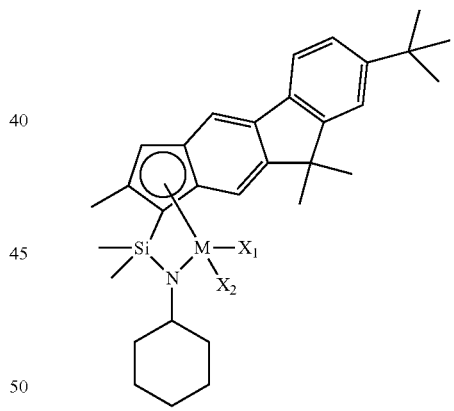
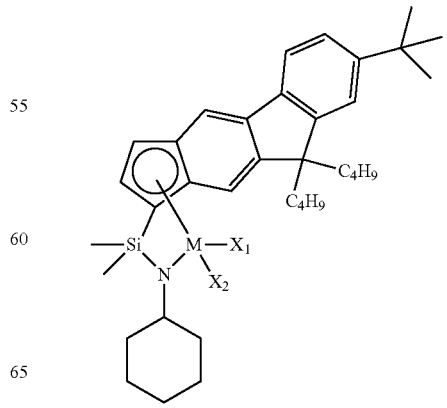

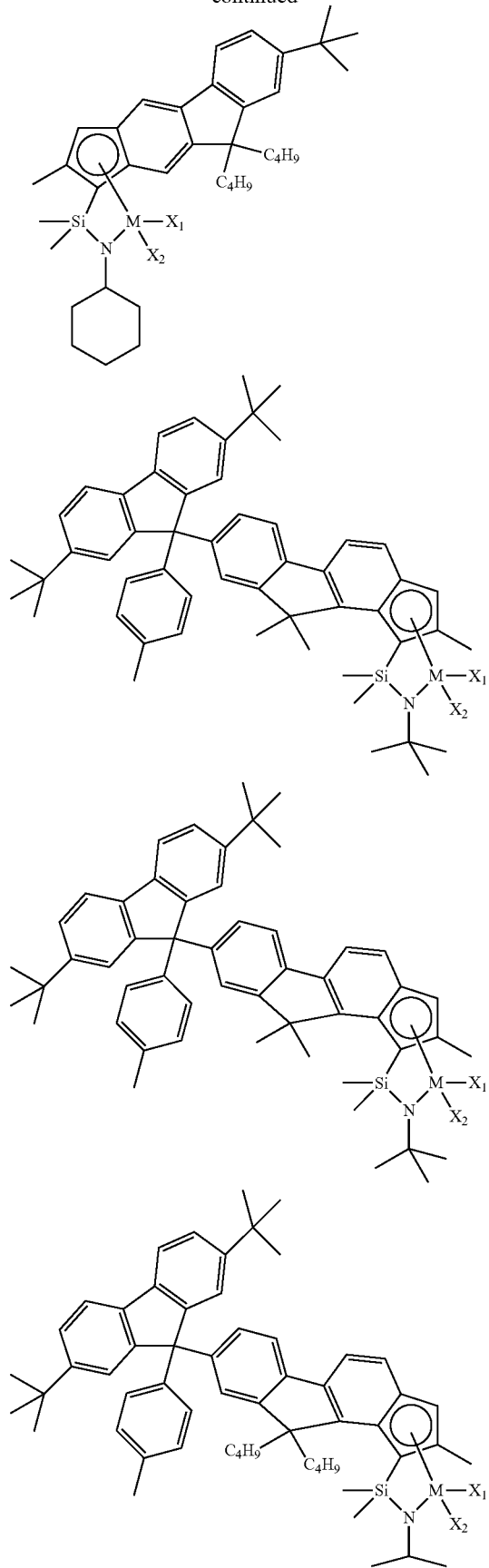
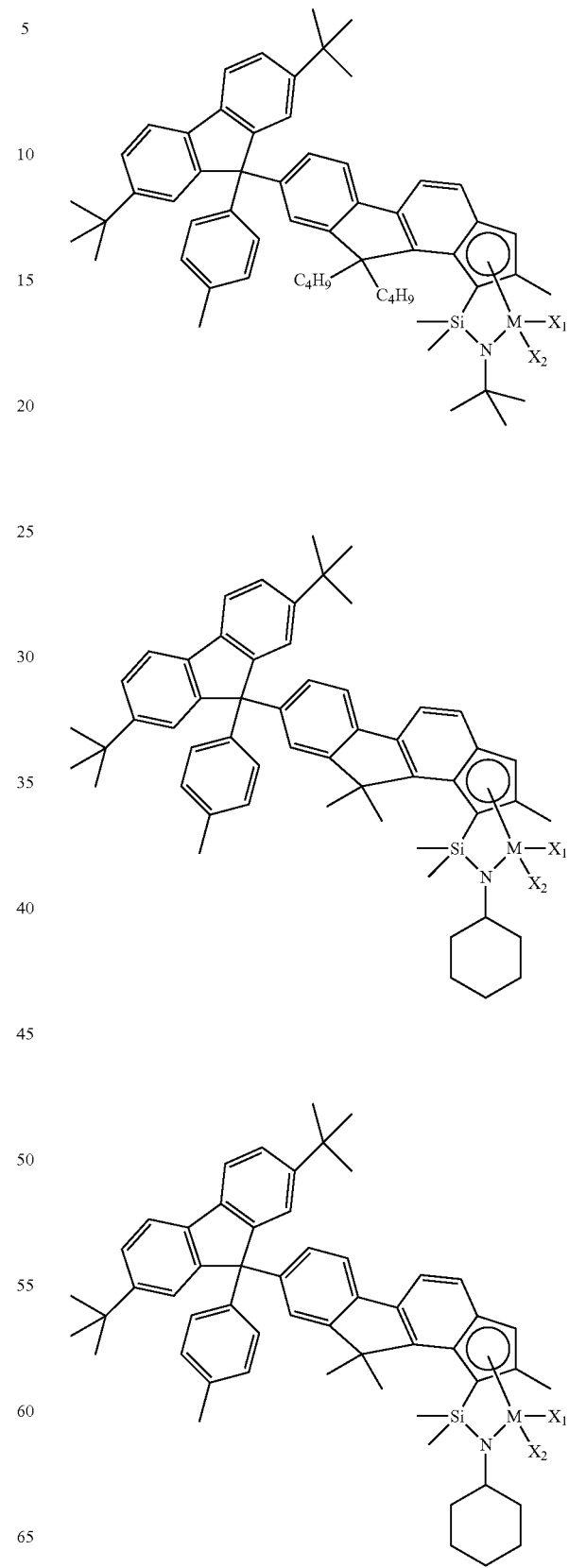

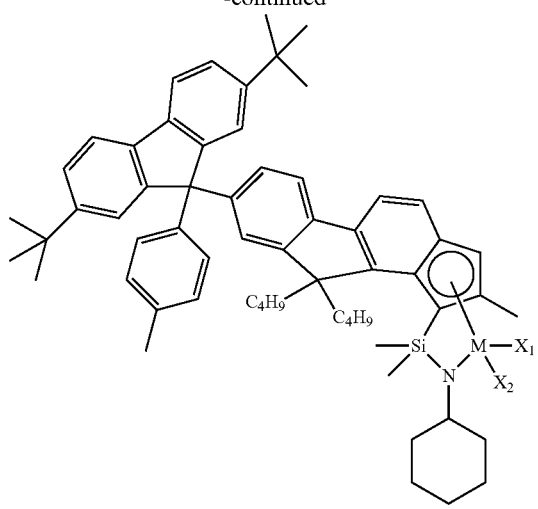
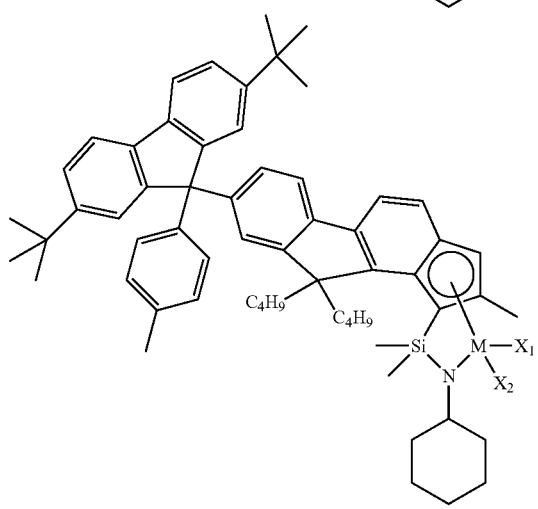
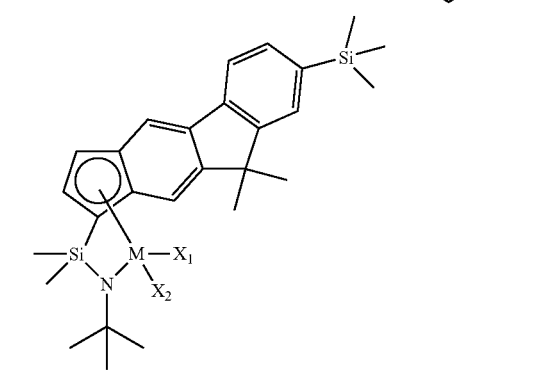
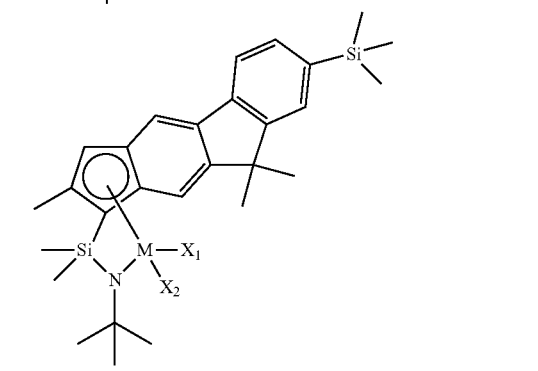
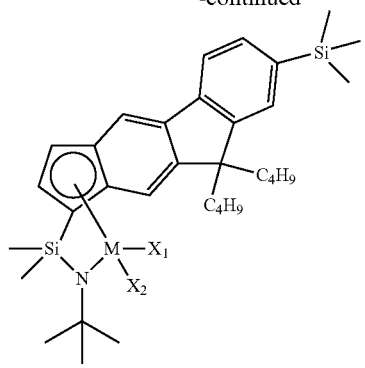
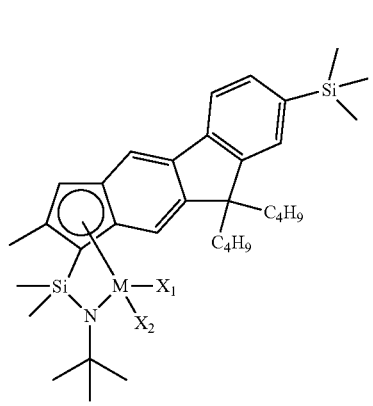
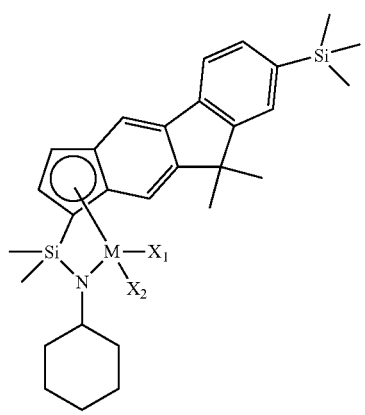
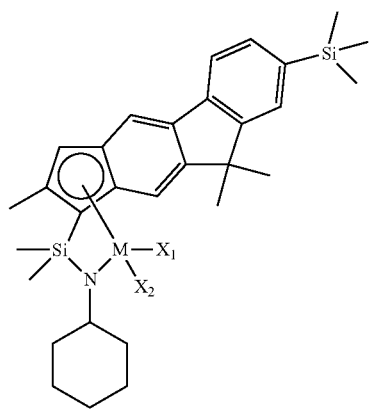

-continued
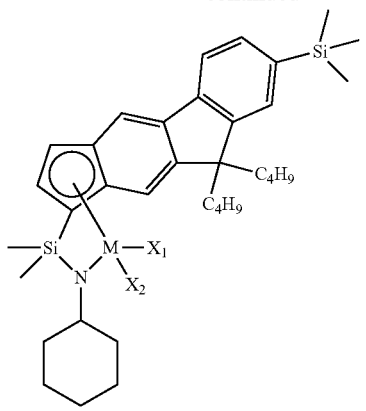
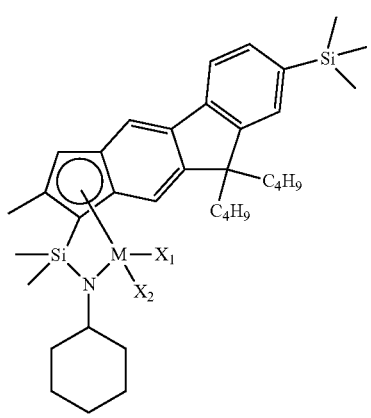
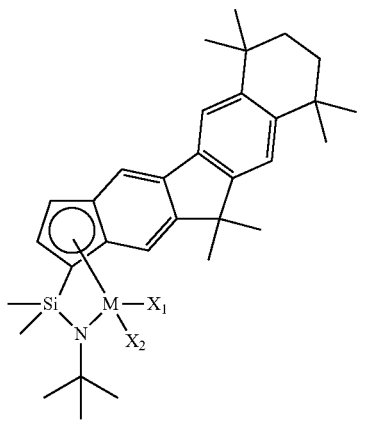
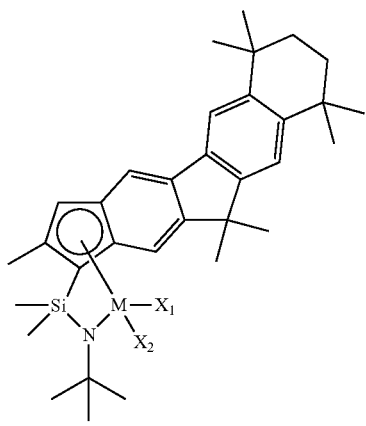
-continued
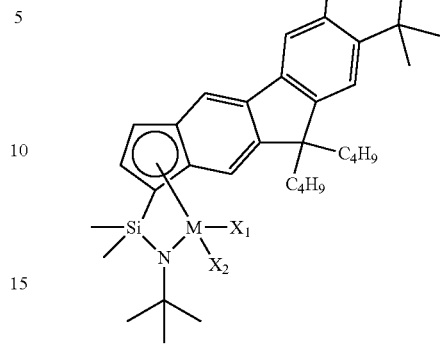
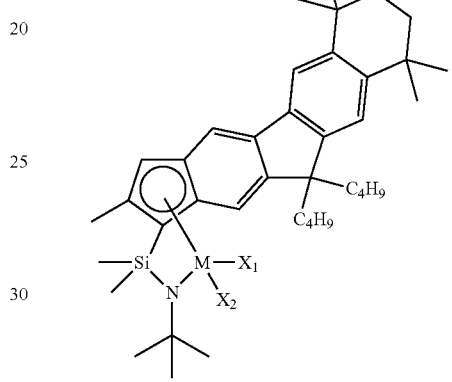
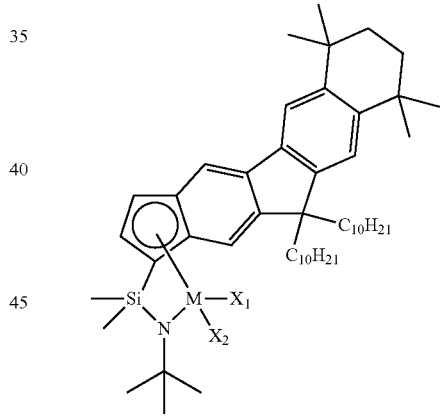
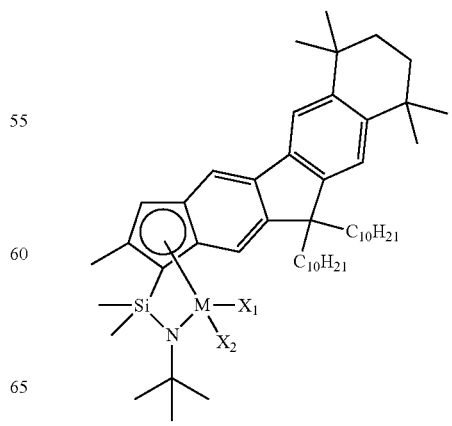

67
-continued
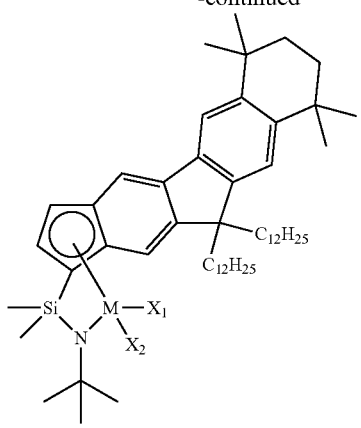
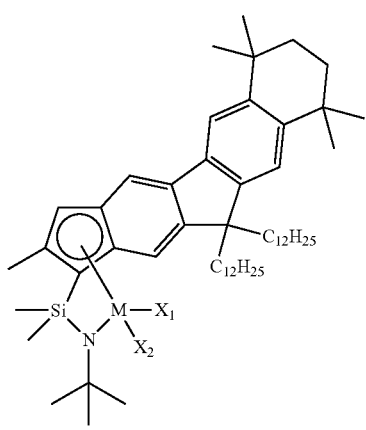
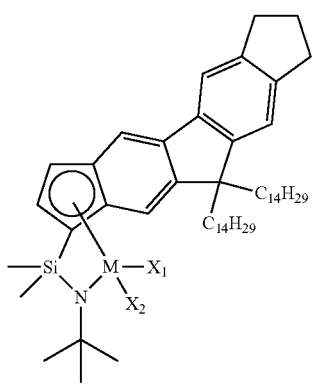
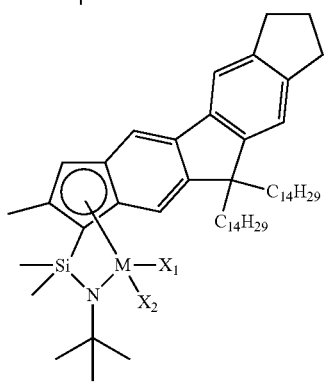
68
-continued
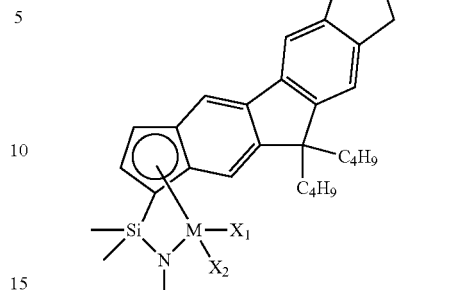
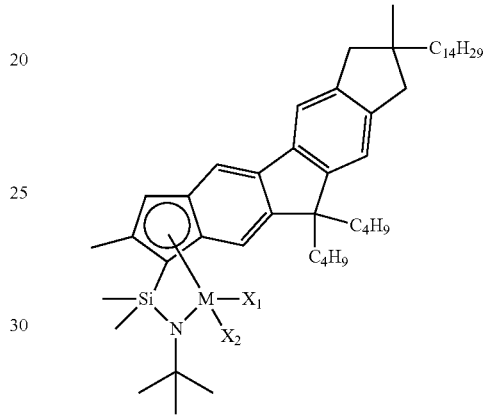
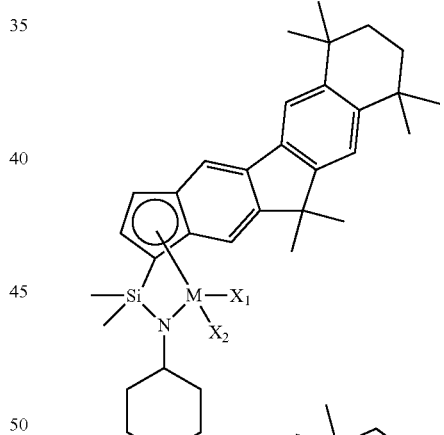
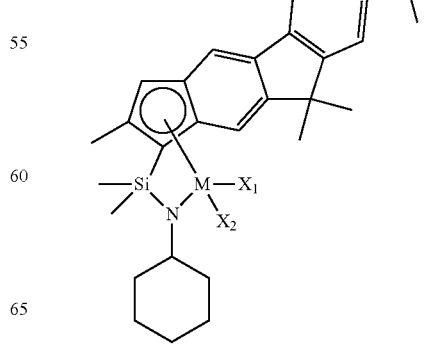

69
-continued
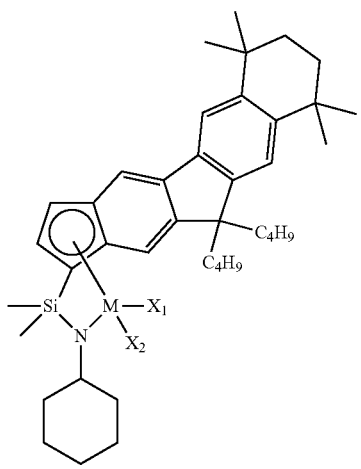
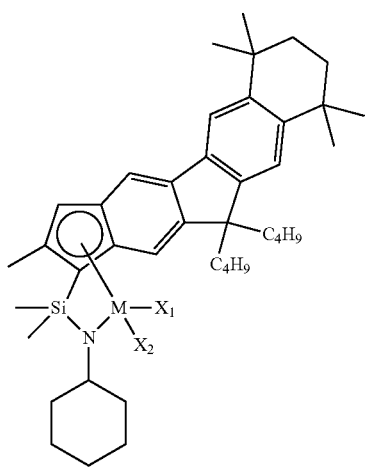
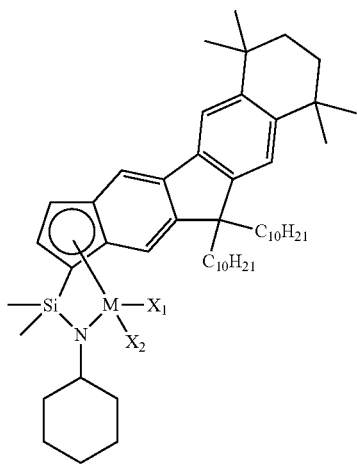
70
-continued
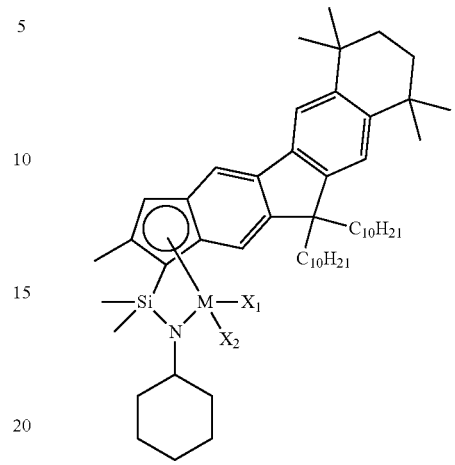
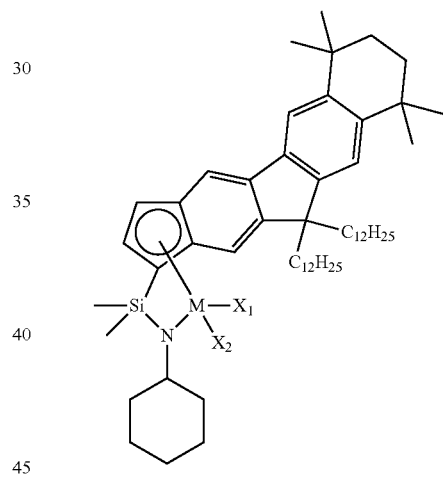
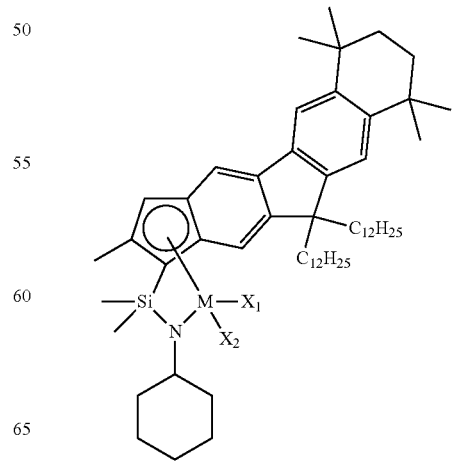

-continued
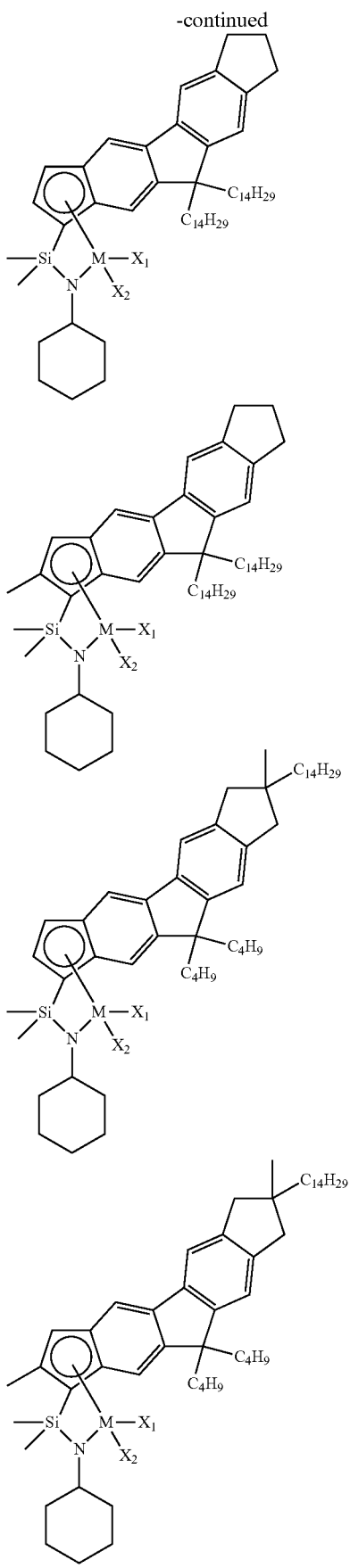
-continued
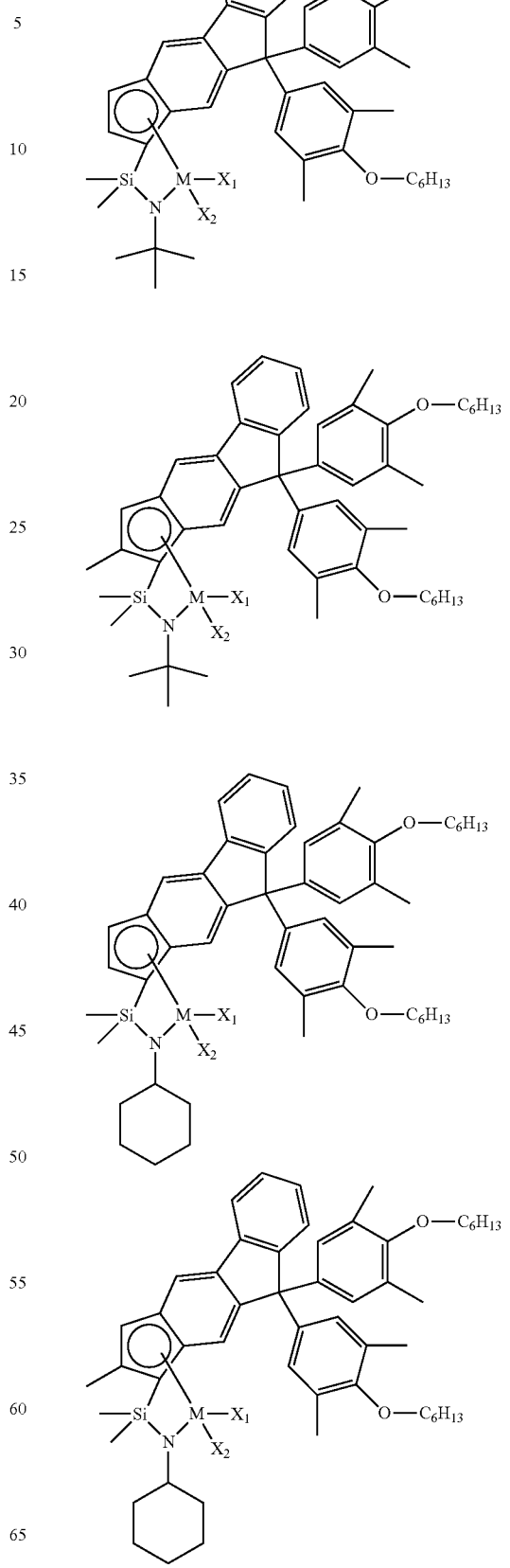

-continued
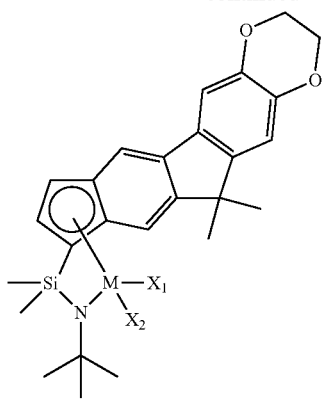
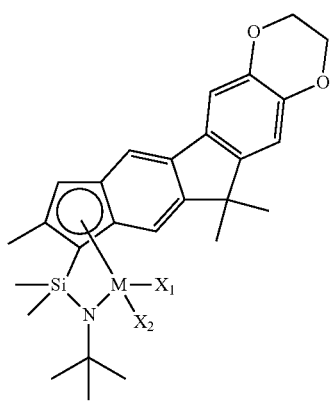
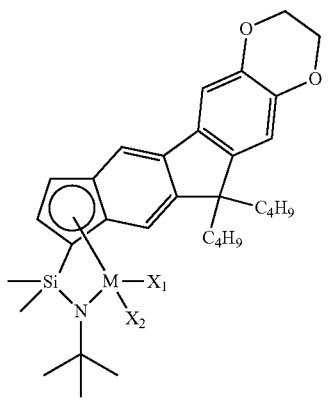
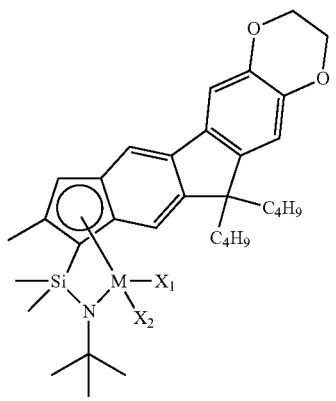
-continued
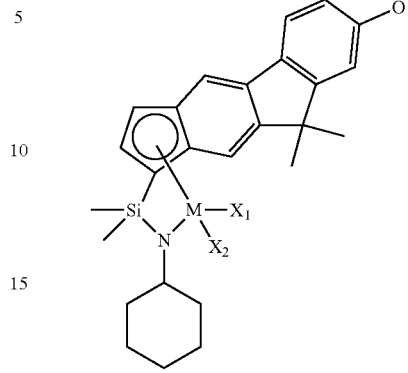
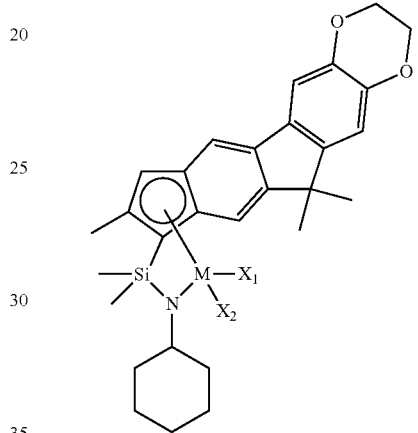
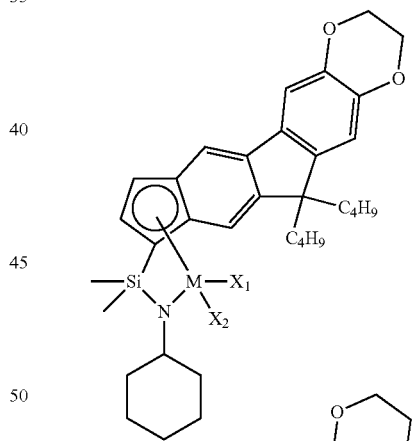
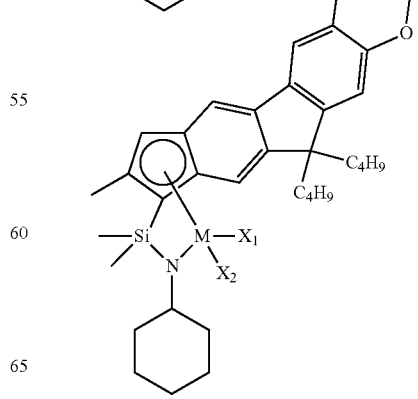

75
-continued
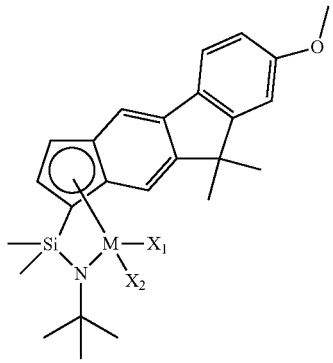
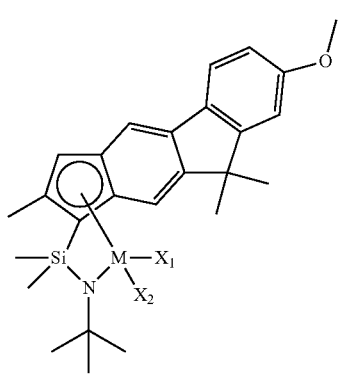
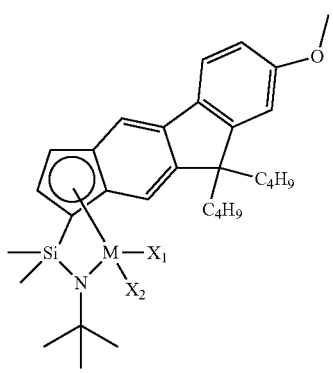
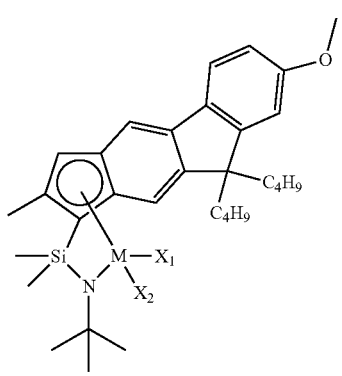
76
-continued
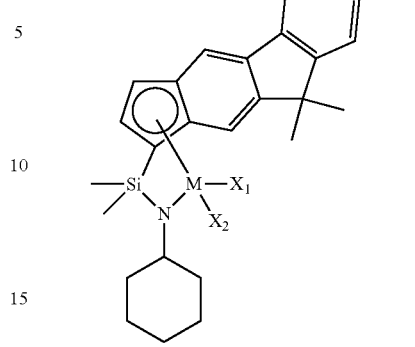
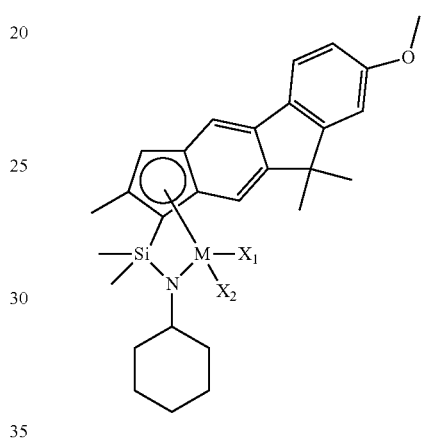
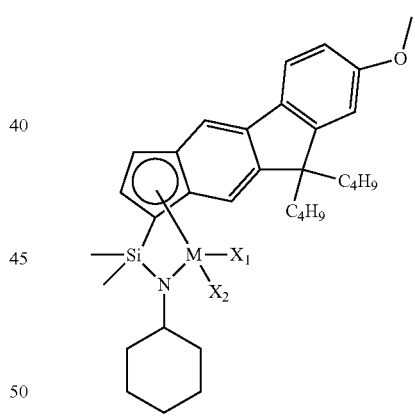
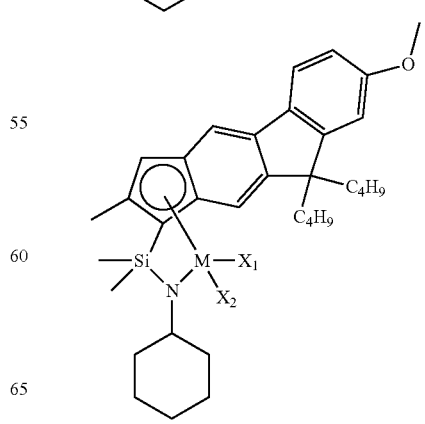

77
-continued
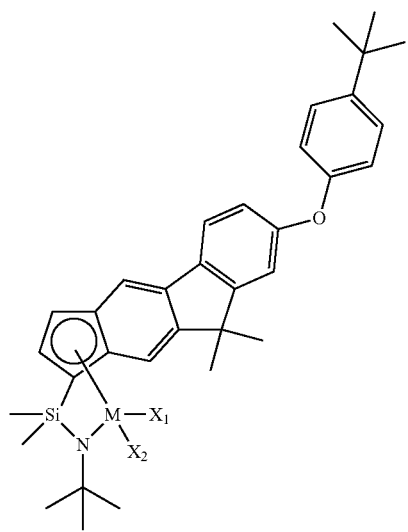
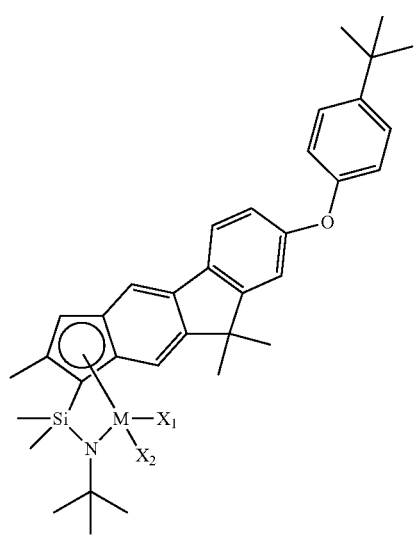
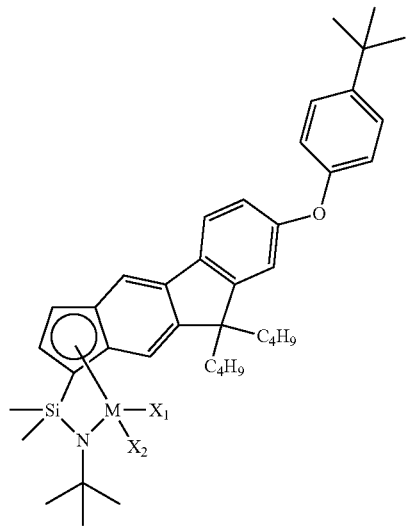
78
-continued
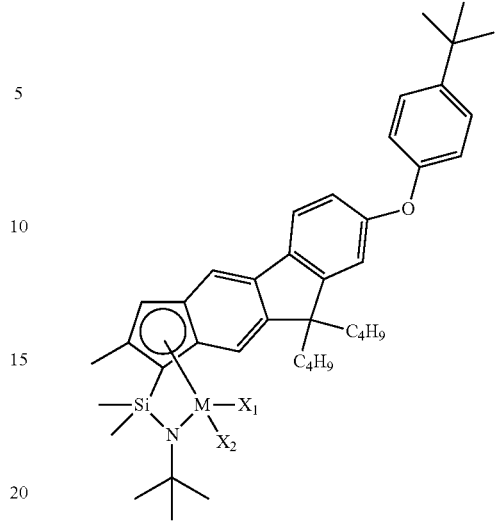
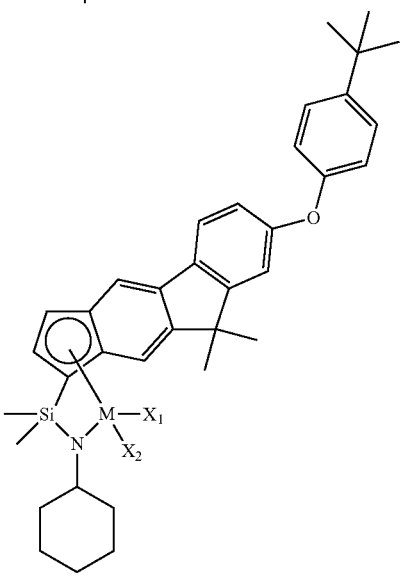
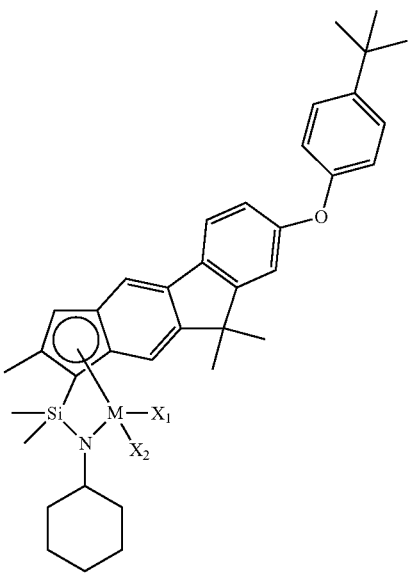

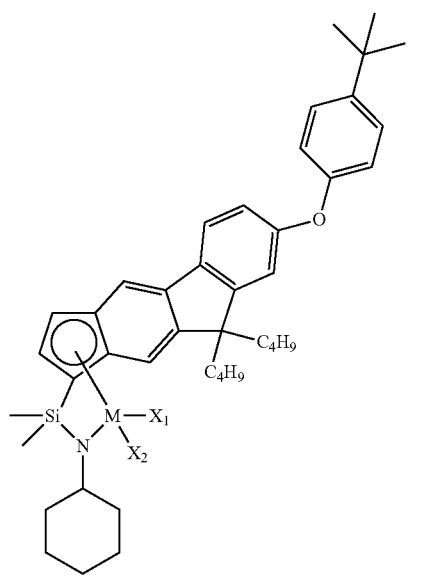
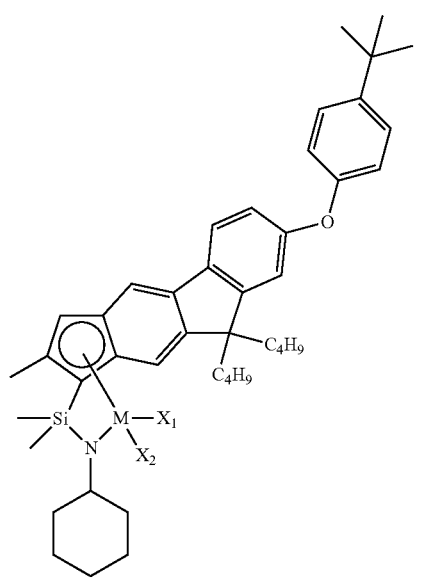
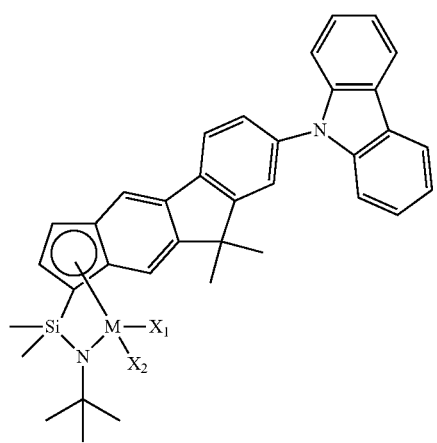
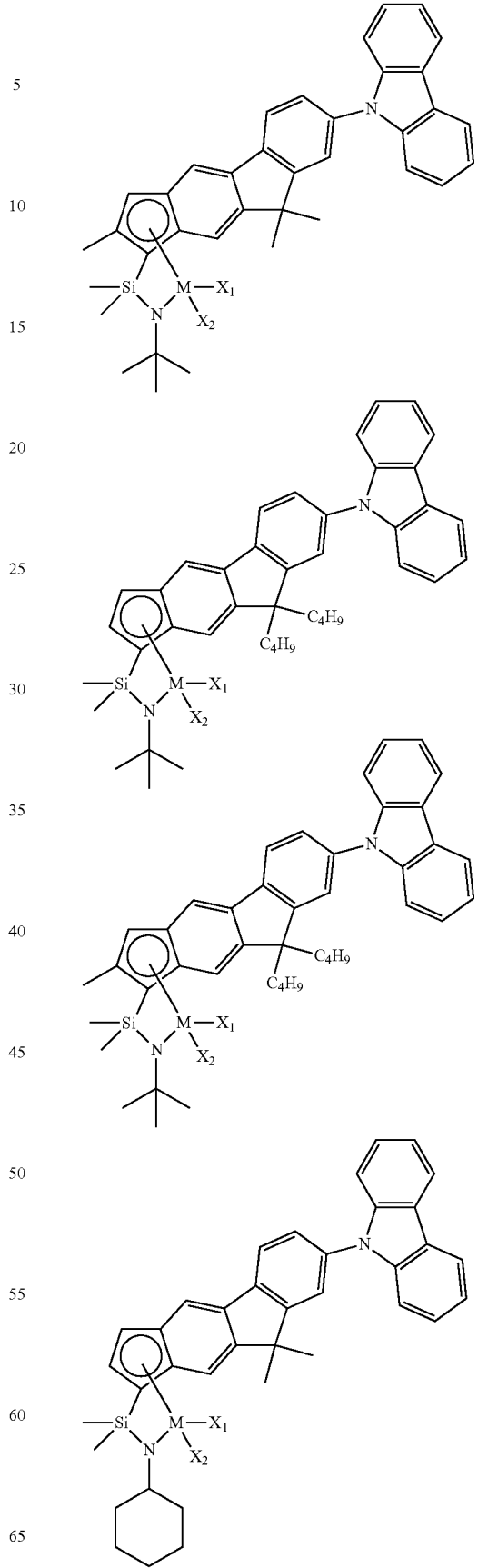

81
-continued
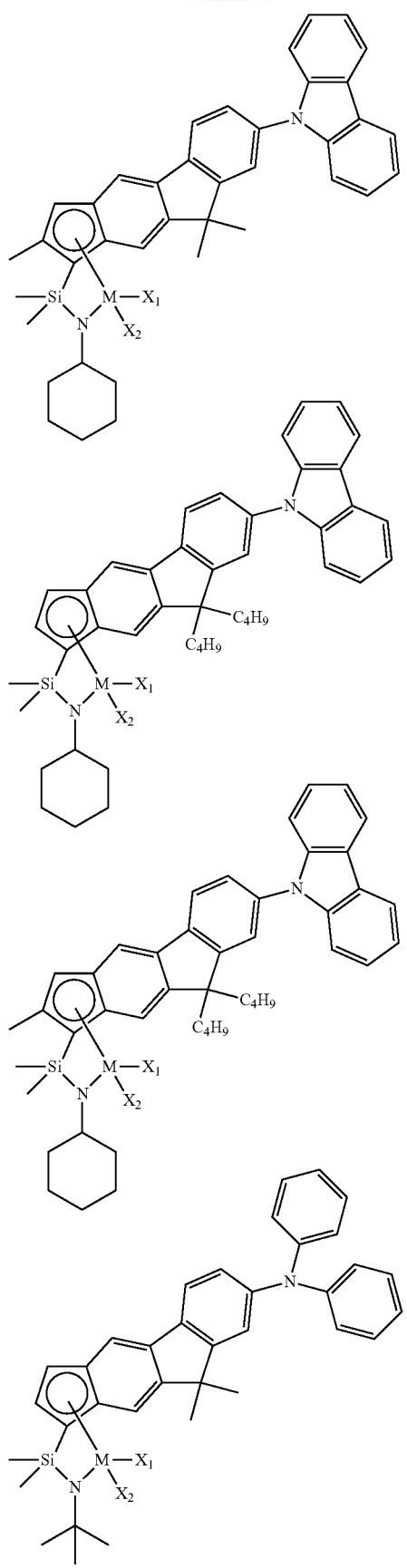
82
-continued
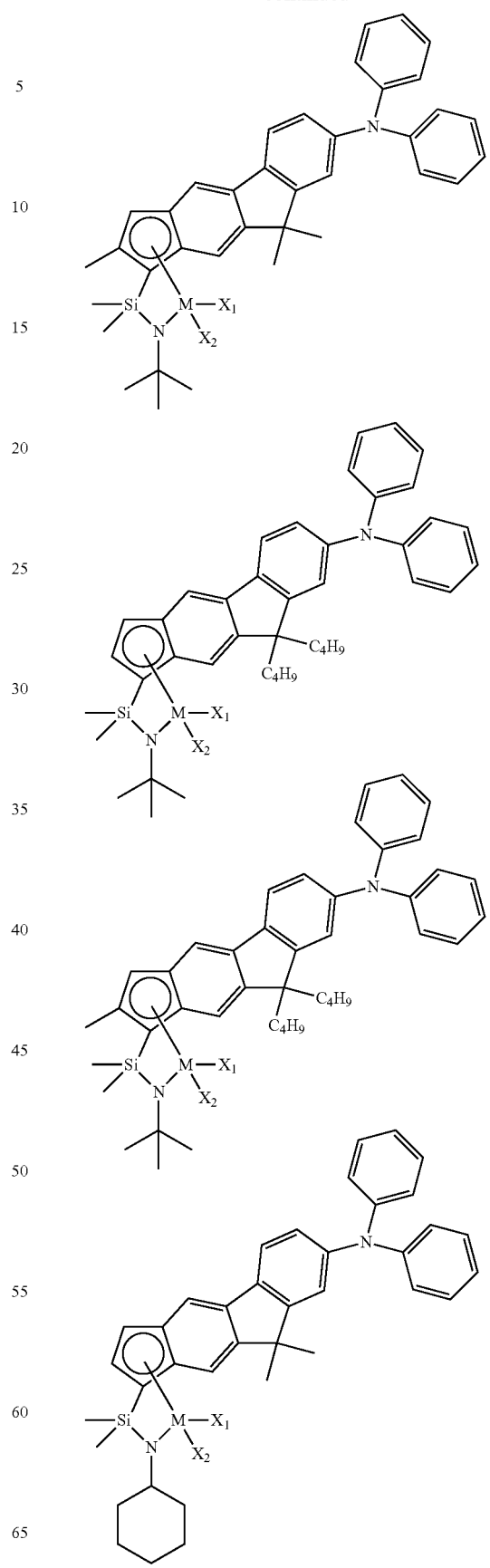

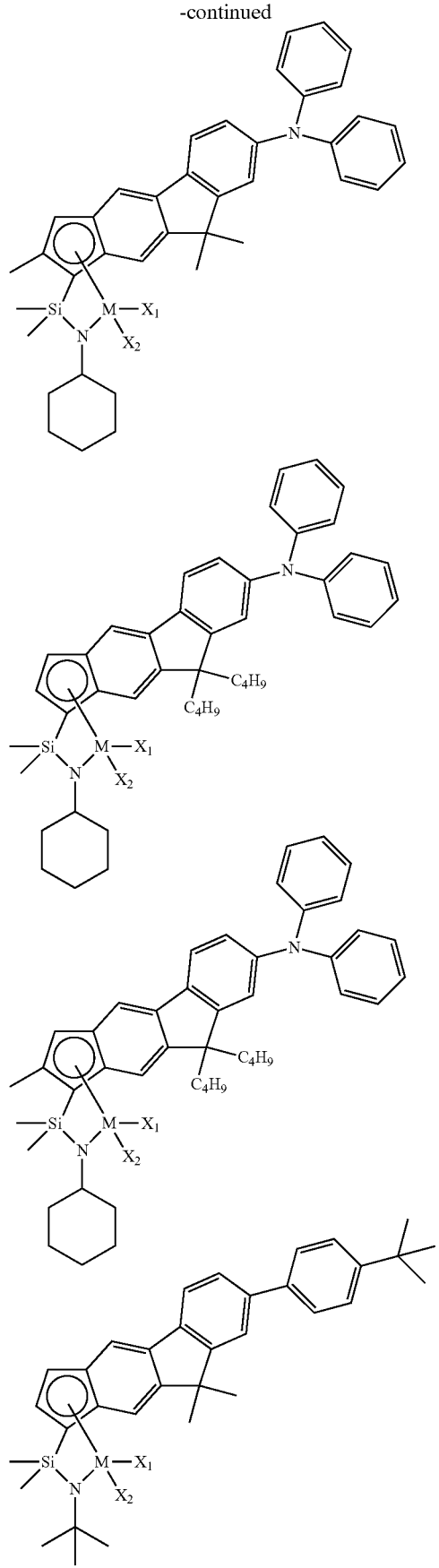
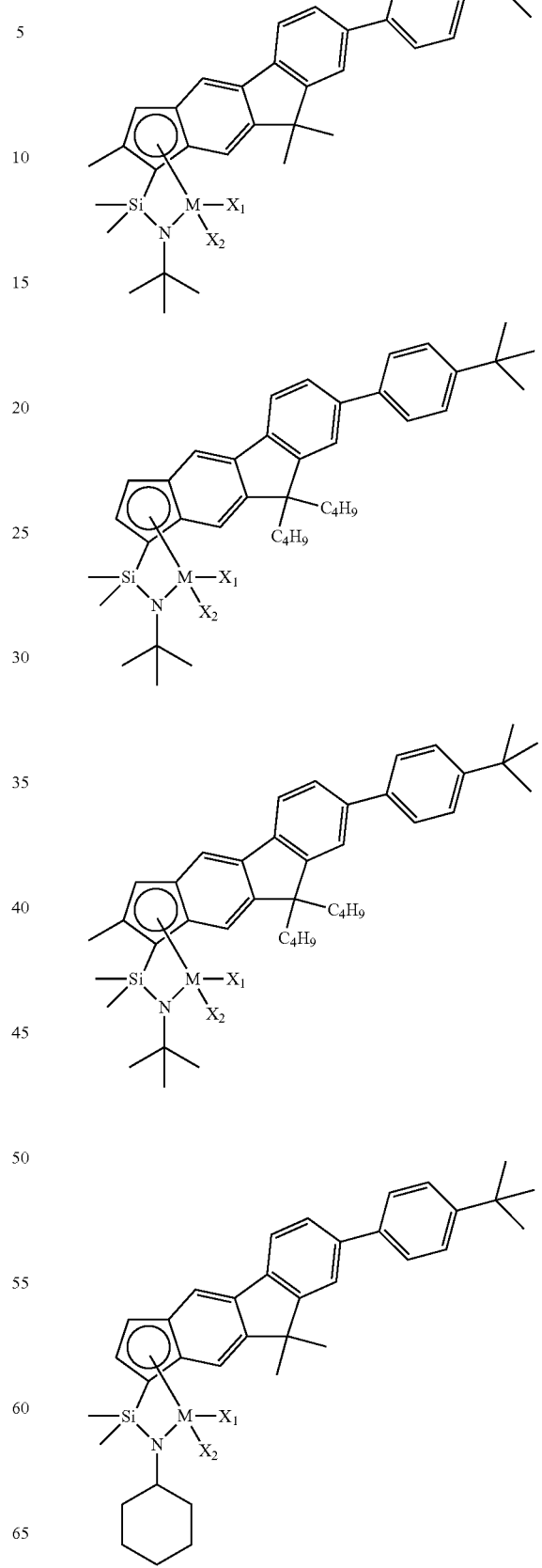

85
-continued
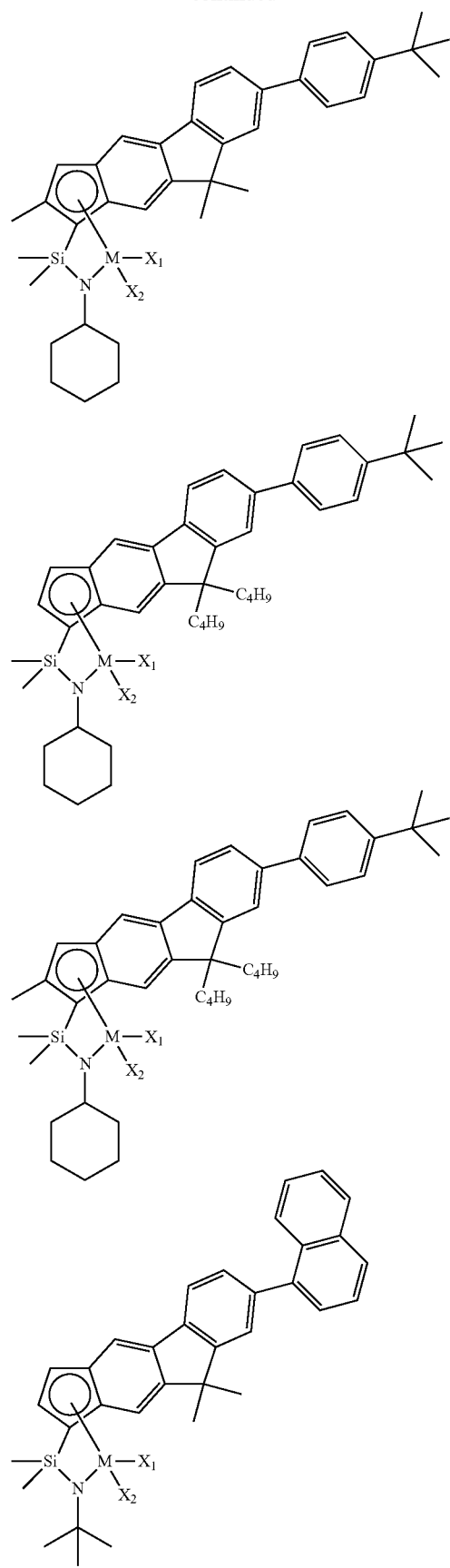
86
-continued
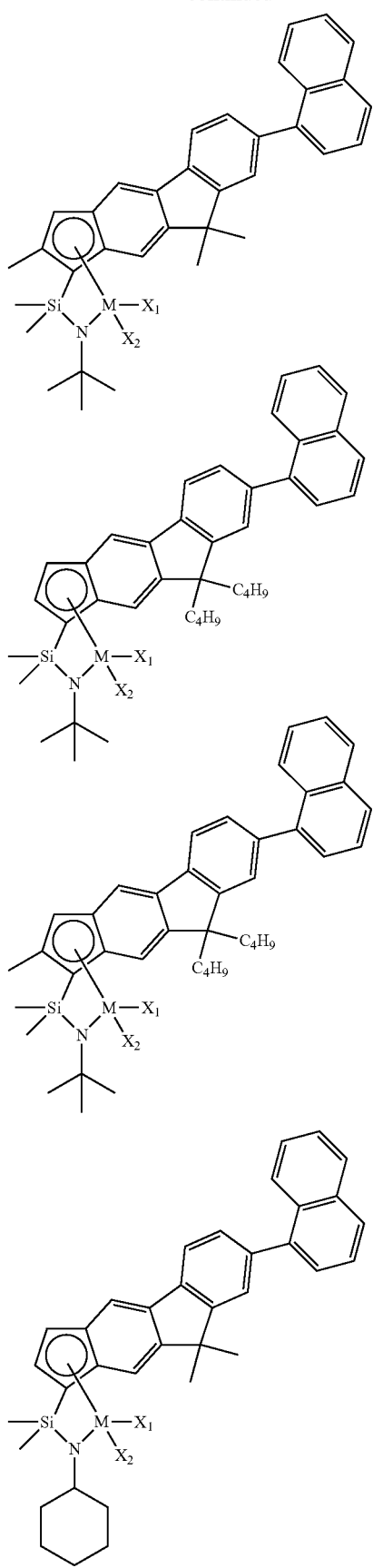

-continued

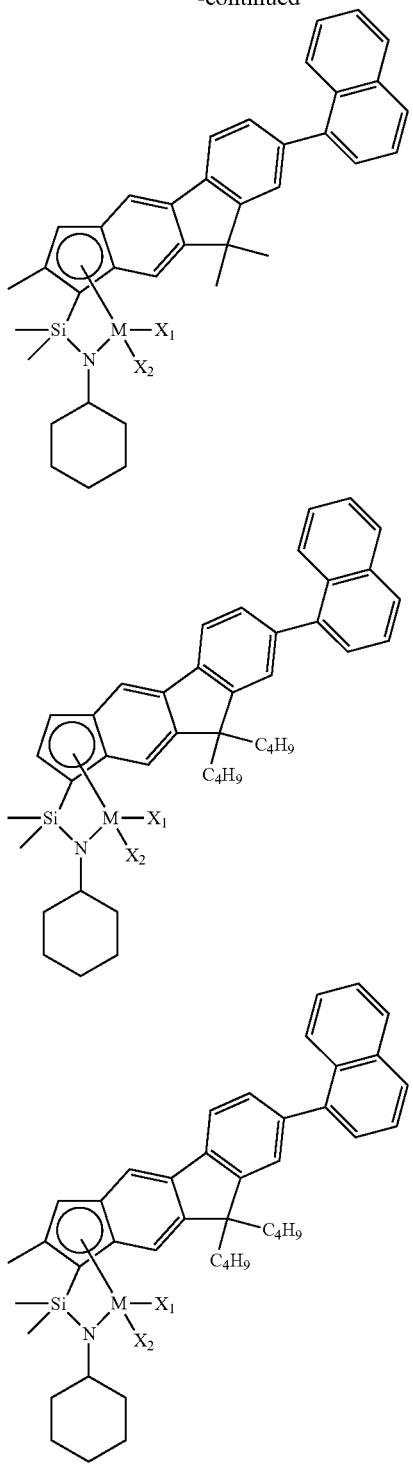

M is Ti, Zr, or Hf; and $X_1$ and $X_2$ each have the same definition as defined in Chemical Formula 1 above.

Meanwhile, in order to be an active catalyst component to be used for preparing ethylene based polymers selected from ethylene homopolymers and copolymers of ethylene and α-olefin, the transition metal compound according to the present invention may be preferably employed together with, as cocatalyst, an aluminoxane compound, a boron compound, or a mixture thereof, which can extract an $X_1$ or $X_2$ ligand from the transition metal complex to cationize the core metal and act as a counterion having weak bond strength, that is, an anion, and the catalyst composition containing the transition metal compound and the cocatalyst is also within the scope of the present invention.

The boron compound usable as the cocatalyst in the present invention has been known in U.S. Pat. No. 5,198, 401, and may be selected from boron compounds represented by Chemical Formulas 4 to 6 below.

$B(R^{41})_3$ [Chemical Formula 4]

$[R^{42}]^+[B(R^{41})_4]^-$ [Chemical Formula 5]

$[(R^{43})_p ZH]^+[B(R^{41})_4]^-$ [Chemical Formula 6]

[In Chemical Formulas 4 to 6, B is a boron atom;

$R^{41}$ is phenyl, and the phenyl may be further substituted with 3 to 5 substituents selected from a fluorine atom, (C1-C50)alkyl substituted or unsubstituted with a fluorine atom, or (C1-C50)alkoxy substituted or unsubstituted with a fluorine atom;

$R^{42}$ is (C5-C7)aromatic radical or (C1-C50)alkyl(C6-C20)aryl radical, (C6-C30)aryl(C1-C50)alkyl radical, for example, triphenylmethyl radical;

Z is a nitrogen or phosphorus atom;

$R^{43}$ is (C1-C50)alkyl radical, or anilinium radical substituted with a nitrogen atom and two (C1-C10)alkyl groups; and p is an integer of 2 or 3.]

Preferable examples of the boron based cocatalyst may include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate, and tetrakis(3,5-bistrifluoromethylphenyl)borate. In addition, certain compounded examples thereof may include ferrocenium tetrakis(pentafluorophenyl)borate, 1,1'-dimethylferrocenium tetrakis(pentafluorophenyl)borate, tetrakis(pentafluorophenyl)borate, triphenylmethyl tetrakis(pentafluorophenyl)borate, triphenylmethyl tetrakis(3,5-bistrifluoromethylphenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, and tri(dimethylphenyl)phosphonium tetrakis(pentafluorophenyl)borate. Among them, preferable are N,N-dimethylanilinium tetrakis(pentafluorophenyl)borate, triphenylmethyl tetrakis(pentafluorophenyl)borate, and tris(pentafluorophenyl)borane.

In the present invention, the aluminum compounds usable as the cocatalyst may selected from aluminoxane compounds of Chemical Formula 7 or 8, organic aluminum compounds of Chemical Formula 9, or organic aluminum hydrocarbyloxide compounds of Chemical Formula 10 or 11.

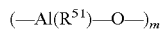  [Chemical Formula 7]

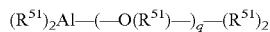  [Chemical Formula 8]

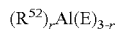  [Chemical Formula 9]

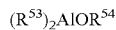  [Chemical Formula 10]

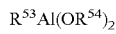  [Chemical Formula 11]

[In Chemical Formulas 7 to 11, $R^{51}$ is (C1-C50)alkyl, preferably methyl or isobutyl; m and q each are independently an integer of 5 to 20; $R^{52}$ and $R^{53}$ each are independently (C1-C50)alkyl; E is a hydrogen or halogen atom; r is an integer of 1 to 3; and $R^{54}$ is (C1-C50)alkyl or (C6-C30) aryl.]

Specific examples of the aluminum compound may include aluminoxane compounds, such as methylaluminoxane, modified methylaluminoxane, tetraisobutylaluminoxane; organic aluminum compounds, such as trialkylaluminum including trimethylaluminum, triethylaluminum, tripropylaluminum, triisobutylaluminum, and trihexylaluminum; dialkylaluminum chloride including dimethylaluminum chloride, diethylaluminum chloride, dipropylaluminum chloride, diisobutylaluminum chloride, and dihexylaluminum chloride; alkylaluminum dichloride including methylaluminum dichloride, ethylaluminum dichloride, propylaluminum dichloride, isobutylaluminum dichloride and hexylaluminum dichloride; and dialkylaluminum hydride including dimethylaluminum hydride, diethylaluminum hydride, dipropylaluminum hydride, diisobutylaluminum hydride and dihexylaluminum hydride. Among them, preferable is trialkylaluminum, and more preferable are triethylaluminum and triisobutylaluminum.

In the transition metal catalyst composition containing cocatalyst according to the present invention, for preparing ethylene based polymers selected from ethylene homopolymers or copolymers of ethylene and α-olefin, the transition metal compound and the cocatalyst have preferably a molar ratio of transition metal (M):boron atom (B):aluminum atom (Al) in the range of 1:0~100:1~2,000, and more preferably 1:0.5~5:10~500. The above ratio enables the preparation of the ethylene homopolymers or the copolymers of ethylene and α-olefin, and the range of the ratio may be varied depending on purity of reaction.

According to another aspect of the present invention, the method of preparing ethylene based polymers by using the transition metal catalyst composition may be carried out by contacting the transition metal catalyst, cocatalyst, and ethylene or α-olefin comonomers, in the presence of appropriate organic solvent. Here, the transition metal catalyst and the cocatalyst components may be separately fed to the reactor, or those components may be mixed in advance and then fed to the reactor. The mixing conditions, such as the order of feeding, temperature, or concentration, are not particularly restricted.

Preferable examples of organic solvents usable in the preparing method may include (C3-C20) hydrocarbon, and specific examples thereof may include butane, isobutane, pentane, hexane, heptane, octane, isooctane, nonane, decane, dodecane, cyclohexane, methylcyclohexane, benzene, toluene, xylene, and the like.

Specifically, ethylene may be used alone as the monomer, in the preparation of the ethylene homopolymer. Here, the suitable pressure of ethylene may be 1~1000 atm, and more preferably 6~150 atm. Also, effectively, the polymerization reaction temperature may be 25° C.~200° C., and preferably 50° C.~180° C.

In addition, when the copolymer of ethylene and α-olefin is prepared, at least one selected from straight or branched chain (C3-C18) α-olefin, (C5-C20) cycloolefin, styrene, and styrene derivatives, may be used as comonomer, together with ethylene. Preferable examples of (C3-C18) α-olefin may be selected from the group consisting of propylene, 1-butene, 1-pentene, 4-methyl-1-pentene, 1-hexene, 1-heptene, 1-octene, 1-decene, 1-undecene, 1-dodecene, 1-tetradecene, 1-hexadecene, and 1-octadecene; preferable examples of (C5-C20) cycloolefin may be selected from the group consisting of cyclopentene, cyclohexene, norbornene, and phenylnorbornene; and preferable examples of styrene and derivatives thereof may be selected from the group consisting of styrene, α-methylstyrene, p-methylstyrene, and 3-chloromethylstyrene. In the present invention, the above olefin may be copolymerized with ethylene, or two or more kinds of olefin may be copolymerized with ethylene. Here, preferable ethylene pressure and polymerization reaction temperature are the same as the case where ethylene homopolymers are prepared. The copolymer prepared according to the method of the present invention may contain ethylene in a content of 30 wt % or more, preferably 60 wt % or more, and more preferably 60 to 99 wt %.

As described above, when the catalyst of the present invention is used, polymers from elastomers up to high density polyethylene (HDPE) that have density of 0.850 g/cc to 0.960 g/cc and melt flow of 0.001 to 15 dg/min can be easily and economically prepared by appropriately using (C4-C10) α-olefin as the comonomer and ethylene. Particularly, when the catalyst of the present invention is used, copolymers having density of 0.850 to 0.910 g/cc can be prepared at a high yield by using ethylene and 1-butene.

In addition, ethylene/propylene (EP) elastomer can be excellently prepared by using the catalyst of the present invention.

In addition, when the ethylene homopolymer or copolymer according to the present invention is prepared, hydrogen may be used as a molecular weight regulator in order to regulate the molecular weight. The weight average molecular weight (Mw) thereof is generally in the range of 5,000 to 1,000,000 g/mol.

Since the catalyst composition proposed by the present invention exists in a homogeneous state in the polymerization reactor, the catalyst composition may be preferably employed in a solution polymerization process carried out at a temperature higher than the melting point of the corresponding polymer. However, as disclosed by U.S. Pat. No. 4,752,597, the transition metal compound and cocatalyst may be supported on a porous metal oxide supporter, to thereby be used for slurry polymerization or a gas phase polymerization process, as a heterogeneous catalyst composition.

In addition, the present invention may include the compounds represented by Chemical Formulas 12 and 13 below, as an intermediate for preparing the transition metal compound of Chemical Formula 1.

[Chemical Formula 12]

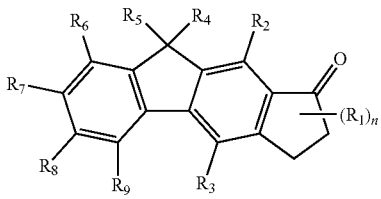

R₁ to R₉ and n each have the same definition as defined in Chemical Formula 1, provided that there is excluded a case where all of R₁, R₂, R₃, R₆, R₇, R₈, and R₉ are hydrogen.

[Chemical Formula 13]

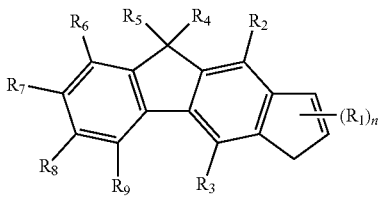

R₁ to R₉ and n each have the same definition as defined in Chemical Formula 1.

The transition metal compound or the catalyst composition containing the transition metal compound according to the present invention can be easily prepared at a high synthesis yield in an economical manner. Further, the transition metal compound or the catalyst composition according to the present invention can have excellent copolymerization reactivity with other olefins while maintaining high catalytic activity even at high temperature due to excellent thermal stability thereof and allow the preparation of high-molecular weight polymers at a high yield, resulting in higher commercial practicability as compared with the already known metallocene and non-metallocene based single activation point catalysts. Therefore, the transition metal catalyst composition according to the present invention can be usefully employed in the preparation of ethylene based polymers selected from ethylene homopolymers and copolymers of ethylene and α-olefin, having various physical properties.

Hereinafter, the embodiments of the present invention will be described in detail with reference to accompanying Examples, which are not intended to restrict the scope of the invention.

Unless mentioned otherwise, all experiments for synthesizing ligands and catalysts were carried out under nitrogen atmosphere by using standard Schlenk or glove-box techniques.

The organic solvents used in the reaction were subjected to reflux over sodium metal and benzophenone to thereby remove moisture, and then distilled immediately before use. $^1$H-NMR analyses of the synthesized ligands and catalysts were performed by using Bruker 500 MHz at room temperature.

Before use, n-heptane, as solvent for polymerization, was passed through a tube filled with molecular sieve 5 Å and activated alumina, and bubbled by high-purity nitrogen, to thereby sufficiently remove moisture, oxygen and other catalyst poison materials. The polymerized polymers were analyzed by the measurement methods described below.

1. Melt Flow Index (MI)

Measurement was conducted according to ASTM D 2839.

2. Density

Measurement was conducted by using density gradient tubes, according to ASTM D 1505.

3. Melting Temperature (Tm)

Measurement was conducted in the conditions of $2^{nd}$ heating at a rate of 10° C./min under nitrogen atmosphere, by using Dupont DSC 2910.

4. Molecular Weight and Molecular Weight Distribution

Measurement was conducted at 135° C. at a rate of 1.0 mL/min in the presence of 1,2,3-trichlorobenzene solvent, by using PL210 GPC equipped with PL Mixed-BX2+pre-Col, and molecular weight was calibrated by using PL polystyrene standards.

5. α-Olefin Content (Wt %) in Copolymer

Measurement was conducted by using 1,2,4-trichlorobenzene/$C_6D_6$ (7/3 by weight) mixture solvent at 120° C. in the $^{13}$C-NMR mode through Bruker DRX500 NMR spectrometer at 125 MHz. (Reference: Randal, J. C. *JMS-Rev. Macromol. Chem. Phys.* 1980, C29, 201)

The ratio of ethylene and α-olefin in EP polymers were quantified by using an infrared spectrometer.

[Example 1] Preparation of Mixture of Complex 1 and Complex 2

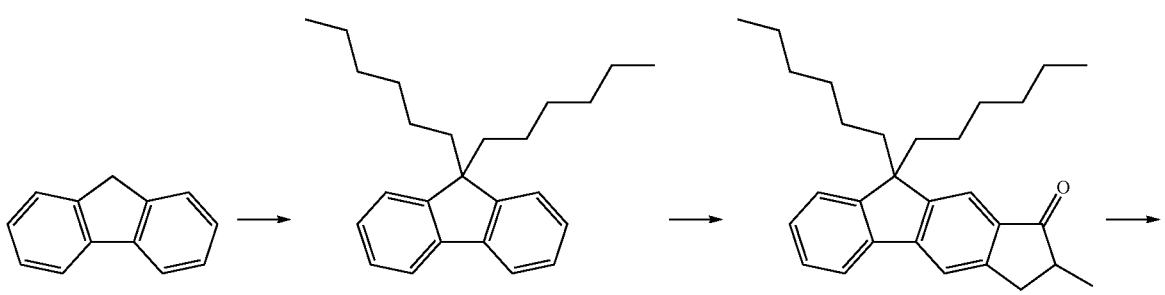

-continued

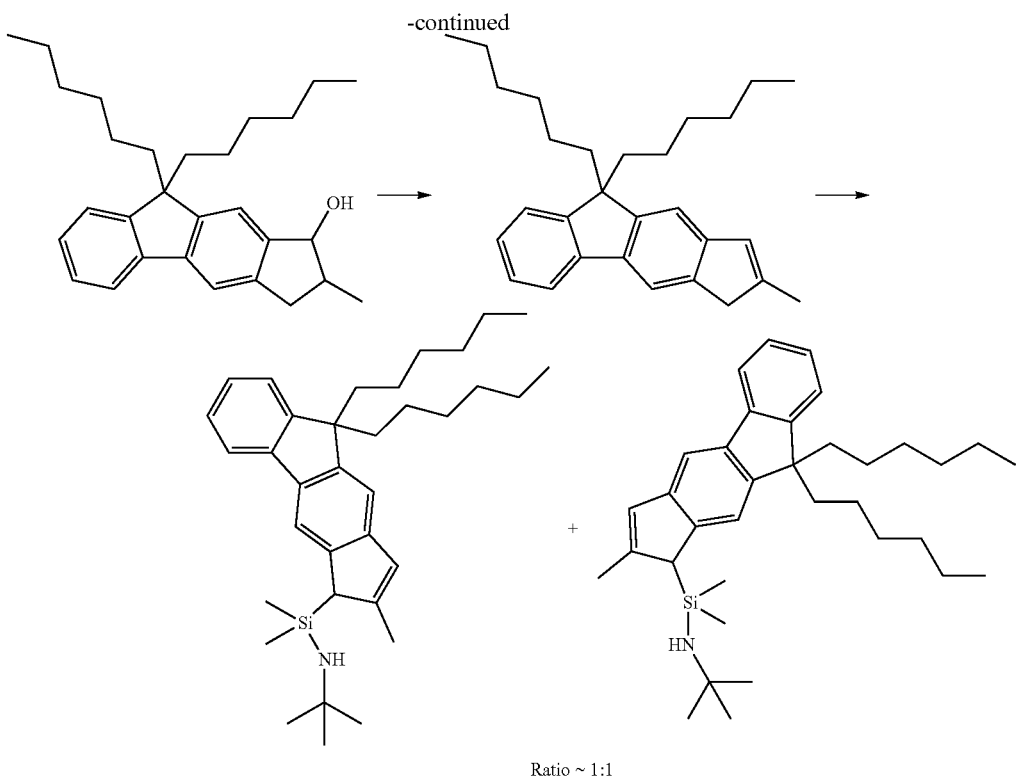

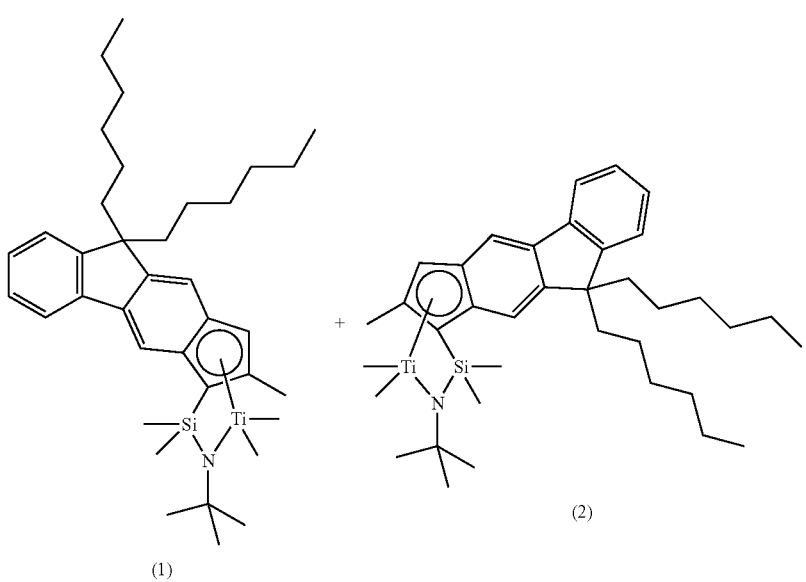

Synthesis of 9,9-dihexyl-9H-fluorene

A 2000 mL round flask was charged with 9H-fluorene (50 g, 300.1 mmol) and potassium t-butoxide (77.0 g, 721.9 mmol), and then 700 mL of DMSO was slowly injected thereto. 1-Bromohexane (119 g, 721.9 mmol) was slowly added thereto from a dropping funnel under nitrogen atmosphere. The mixture was stirred at room temperature for 24 hours, and the reaction was terminated by addition of 500 mL of distilled water. The organic layer collected by extraction with n-hexane was dried over magnesium sulfate, followed by removal of volatile materials, and then purified with n-hexane by using silica gel column chromatography, followed by drying and long-time storage at room temperature, to thereby obtain 90.0 g of 9,9-dihexyl-9H-fluorene (yield: 72.40%) as solid.

$^1$H-NMR (500 MHz, CDCl$_3$, ppm): δ=0.625-0.628 (m, 4H), 0.759-0.785 (m, 6H), 1.050-1.125 (m, 12H), 1.953-1.983 (t, 4H), 7.293-7.340 (m, 6H), 7.706-7.720 (d, 2H)

Synthesis of 9,9-dihexyl-2-methyl-2,3-dihydrocyclopenta[b]fluoren-1(9H)-one

A 2000 mL round flask was charged with 9,9-dihexyl-9H-fluorene (79 g, 236.2 mmol) and 2-bromo-2-methylpropanoyl bromide (54.3 g, 236.2 mmol), and then dissolved with 600 mL of carbon disulfide inputted thereto. Then, the reactor was cooled with ice water. Under nitrogen atmosphere, aluminum trichloride (78.7 g, 590.4 mmol) was slowly added thereto in ten lots over 2 hours. The mixture was stirred at room temperature for 8 hours, and then the reaction was terminated by addition of 500 mL of distilled water, followed by washing 3 times with 500 mL of distilled water. The organic layer was dried over magnesium sulfate, followed by removal of volatile materials and drying, to thereby obtain 89.0 g of 9,9-dihexyl-2-methyl-2,3-dihydrocyclopenta[b]fluoren-1(9H)-one (yield: 93.6%) as highly viscous oil.

$^1$H-NMR (500 MHz, CDCl$_3$, ppm): δ=0.601-0.627 (m, 4H), 0.741-0.774 (m, 6H), 1.000-1.126 (m, 12H), 1.366-1.380 (d, 3H), 1.961-2.202 (m, 4H), 2.789-2.801 (d, 2H), 3.445-3.498 (m, 1H), 7.375-7.383 (m, 3H), 7.731 (s, 2H), 7.764-7.779 (d, 1H)

Synthesis of 9,9-dihexyl-2-methyl-1,2,3,9 tetrahydrocyclopenta[b]fluoren-1-ol In a 1000 mL round flask, 9,9-dihexyl-2-methyl-2,3-dihydrocyclopenta[b]fluoren-1(9H)-one (85 g, 211.1 mmol) was dissolved in THF 400 mL and ethanol 400 mL, and then stirred. Sodium borohydride (NaBH$_4$) (10 g, 265.0 mmol) was added to the reaction product in five lots, and then stirred for 12 hours. The resultant mixture, after removal of solvent, was dissolved in ethylacetate, and then washed with water three times. The organic layer was dried over magnesium sulfate, followed by removal of volatile materials and drying, to thereby obtain 82.0 g of 9,9-dihexyl-2-methyl-1,2,3,9-tetrahydrocyclopenta[b]fluoren-1-ol (yield: 96.0%) (two isomers), as highly viscous oil.

$^1$H-NMR (500 MHz, CDCl$_3$, ppm): δ=0.628-0.631 (m, 8H), 0.762-0.788 (m, 12H), 1.109-1.136 (m, 24H), 1.198-1.212 (d, 3H), 1.314-1.327 (d, 3H), 1.522-1.535 (d, 1H), 1.830-1.846 (d, 1H), 1.956-1.963 (m, 8H), 2.323-2.352 (m, 1H), 2.525-2.572 (m, 1H), 2.628-2.655 (m, 1H), 2.733-2.779 (m, 1H), 3.011-3.057 (m, 1H), 3.164-3.210 (m, 1H), 4.783-4.812 (t, 1H), 5.052-5.077 (t, 1H), 7.289-7.380 (m, 8H), 7.525 (s, 1H), 7.558 (s, 1H), 7.672-7.685 (d, 2H)

Synthesis of 9,9-dihexyl-2-methyl-3,9-dihydrocyclopenta[b]fluorene

In a 500 mL round flask, 9,9-dihexyl-2-methyl-1,2,3,9-tetrahydrocyclopenta[b]fluoren-1-ol (80 g, 197.7 mmol) and p-toluene sulfonic acid (0.2 g) were dissolved in 320 mL of toluene, and then water was completely removed under reflux with Dean-Stark. The resultant material was cooled to room temperature, and then an aqueous ammonium chloride solution (150 mL) and 200 mL of diethyl ether were injected thereto, followed by separation of the organic layer. The organic layer collected by extracting the residue with diethyl ether was dried over magnesium sulfate, followed by removal of volatile materials, and then purified by using silica gel column chromatography tube, to thereby obtain 74.0 g of 9,9-dihexyl-2-methyl-3,9-dihydrocyclopenta[b]fluorene (yield: 96.8%).

$^1$H-NMR (500 MHz, CDCl$_3$, ppm): δ=0.611-0.671 (m, 4H), 0.755-0.784 (m, 6H), 1.041-1.140 (m, 12H), 1.943-1.976 (m, 4H), 2.200 (s, 3H), 3.373 (s, 2H), 6.556 (s, 1H), 7.208-7.381 (m, 4H), 7.653-7.668 (d, 1H), 7.700 (s, 1H)

Synthesis of N-tert-butyl-1-(9,9-dihexyl-2-methyl-3,9-dihydrocyclopenta[b]fluoren-3-yl)-1,1-dimethylsilanamine and N-tert-butyl-1-(9,9-dihexyl-2-methyl-1,9-dihydrocyclopenta[b]fluoren-1-yl)-1,1-dimethylsilanamine In a 500 mL round flask, 9,9-dihexyl-2-methyl-3,9-dihydrocyclopenta[b]fluorene (40.0 g, 103.5 mmol) was dissolved in 320 mL of diethyl ether, and then the temperature was lowered to −78° C. Then, n-butyllithium (2.5M hexane solution, 42 mL) was slowly injected thereto, followed by stirring at room temperature for 12 hours. After volatile materials were removed by vacuum, 350 mL of n-hexane was added to the mixture to lower the reactor temperature to −78° C., followed by addition of dichlorodimethylsilane (40 g). The temperature was again raised to room temperature, followed by stirring for 24 hours, and then salts were removed through filtering. Then, volatile materials were removed by vacuum. The product was again inputted to a 500 mL round flask, and dissolved in 320 mL of diethyl ether. The temperature was lowered to −78° C., and tert-butylamine (22.7 g, 310.4 mmol) was added thereto. The temperature was raised to room temperature, followed by stirring for 12 hours, and then volatile materials were completely removed by vacuum. Then, 200 mL of n-hexane was added to dissolve the resultant material, and salts were removed through filtering. The solvent was removed, to thereby obtain 48 g of a mixture of N-tert-butyl-1-(9,9-dihexyl-2-methyl-3,9-dihydrocyclopenta[b]fluoren-3-yl)-1,1-dimethylsilanamine and N-tert-butyl-1-(9,9-dihexyl-2-methyl-1,9-dihydrocyclopenta[b]fluoren-1-yl)-1,1-dimethylsilanamine (ratio=~1:1), (yield: 88.9%), as viscous material.

1H-NMR (500 MHz, C$_6$D$_6$, ppm): δ=0.132 (s, 3H), 0.177-0.198 (d, 6H), 0.270 (s, 1H), 0.804-0.879 (m, 12H), 0.973-1.295 (m, 50H), 2.170-2.348 (m, 14H), 3.398-3.428 (d, 2H), 6.745 (s, 2H), 7.337-7.434 (m, 6H), 7.518-7.908 (m, 6H)

Synthesis of (t-butylamido)dimethyl(9,9-dihexyl-2-methyl-3,9-dihydrocyclopenta[b]fluoren-3-yl)silanetitanium(IV)dimethyl (Complex 1) and (t-butylamido)dimethyl(9,9-dihexyl-2-methyl-1,9-dihydrocyclopenta[b]fluoren-1-yl)silanetitanium(IV) dimethyl (Complex 2)

In a 500 mL round flask, the mixture of N-tert-butyl-1-(9,9-dihexyl-2-methyl-3,9-dihydrocyclopenta[b]fluoren-3-yl)-1,1-dimethylsilanamine and N-tert-butyl-1-(9,9-dihexyl-2-methyl-1,9-dihydrocyclopenta[b]fluoren-1-yl)-1,1-dimethylsilanamine (ratio=~1:1) (8.64 g, 16.75 mmol) was dissolved in 130 mL of diethyl ether, and then the temperature was lowered to −78° C. Then, methyllithium (1.5M diethyl ether solution, 49.4 mL) was slowly injected thereto. The temperature was raised to room temperature, followed by stirring for 12 hours, to prepare lithium salt. In addition, in a dry box, TiCl$_4$ (16.75 mmol) and 150 mL of anhydrous n-hexane were inputted to a 500 mL round flask, and then the temperature was lowered to −78° C. Then, the prepared lithium salt was slowly added thereto. The temperature was again raised to room temperature, followed by stirring for 4 hours, and the solvent was removed by vacuum. The resultant material was dissolved in n-hexane, and then the filtrate was extracted through filtering. Again, the solvent was removed by vacuum, to thereby obtain 8.1 g of a mixture of Complex 1 and Complex 2 (ratio of approximately 1:1), as solid.

1H-NMR (500 MHz, $C_6D_6$, ppm): δ=0.079-0.091 (d, 6H), 0.623-0.645 (d, 6H), 0.813-1.336 (m, 56H), 1.601-1.619 (d, 18H), 2.071-2.514 (m, 14H), 7.025-7.035 (d, 2H), 7.330-8.099 (m, 12H)

[Example 2] Preparation of Mixture of Complex 3 and Complex 4

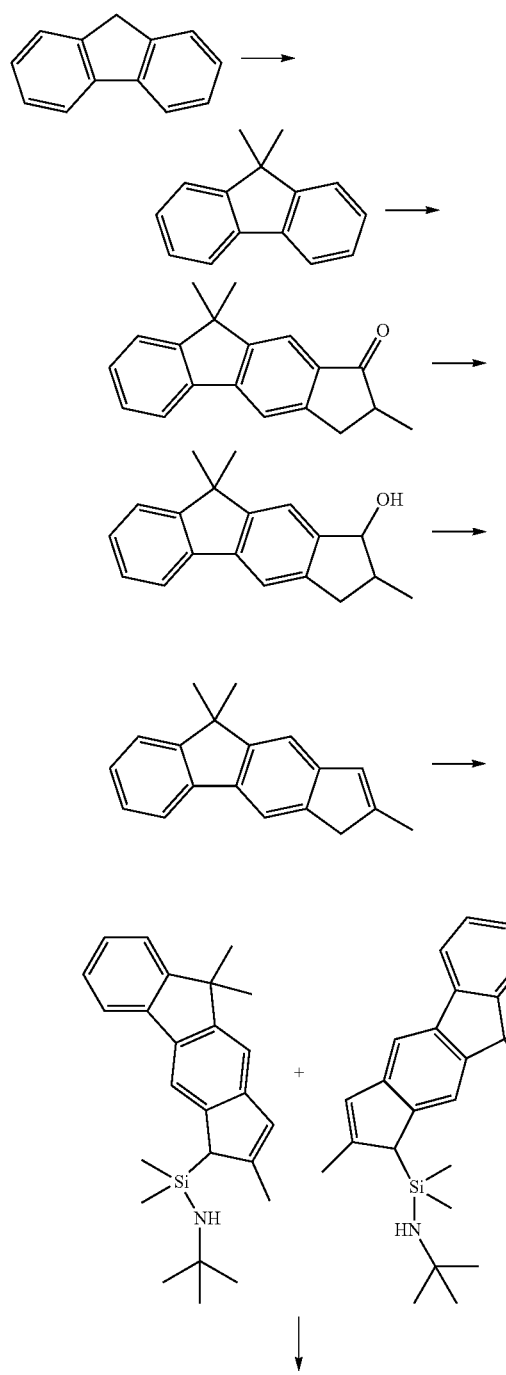

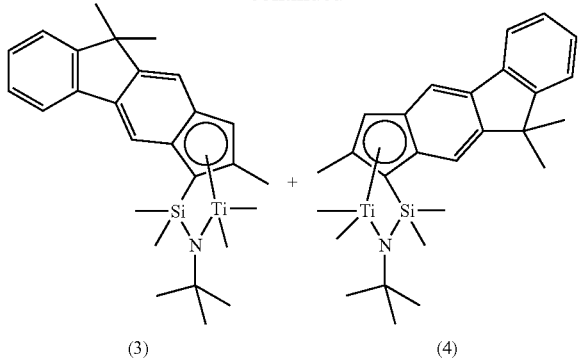

(3)  (4)

Synthesis of 9,9-dimethyl-9H-fluorene

A 2000 mL round flask was charged with 9H-fluorene (50 g, 300.1 mmol) and potassium t-butoxide (77.0 g, 721.9 mmol), and then 700 mL of DMSO was slowly injected thereto. Under nitrogen atmosphere, iodomethane (113.5 g, 800 mmol) was slowly dropped through a dropping funnel while the reactor temperature was maintained at 10° C. or lower. The mixture was stirred at room temperature for 24 hours, and the reaction was terminated by addition of 500 mL of distilled water. The organic layer collected by extraction with n-hexane was dried over magnesium sulfate, followed by removal of volatile materials, and then purified with n-hexane by using silica gel column chromatography tube, followed by drying, to thereby obtain 47.5 g of 9,9-dimethyl-9H-fluorene (yield: 81.50%) as white solid.

$^1$H-NMR (500 MHz, $CDCl_3$, ppm): δ=1.547 (s, 6H), 7.368-7.393 (t, 4H), 7.488-7.499 (d, 2H), 7.777-7.791 (d, 2H)

Synthesis of 2,9,9-trimethyl-2,3-dihydrocyclopenta [b]fluoren-1(9H)-one

A 2000 mL round flask was charged with 9,9-dimethyl-9H-fluorene (50 g, 257.4 mmol) and 2-bromo-2-methylpropanoyl bromide (61.0 g, 265.1 mmol), and then dissolved with 700 mL of carbon disulfide inputted thereto. Then, the reactor was cooled with ice water. Under nitrogen atmosphere, aluminum trichloride (85.8 g, 643.4 mmol) was slowly added thereto in ten lots over 2 hours. The mixture was stirred at room temperature for 8 hours, and then the reaction was terminated by addition of 500 mL of distilled water. The resultant mixture was diluted by adding 500 mL of methyl chloride and washed with 500 mL of distilled water three times. The organic layer was dried over magnesium sulfate, followed by removal of volatile materials and drying, and then recrystallized by using methyl chloride and methanol, to thereby obtain 64.0 g of 2,9,9-trimethyl-2,3-dihydrocyclopenta[b]fluoren-1(9H)-one (yield: 94.8%) as white solid.

$^1$H-NMR (500 MHz, $CDCl_3$, ppm): δ=1.354-1.369 (d, 3H), 1.517 (s, 6H), 2.784-2.811 (d, 2H), 3.444-3.496 (m, 1H), 7.376-7.429 (m, 2H), 7.471-7.485 (d, 2H), 7.763 (s, 1H), 7.795-7.808 (d, 2H), 7.832 (s, 1H)

Synthesis of 2,9,9-trimethyl-3,9-dihydrocyclopenta [b]fluorene

In a 1000 mL round flask, 2,9,9-trimethyl-2,3-dihydrocyclopenta[b]fluoren-1(9H)-one (50 g, 190.6 mmol) was dissolved THF 400 mL and ethanol 400 mL, and then stirred. Sodium borohydride (NaBH₄) (9.4 g, 247.8 mmol) was added to the reaction product in five lots, and then stirred for 12 hours. The resultant mixture, after removal of solvent, was dissolved in ethylacetate, and then washed with water three times. The organic layer was dried over magnesium sulfate, followed by removal of volatile materials. The dried reaction product was dissolved in 320 mL of toluene, and then inputted to a 500 mL round flask. After that, p-toluene sulfonic acid (0.2 g) was inputted thereto, and then water was completely removed under reflux with Dean-Stark. The resultant material was cooled to room temperature, and then an aqueous ammonium chloride solution (150 mL) and 200 mL of diethyl ether were injected thereto, followed by separation of the organic layer. The organic layer collected by extracting the residue with diethyl ether was dried over magnesium sulfate, followed by removal of volatile materials, and then purified by using silica gel column chromatography, to thereby obtain 42.0 g of 2,9,9-trimethyl-3,9-dihydrocyclopenta[b]fluorene (yield: 89.42%).

¹H-NMR (500 MHz, CDCl₃, ppm): δ=1.515 (s, 6H), 2.203 (s, 3H), 3.375 (s, 2H), 6.559 (s, 1H), 7.279-7.332 (m, 3H), 7.425-7.440 (d, 1H), 7.697-7.711 (d, 1H), 7.740 (s, 1H)

Synthesis of N-tert-butyl-1-(2,9,9-trimethyl-3,9-dihydrocyclopenta[b]fluoren-3-yl)-1,1-dimethylsilanamine and N-tert-butyl-1-(2,9,9-trimethyl-1,9-dihydrocyclopenta[b]fluoren-1-yl)-1,1-dimethylsilanamine In a 500 mL round flask, 2,9,9-trimethyl-3,9-dihydrocyclopenta[b]fluorene (15.0 g, 60.9 mmol) was dissolved in 300 mL of diethyl ether, and then the temperature was lowered to −78° C. Then, n-butyllithium (2.5M hexane solution, 24.8 mL) was slowly injected thereto, followed by stirring at room temperature for 12 hours. After the volatile materials were removed by vacuum, 350 mL of n-hexane was added to the mixture to lower the reactor temperature to −78° C., followed by addition of dichlorodimethylsilane (23 g). The temperature was again raised to room temperature, followed by stirring for 24 hours, and then salts were removed through filtering. Then, volatile materials were removed by vacuum. The product was again inputted to a 500 mL round flask, and dissolved in 320 mL of diethyl ether. The temperature was lowered to −78° C., and tert-butylamine (16.1 g, 152.2 mmol) was added thereto. The temperature was raised to room temperature, followed by stirring for 12 hours, and then volatile materials were completely removed by vacuum. Then, 200 mL of toluene was added to dissolve the resultant material, and salts were removed through filtering. The solvent was removed, to thereby obtain 21.0 g of a mixture of N-tert-butyl-1-(2,9,9-trimethyl-3,9-dihydrocyclopenta[b]fluoren-3-yl)-1,1-dimethylsilanamine and N-tert-butyl-1-(2,9,9-trimethyl-1,9-dihydrocyclopenta[b]fluoren-1-yl)-1,1-dimethylsilanamine (yield: 91.8%), as a viscous material.

¹H-NMR (500 MHz, C₆D₆, ppm): δ=0.085-0.098 (d, 6H), 0.229-0.253 (d, 6H), 0.555 (s, 2H), 1.161-1.179 (d, 18H), 1.534-1.559 (d, 12H), 2.304 (s, 6H), 3.385-3.422 (d, 2H), 6.747 (s, 2H), 7.303-8.049 (m, 12H)

Synthesis of (t-butylamido)dimethyl(2,9,9-trimethyl-3,9-dihydrocyclopenta[b]fluoren-3-yl)silanetitanium(IV) dimethyl (Complex 3) and (t-butylamido)dimethyl(2,9,9-trimethyl-1,9-dihydrocyclochloropenta[b]fluoren-1-yl)silanetitanium(IV) dimethyl (Complex 4)

In a 250 mL round flask, the mixture of N-tert-butyl-1-(2,9,9-trimethyl-3,9-dihydrocyclopenta[b]fluoren-3-yl)-1,1-dimethylsilanamine and N-tert-butyl-1-(2,9,9-trimethyl-1,9-dihydrocyclopenta[b]fluoren-1-yl)-1,1-dimethylsilanamine (10.4 g, 27.69 mmol) was dissolved in 200 mL of diethyl ether, and then the temperature was lowered to −78° C. Then, methyllithium (1.5M diethyl ether solution, 75.6 mL) was slowly injected thereto. The temperature was raised to room temperature, followed by stirring for 12 hours, to prepare lithium salt. In addition, in a dry box, TiCl₄ (5.25 g, 27.69 mmol) and 150 mL of anhydrous n-hexane were inputted to a 500 mL round flask, and then the temperature was lowered to −78° C. Then, the prepared lithium salt was slowly added thereto. Again, the temperature was raised to room temperature, followed by stirring for 4 hours, and then the solvent was removed by vacuum. The resultant material was again dissolved in toluene, and then the undissolved part was removed through filtering. Again, toluene was removed by vacuum, to thereby obtain 10.8 g of a mixture of Complex 3 and Complex 4, as solid.

¹H-NMR (500 MHz, C₆D₆, ppm): δ=−0.019-−0.010 (d, 6H), 0.641-0.647 (d, 6H), 0.794-2.212 (m, 48H), 7.004-7.025 (d, 2H), 7.106-8.092 (m, 12H)

[Example 3] Preparation of Mixture of Complex 5 and Complex 6

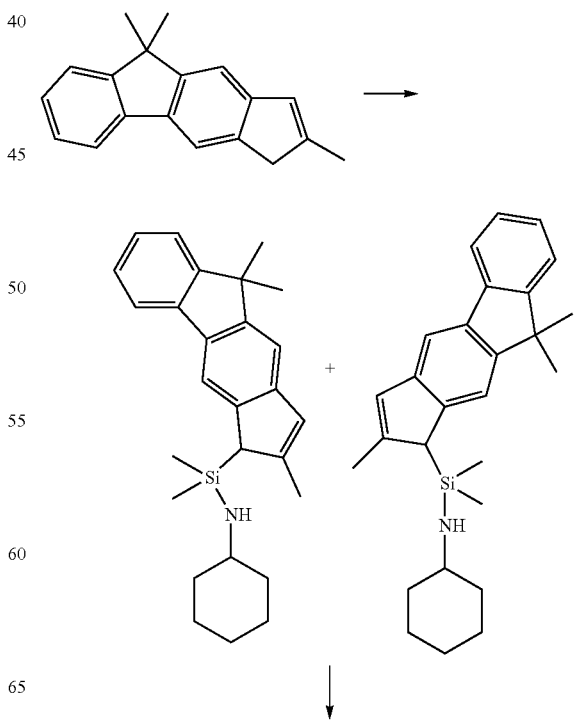

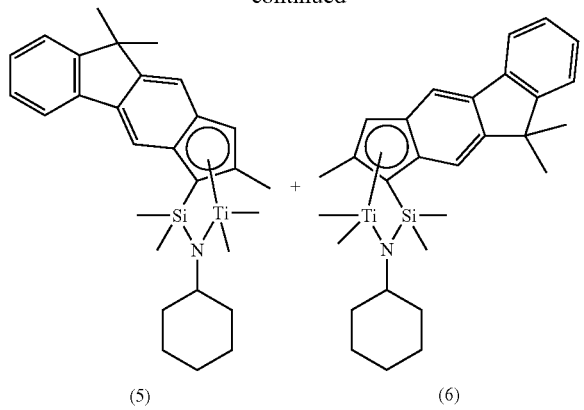

(5)    (6)

Synthesis of N-cyclohexal-1-(2,9,9-trimethyl-3,9-dihydrocyclopenta[b]fluoren-3-yl)-1,1-dimethylsilanamine and N-cyclohexyl-1-(2,9,9-trimethyl-1,9-dihydrocyclopenta[b]fluoren-1-yl)-1,1-dimethylsilanamine In a round flask, 2,9,9-trimethyl-3,9-dihydrocyclopenta[b]fluorene (7.5 g, 30.5 mmol) was dissolved in 300 mL of diethyl ether, and then the temperature was lowered to −78° C. Then, n-butyllithium (2.5M hexane solution, 12.4 mL) was slowly injected thereto, followed by stirring at room temperature for 12 hours. After the volatile materials were removed by vacuum, 200 mL of n-hexane was added to the mixture to lower the reactor temperature to −78° C., followed by addition of dichlorodimethylsilane (11.8 g, 91.4 mmol). The temperature was again raised to room temperature, followed by stirring for 24 hours, and then salts were removed through filtering. Then, volatile materials were removed by vacuum. The product was again inputted to a 200 mL round flask, and dissolved in 150 mL of diethyl ether. The temperature was lowered to −78° C., and cyclohexaneamine (9.05 g, 91.4 mmol) was added thereto. The temperature was raised to room temperature, followed by stirring for 12 hours, and then volatile materials were completely removed by vacuum. Then, 100 mL of toluene was added to dissolve the resultant material, and salts were removed through filtering. The solvent was removed, to thereby obtain 10.6 g of a mixture of N-cyclohexyl-1-(2,9,9-trimethyl-3,9-dihydrocyclopenta[b]fluoren-3-yl)-1,1-dimethylsilanamine and N-cyclohexyl-1-(2,9,9-trimethyl-1,9-dihydrocyclopenta[b]fluoren-1-yl)-1,1-dimethylsilanamine, as viscous material.

Synthesis of (cyclohexylamido)dimethyl(2,9,9-trimethyl-3,9-dihydrocyclopenta[b]fluoren-3-yl)silanetitanium(IV) dimethyl (Complex 5) and (cyclohexylamido)dimethyl(2,9,9-trimethyl-1,9-dihydrocyclochloropenta[b]fluoren-1-yl)silanetitanium(IV) dimethyl (Complex 6)

In a 250 mL of three-neck round flask, the well-dried mixture of N-cyclohexyl-1-(2,9,9-trimethyl-3,9-dihydrocyclopenta[b]fluoren-3-yl)-1,1-dimethylsilanamine and N-cyclohexyl-1-(2,9,9-trimethyl-1,9-dihydrocyclopenta[b]fluoren-1-yl)-1,1-dimethylsilanamine (10.6 g, 26.39 mmol) was dissolved in 200 mL of diethyl ether, and then the temperature was lowered to −78° C. Then, methyllithium (1.5M diethyl ether solution, 72.1 mL) was slowly injected thereto. The temperature was raised to room temperature, followed by stirring for 12 hours, to prepare lithium salt. In addition, in a dry box, TiCl$_4$ (5.00 g, 26.39 mmol) and 150 mL of anhydrous n-hexane were inputted to a 500 mL round flask, and then the temperature was lowered to −78° C. Then, the prepared lithium salt was slowly added thereto. Again, the temperature was raised to room temperature, followed by stirring for 4 hours, and then the solvent was removed by vacuum. The resultant material was again dissolved in toluene, and then the undissolved part was removed through filtering. Again, toluene was removed by vacuum, to thereby obtain 11.5 g of a mixture of Complex 5 and Complex 6, as solid.

$^1$H-NMR (500 MHz, C$_6$D$_6$, ppm): δ=−0.070–−0.049 (d, 6H), 0.628-0.634 (d, 6H), 0.764-2.195 (m, 50H), 4.779 (m, 2H), 6.985-7.002 (d, 2H), 7.100-8.095 (m, 12H)

[Example 4] Preparation of Mixture of Complex 7 and Complex 8

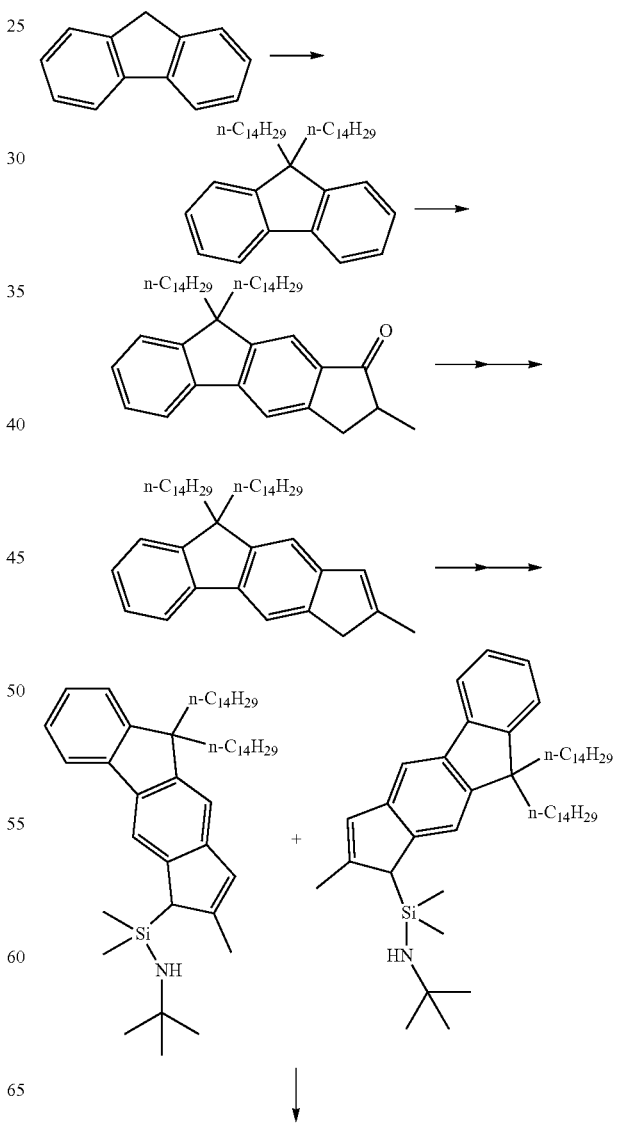

-continued

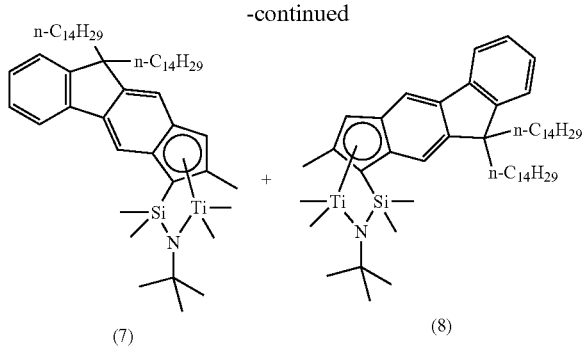

(7) + (8)

Synthesis of 9,9-ditetradecyl-9H-fluorene

A 2000 mL round flask was charged with 9H-fluorene (15 g, 90.24 mmol) and potassium tert-butoxide (21.2 g, 198.5 mmol), and then 300 mL of DMSO was slowly injected thereto. Under nitrogen atmosphere, 1-bromotetradecane (54 g, 198.5 mmol) was slowly dropped through a dropping funnel while the reactor temperature was maintained at 10° C. or lower. The mixture was stirred at room temperature for 24 hours, and the reaction was terminated by addition of 500 mL of distilled water. The organic layer collected by extraction with n-hexane was dried over magnesium sulfate, followed by removal of volatile materials, and then purified with n-hexane by using silica gel column chromatography tube, followed by drying, to thereby obtain 42.0 g of 9,9-ditetradecyl-9H-fluorene (yield: 83.26%) as white solid.

$^1$H-NMR (500 MHz, CDCl$_3$, ppm): δ=0.616-0.634 (m, 4H), 0.881-0.909 (m, 6H), 1.051-1.323 (m, 44H), 1.951-1.984 (t, 4H), 7.292-7.355 (m, 6H), 7.708-7.722 (d, 2H)

Synthesis of 2-methyl-9,9-ditetradecyl-2,3-dihydrocyclopenta[b]fluoren-1(9H)-one A 5000 mL round flask was charged with 9,9-ditetradecylmethyl-9H-fluorene (30 g, 53.7 mmol) and 2-bromo-2-methylpropanoyl bromide (12.7 g, 55.3 mmol), and then dissolved with 300 mL of carbon disulfide inputted thereto. Then, the reactor was cooled with ice water. Under nitrogen atmosphere, aluminum trichloride (15.7 g, 118.1 mmol) was slowly added thereto in ten lots over 2 hours. The mixture was stirred at room temperature for 8 hours, and then the reaction was terminated by addition of 100 mL of distilled water, followed by washing with 500 mL of distilled water three times. The organic layer was dried over magnesium sulfate, followed by removal of volatile materials and drying, to thereby obtain 30.0 g of 2-methyl-9,9-ditetradecyl-2,3-dihydrocyclopenta[b]fluoren-1(9H)-one (yield: 89.1%) as highly viscous oil.

$^1$H-NMR (500 MHz, CDCl$_3$, ppm): δ=0.590 (m, 4H), 0.867-0.895 (m, 6H), 1.024-1.295 (m, 44H), 1.367-1.382 (d, 3H), 1.963-2.204 (t, 4H), 2.792-2.826 (d, 2H), 3.448-3.500 (m, 1H), 7.372-7.400 (m, 3H), 7.726-7.780 (m, 3H)

Synthesis of 2-methyl-9,9-ditetradecyl-3,9-dihydrocyclopenta[b]fluorene

In a 500 mL round flask, 2-methyl-9,9-ditetradecyl-2,3-dihydrocyclopenta[b]fluoren-1(9H)-one (20 g, 31.9 mmol) was dissolved in 150 mL of THF and 150 mL of ethanol, and then stirred. Sodium borohydride (NaBH$_4$) (1.8 g, 47.8 mmol) was added to the reactant in five lots, and then stirred for 12 hours. The resultant mixture, after removal of solvent, was dissolved in ethylacetate, and then washed with water three times. The organic layer was dried over magnesium sulfate, followed by removal of volatile materials. The dried reactant was dissolved in 150 mL of toluene, and then inputted to a round flask. After that, p-toluene sulfonic acid (0.08 g) was inputted thereto, and then water was completely removed under reflux with Dean-Stark. The resultant material was cooled to room temperature, and then an aqueous ammonium chloride solution (100 mL) and 200 mL of diethyl ether were injected thereto, followed by separation of the organic layer. The organic layer collected by extracting the residue with diethyl ether was dried over magnesium sulfate, followed by removal of volatile materials, and then purified by using silica gel column chromatography, to thereby obtain 15.3 g of 2-methyl-9,9-ditetradecyl-3,9-dihydrocyclopenta[b]fluorene (yield: 78.5%).

$^1$H-NMR (500 MHz, CDCl$_3$, ppm): δ=0.649-0.665 (m, 4H), 0.891-0.918 (m, 6H), 1.059-1.319 (m, 44H), 1.953-1.986 (t, 4H), 2.206 (s, 3H), 3.378 (s, 2H), 6.562 (s, 1H), 7.237-7.332 (m, 4H), 7.663-7.678 (d, 1H), 7.710 (s, 1H)

Synthesis of N-tert-butyl-1-(9,9-ditetradecyl-2-methyl-3,9-dihydrocyclopenta[b]fluoren-3-yl)-1,1-dimethylsilanamine and N-tert-butyl-1-(9,9-ditetradecyl-2-methyl-1,9-dihydrocyclopenta[b]fluoren-1-yl)-1,1-dimethylsilanamine In a 250 mL round flask, 2-methyl-9,9-ditetradecyl-3,9-dihydrocyclopenta[b]fluorene (4.9 g, 8.0 mmol) was dissolved in 100 mL of anhydrous diethyl ether, and then the temperature was lowered to −78° C. Then, n-butyllithium (1.6M hexane solution, 5.5 mL) was slowly injected thereto, followed by stirring at room temperature for 12 hours. After volatile materials were removed by vacuum, 100 mL of n-hexane was added to the mixture to lower the reactor temperature to −78° C., followed by addition of dichlorodimethylsilane (2.9 g). The temperature was again raised to room temperature, followed by stirring for 24 hours, and then salts were removed through filtering. Then, volatile materials were removed by vacuum. The product was again inputted to a 250 mL round flask, and dissolved in 100 mL of diethyl ether. The temperature was lowered to −78° C., and tert-butylamine (1.8 g, 24.1 mmol) was added thereto. The temperature was raised to room temperature, followed by stirring for 12 hours, and then volatile materials were completely removed by vacuum. Then, 200 mL of n-hexane was added to dissolve the resultant material, and salts were removed through filtering. The solvent was removed, to thereby obtain 5.5 g of a mixture of N-tert-butyl-1-(9,9-ditetradecyl-2-methyl-3,9-dihydrocyclopenta[b]fluoren-3-yl)-1,1-dimethylsilanamine and N-tert-butyl-1-(9,9-ditetradecyl-2-methyl-1,9-dihydrocyclopenta[b]fluoren-1-yl)-1,1-dimethylsilanamine (ratio=~1:1), (yield: 92.7%), as high viscous material.

$^1$H-NMR (500 MHz, C$_6$D$_6$, ppm): δ=0.145 (s, 3H), 0.183-0.204 (d, 6H), 0.290 (s, 3H), 0.552 (s, 1H), 0.603 (s, 1H), 0.998-1.370 (m, 126H), 2.228-2.301 (m, 14H), 3.408-3.435 (d, 2H), 6.749-6.760 (d, 2H), 7.353-7.461 (m, 6H), 7.546-8.073 (m, 6H)

Synthesis of (t-butylamido)dimethyl(9,9-ditetradecyl-2-methyl-3,9-dihydrocyclopenta[b]fluoren-3-yl) silanetitanium(IV)dimethyl (Complex 7) and (t-butylamido)dimethyl(9,9-ditetradecyl-2-methyl-1,9-dihydrocyclopenta[b]fluoren-1-yl)silanetitanium(IV) dimethyl (Complex 8)

In a 250 mL round flask, a mixture of N-tert-butyl-1-(9, 9-ditetradecyl-2-methyl-3,9-dihydrocyclopenta[b]fluoren- 3-yl)-1,1-dimethylsilanamine and N-tert-butyl-1-(9,9-ditetradecyl-2-methyl-1,9-dihydrocyclopenta[b]fluoren-1-yl)-1,1-dimethylsilanamine (ratio=~1:1) (5.0 g, 6.8 mmol) was dissolved in 100 mL of diethyl ether, and then the temperature was lowered to −78° C. Then, methyllithium (1.5M diethyl ether solution, 18.5 mL) was slowly injected thereto. The temperature was raised to room temperature, followed by stirring for 12 hours, to prepare lithium salt. In addition, in a dry box, TiCl$_4$ (16.75 mmol) and 50 mL of anhydrous n-hexane were inputted to a 250 mL round flask, and then the temperature was lowered to −78° C. Then, the prepared lithium salt was slowly added thereto. The temperature was again raised to room temperature, followed by stirring for 4 hours, and the solvent was removed by vacuum. The resultant material was dissolved in n-hexane, and then the filtrate was extracted through filtering. Again, n-hexane was removed by vacuum, to thereby obtain 5.2 g of a mixture of Complex 7 and Complex 8 (ratio of approximately 1:1), as solid.

$^1$H-NMR (500 MHz, C$_6$D$_6$, ppm): δ=0.093-0.104 (d, 6H), 0.630-0.647 (d, 6H), 0.856-1.392 (m, 120H), 1.609-1.643 (d, 18H), 2.095-2.214 (m, 14H), 7.023-7.041 (d, 2H), 7.305-8.097 (m, 12H)

[Example 5] Preparation of Complex 9

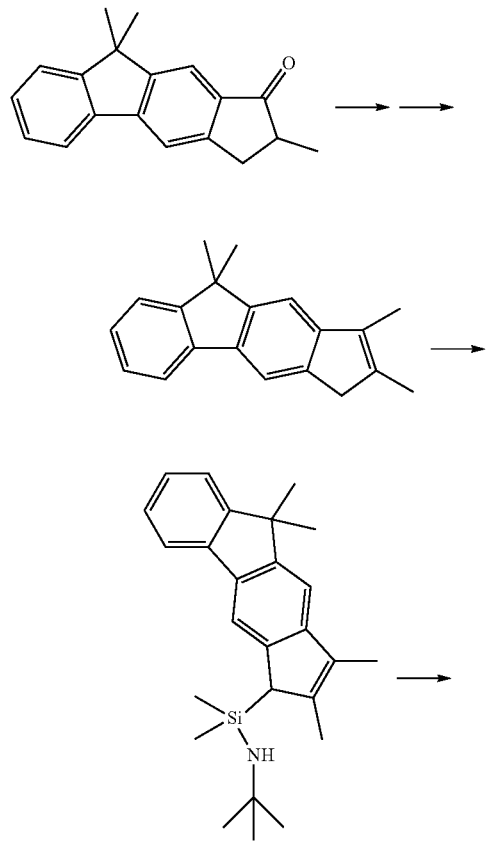

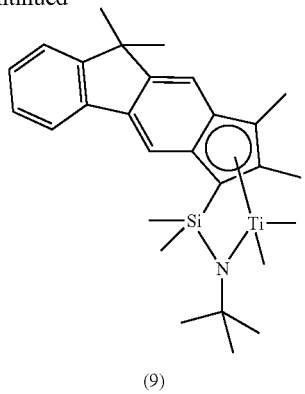

(9)

Synthesis of 1,2,9,9-tetramethyl-3,9-dihydrocyclopenta[b]fluorene

In a 1000 mL round flask, 2,9,9-trimethyl-2,3-dihydrocyclopenta[b]fluoren-1(9H)-one (50 g, 190.6 mmol) was dissolved in 400 mL of toluene, and then the temperature was lowered to 0° C. Then, 76 mL of 3M methylmagnesium bromide (THF solution) was slowly injected thereto, followed by stirring at room temperature for 12 hours. The reaction product was poured into a mixture of 200 mL of 1N-HCl aqueous solution and 200 g of ice. The mixture was stirred for 1 hour, followed by extraction with toluene, and then the organic layer was dried over magnesium sulfate, followed by removal of volatile materials. The dried reaction product was dissolved in 320 mL of toluene, and then inputted to a 500 mL round flask. After that, p-toluene sulfonic acid (0.2 g) was inputted thereto, and then water was completely removed under reflux with Dean-Stark. The resultant material was cooled to room temperature, and then an aqueous ammonium chloride solution (150 mL) and 200 mL of diethyl ether were injected thereto, followed by separation of the organic layer. The organic layer collected by extracting the residue with diethyl ether was dried over magnesium sulfate, followed by removal of volatile materials, and then purified by using silica gel column chromatography, to thereby obtain 42.0 g of 1,2,9,9-tetramethyl-3,9-dihydrocyclopenta[b]fluorene (yield: 84.6%).

$^1$H-NMR (500 MHz, CDCl$_3$, ppm): δ=1.547-1.568 (d, 6H), 2.123 (s, 6H), 3.352 (s, 2H), 7.273-7.363 (m, 3H), 7.442-7.456 (d, 1H), 7.711-7.45723 (m, 2H)

Synthesis of N-tert-butyl-1,1-dimethyl-1-(1,2,9,9-tetramethyl-3,9-dihydrocyclopenta[b]fluoren-3-yl)silanamine In a 500 mL round flask, 1,2,9,9-tetramethyl-3,9-dihydrocyclopenta[b]fluorene (15.0 g, 57.6 mmol) was dissolved in 300 mL of diethyl ether, and then the temperature was lowered to −78° C. Then, n-butyllithium (2.5M hexane solution, 25.4 mL) was slowly injected thereto, followed by stirring at room temperature for 12 hours. After the volatile materials were removed by vacuum, 350 mL of n-hexane was added to the mixture, to lower the reactor temperature to −78° C., followed by addition of dichlorodimethylsilane (23 g). The temperature was again raised to room temperature, followed by stirring for 24 hours, and then salts were removed through filtering. Then, volatile materials were removed by vacuum. The product was again inputted to a 500 mL round flask, and dissolved in 320 mL of diethyl ether. The temperature was lowered to −78° C., and tert-butylamine (10.5 g, 144.0 mmol) was added thereto. The temperature was raised to room temperature, followed by stirring for 12 hours, and then volatile materials were completely removed by vacuum. Then, 200 mL of toluene was added to dissolve the resultant material, and salts were removed through filtering. The solvent was removed, to thereby obtain 20.0 g of N-tert-butyl-1,1-dimethyl-1-(1,2,9,9-tetramethyl-3,9-dihydrocyclopenta[b]fluoren-3-yl)silanamine (yield: 89.1%), as viscous material.

$^1$H-NMR (500 MHz, C$_6$D$_6$, ppm): δ=0.166 (s, 3H), 0.222 (s, 3H), 0.610 (s, 1H) 1.239 (s, 9H), 1.618-1.651 (d, 6H), 2.256 (s, 6H), 3.437 (s, 1H), 7.361-7.466 (m, 3H), 7.590 (s, 1H), 7.958-7.973 (d, 1H), 8.128 (s, 1H)

Synthesis of (t-butylamido)-1,1-dimethyl(1,2,9,9-tetramethyl-3,9-dihydrocyclopenta[b]fluoren-3-yl)silanetitanium(IV) dimethyl (Complex 9)

In a 250 mL round flask, N-tert-buty-1,1-dimethyl-1-(1,2,9,9-tetramethyl-3,9-dihydrocyclopenta[b]fluoren-3-yl)-silanamine (10.8 g, 27.7 mmol) was dissolved in 200 mL of diethyl ether, and then the temperature was lowered to −78° C. Then, methyllithium (1.5M diethyl ether solution, 75.76 mL) was slowly injected thereto. The temperature was raised to room temperature, followed by stirring for 12 hours, to prepare lithium salt. In addition, in a dry box, TiCl$_4$ (5.26 g, 27.7 mmol) and 150 mL of anhydrous n-hexane were inputted to a 500 mL round flask, and then the temperature was lowered to −78° C. Then, the prepared lithium salt was slowly added thereto. Again, the temperature was raised to room temperature, followed by stirring for 4 hours, and then the solvent was removed by vacuum. The resultant material was again dissolved in toluene, and then the undissolved part was removed through filtering. Again, toluene was removed by vacuum, to thereby obtain 10.8 g of Complex 9 as solid.

$^1$H-NMR (500 MHz, C$_6$D$_6$, ppm): δ=−0.018 (s, 3H), 0.677 (s, 3H), 0.819 (s, 3H), 0.875 (s, 3H), 1.562-1.584 (m, 15H), 2.104 (s, 3H), 2.423 (s, 3H), 7.091-7.407 (m, 3H), 7.680-7.712 (m, 2H), 8.141 (s, 1H)

[Comparative Preparation Example 1] Preparation of (t-butylamido)dimethyl(tetramethylcyclopentadienyl)silanetitanium(IV) dimethyl

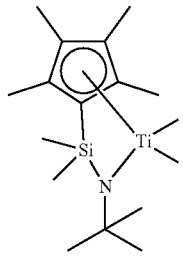

The (t-butylamido)dimethyl(tetramethylcyclopentadienyl)silanetitanium(IV) dimethyl compound was prepared by dissolving (t-butylamido)dimethyl(tetramethylcyclopentadienyl)silanetitanium(IV) dichloride purchased from Boulder Scientific Company of U.S., in diethyl ether, lowering the temperature to −78° C., and then reacting it with 2 equivalents of metal lithium.

Copolymerization of Ethylene and 1-Octene

[Examples 6 to 12 and Comparative Examples 1 and 2] Copolymerization of Ethylene and 1-Octene by Continuous Solution Polymerization Process Copolymerization of ethylene and 1-octene was carried out by using a continuous type polymerization apparatus as follows.

The catalysts synthesized in Examples 1 to 5 and Comparative Preparation Example 1 were used as single activation point catalysts, and cyclohexane was used as the solvent. The amounts of catalysts used are described in Table 1 below. Ti, Al, and B indicate a single activation point catalyst, triisobutyl aluminum as a cocatalyst, and triphenylmethyl tetrakis(pentafluorophenyl)borate, respectively. The respective catalysts were injected while they each were dissolved in toluene in a concentration of 0.2 g/l, and the synthesis was carried out by using 1-octene as comonomer. The conversion ratio of the reactor may be estimated through reaction conditions and temperature gradient in the reactor when one kind of polymer was prepared by polymerization in the respective reaction conditions. The molecular weight, in the case of a single activation point catalyst, was controlled as a function of the reactor temperature and the content of 1-octene, and conditions and results of the polymerization are shown in Table 1 below.

TABLE 1

| | | Example 6 | Example 7 | Example 8 | Example 9 | Example 10 |
|---|---|---|---|---|---|---|
| Polymerization conditions | Catalyst | Example 1 | Example 1 | Example 1 | Example 2 | Example 3 |
| | Total solution flux (kg/h) | 5 | 5 | 5 | 5 | 5 |
| | Feeding amount of ethylene (w %) | 8 | 6 | 6 | 6 | 6 |
| | Feeding molar ratio of 1-octene to ethylene (1-C8/C2) | 0.3 | 0.3 | 0.3 | 0.2 | 0.18 |
| | Feeding amount of Ti (μmol/kg) | 4 | 3 | 3 | 2.5 | 4 |
| | Al/Ti ratio | 45 | 50 | 50 | 60 | 45 |
| | B/Ti ratio | 3 | 3 | 3 | 3 | 3 |
| | Reaction Temperature (° C.) | 120 | 110 | 110 | 100 | 100 |
| Polymerization results | C2 conversion ratio (%) | 96 | 97 | 94 | 97 | 92 |
| | MI | 0.7 | 0.85 | 0.14 | 1.1 | 1.2 |
| | Density (g/cc) | 0.865 | 0.862 | 0.871 | 0.851 | 0.852 |
| | Weight average molecular weight | 98,300 | 95,400 | 127,400 | 91,400 | 90,200 |
| | Molecular weight distribution index | 1.9 | 2.0 | 2.2 | 2.1 | 2.0 |

TABLE 1-continued

|  |  | Example 11 | Example 12 | Comparative Example 1 | Comparative Example 2 |
|---|---|---|---|---|---|
| Polymerization conditions | Catalyst | Example 4 | Example 5 | Comparative Preparation Example 1 | Comparative Preparation Example 1 |
|  | Total solution flux (kg/h) | 5 | 5 | 5 | 5 |
|  | Feeding amount of ethylene (w %) | 6 | 6 | 8 | 8 |
|  | Feeding molar ratio of 1-octene to ethylene (1-C8/C2) | 0.3 | 0.2 | 0.22 | 0.19 |
|  | Feeding amount of Ti (μmol/kg) | 3 | 2.2 | 2 | 1.5 |
|  | Al/Ti ratio | 50 | 70 | 75 | 100 |
|  | B/Ti ratio | 3 | 3 | 3 | 3 |
|  | Reaction Temperature (° C.) | 120 | 100 | 113 | 104 |
| Polymerization results | C2 conversion ratio (%) | 98 | 98 | 94 | 92 |
|  | MI | 0.9 | 0.39 | 12.3 | 5.0 |
|  | Density (g/cc) | 0.865 | 0.869 | 0.875 | 0.878 |
|  | Weight average molecular weight | 94,500 | 108,000 | 62,400 | 72,000 |
|  | Molecular weight distribution index | 2.0 | 2.1 | 1.7 | 1.8 |

Ti: Ti in the single activation point catalyst
Al: Triisobutylaluminum as cocatalyst
B: Triphenylmethyl tetrakis(pentafluorenyl)borate as cocatalyst It can be seen from Examples 6 to 12 and Comparative Examples 1 and 2, in Examples 6 to 12 polymerized by using the catalyst developed in the present invention as compared with Comparative Examples 1 and 2, polymers having a high conversion ratio of ethylene even under the conditions of high-temperature (100° C. or higher), low density, and a low MI value meaning high molecular weight, can be easily obtained.

Copolymerization of Ethylene and 1-Butene

[Examples 13 to 15] Copolymerization of Ethylene and 1-Butene by Continuous Solution Polymerization Process Copolymerization of ethylene and 1-butene was carried out by using a continuous type polymerization apparatus, in the same method as the copolymerization of ethylene and 1-octene by the continuous solution polymerization mentioned in Examples 6 to 12 except that 1-butene was used as the comonomer, as follows. Detailed polymerization conditions and polymerization results are shown in Table 2 below.

TABLE 2

|  |  | Example 13 | Example 14 | Example 15 |
|---|---|---|---|---|
| Polymerization conditions | Catalyst | Example 1 | Example 1 | Example 1 |
|  | Total solution flux (kg/h) | 5 | 5 | 5 |
|  | Feeding amount of ethylene (w %) | 6 | 6 | 6 |
|  | Feeding molar ratio of 1-butene to ethylene (1-C4/C2) | 0.6 | 0.5 | 0.4 |
|  | Feeding amount of Ti (μmol/kg) | 4 | 3.5 | 3 |
|  | Al/Ti ratio | 45 | 48 | 50 |
|  | B/Ti ratio | 3 | 3 | 3 |
|  | Reaction Temperature (° C.) | 104 | 101 | 101 |
| Polymerization results | C2 conversion ratio (%) | 99 | 98 | 96 |
|  | MI | 0.7 | 0.36 | 0.19 |
|  | Density (g/cc) | 0.860 | 0.863 | 0.865 |
|  | Weight average molecular weight | 98,200 | 109,400 | 121,200 |

TABLE 2-continued

|  | Example 13 | Example 14 | Example 15 |
|---|---|---|---|
| molecular weight Molecular weight distribution index | 1.9 | 2.2 | 2.3 |

Ti: Ti in the single activation point catalyst
Al: Triisobutylaluminum as cocatalyst
B: Triphenylmethyl tetrakis(pentafluorenyl)borate as cocatalyst It can be seen from Table 2 above, that, in Examples 13 to 15 polymerized by using the catalyst developed in the present invention, ultralow density elastomers having a high conversion ratio of ethylene even under the conditions of high temperature (100° C. or higher) and high molecular weight even with using a small amount of 1-butene (1-C4/C2 molar ratio=0.4) can be easily obtained at a high yield.

The present invention has been described in detail with reference to examples as set forth above, but those skilled in the art to which the invention pertains can make various modifications without departing from the spirit and scope of the invention defined in appended claims. Therefore, alterations and modifications of the examples of the present invention would not depart from the technique of the present invention.

The invention claimed is:
1. A compound of chemical formula 13:

[Chemical Formula 13]

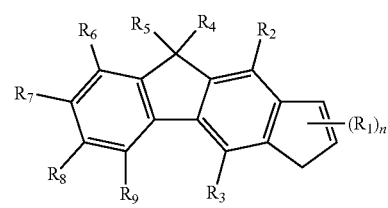

In Chemical Formula 13,
$R_1$ is hydrogen, (C1-C50)alkyl, halo(C1-C50)alkyl, (C3-C50)cycloalkyl, (C6-C30)aryl, (C6-C30)aryl(C1-C50)alkyl, ((C1-C50)alkyl(C6-C30)aryl)(C1-C50)alkyl, —NR$^a$R$^b$, —SiR$^c$R$^d$R$^e$, or 5- through 7-membered N-heterocycloalkyl containing at least one nitrogen atom;

R$_2$ and R$_3$ each are independently hydrogen, (C1-C50)alkyl, (C1-C50)alkoxy, halo(C1-C50)alkyl, (C3-C50)cycloalkyl, (C6-C30)aryl, (C6-C30)aryloxy, (C1-C50)alkyl(C6-C30)aryloxy, (C6-C30)aryl(C1-C50)alkyl, ((C1-C50)alkyl(C6-C30)aryl)(C1-C50)alkyl, —NR$^a$R$^b$ or —SiR$^c$R$^d$R$^e$;

R$_4$ and R$_5$ each are independently (C1-C50)alkyl, halo(C1-C50)alkyl, (C3-C50)cycloalkyl, (C6-C30)aryl, (C6-C30)aryl(C1-C50)alkyl, ((C1-C50)alkyl(C6-C30)aryl)(C1-C50)alkyl, —NR$^a$R$^b$, or —SiR$^c$R$^d$R$^e$;

R$_6$, R$_7$, R$_8$ and R$_9$ each are independently hydrogen, (C1-C50)alkyl, halo(C1-C50)alkyl, (C3-C50)cycloalkyl, (C1-C50)alkoxy, (C6-C30)aryl, (C6-C30)aryl(C1-C50)alkyl, ((C1-C50)alkyl(C6-C30)aryl)(C1-C50)alkyl, (C6-C30)aryloxy, (C1-C50)alkyl(C6-C30)aryloxy, N-carbazolyl, —NR$^a$R$^b$, or —SiR$^c$R$^d$R$^e$, or may be linked to an adjacent substituent via (C1-C5)alkylene to form a ring, and at least one —CH$_2$— of the alkylene may be substituted by a hetero atom selected from —O—, —S—, and —NR'—, and the alkylene may be further substituted with (C1-C50)alkyl;

aryl of R$_1$ to R$_9$ may be further substituted with at least one substituent selected from the group consisting of (C1-C50)alkyl, halo(C1-C50)alkyl, (C1-C50)alkoxy, (C6-C30)aryloxy, (C6-C30)aryl, (C1-C50)alkyl(C6-C30)aryl, and (C6-C30)aryl(C1-C50)alkyl;

R' and R$^a$ to R$^e$ each are independently (C1-C50)alkyl or (C6-C30)aryl;

n is an integer of 1 or 2, each R$_1$ may be the same or different when n is 2.

* * * * *